United States Patent [19]
Fujitaka et al.

[11] Patent Number: 6,041,660
[45] Date of Patent: Mar. 28, 2000

[54] TENSILE STRENGTH TESTER

[75] Inventors: Junichi Fujitaka; Yuichi Jibiki, both of Kanagawa, Japan

[73] Assignee: Ricoh Company, Ltd., Tokyo, Japan

[21] Appl. No.: 09/107,281

[22] Filed: Jun. 30, 1998

[30] Foreign Application Priority Data

| Jul. 1, 1997 | [JP] | Japan | 9-191887 |
| Nov. 14, 1997 | [JP] | Japan | 9-313980 |
| Nov. 21, 1997 | [JP] | Japan | 9-321649 |
| Jun. 15, 1998 | [JP] | Japan | 10-167600 |
| Jun. 16, 1998 | [JP] | Japan | 10-168392 |
| Jun. 24, 1998 | [JP] | Japan | 10-176952 |

[51] Int. Cl.$^7$ ...................................................... G01N 3/02
[52] U.S. Cl. ............................................................ 73/826
[58] Field of Search .............................. 73/760, 761, 826, 73/862.03, 862.01

[56] References Cited

U.S. PATENT DOCUMENTS

| 4,558,599 | 12/1985 | Sachs | 73/761 |
| 4,662,227 | 5/1987 | Peterson | 73/834 |
| 4,753,115 | 6/1988 | Moody | 73/862.01 |
| 5,773,722 | 6/1998 | Helderman | 73/826 |
| 5,792,961 | 8/1998 | Giebner et al. | 73/826 |

FOREIGN PATENT DOCUMENTS 7-9391  2/1995  Japan .

*Primary Examiner*—Max Noori
*Attorney, Agent, or Firm*—Oblon, Spivak, McClelland, Maier & Neustadt, P.C.

[57] ABSTRACT

A tensile strength tester feasible of the present invention is feasible for automation and includes a rotating member and a pulling member connected to each other. A torque is transferred from the rotating member to the pulling member with a counterforce being absorbed at the position where the two members are connected. Such a connecting portion is prevented from becoming loose. The tester is capable of measuring a tensile strength when a screw member fitted in a base material is pulled out of the base material.

57 Claims, 44 Drawing Sheets

Fig. 8B
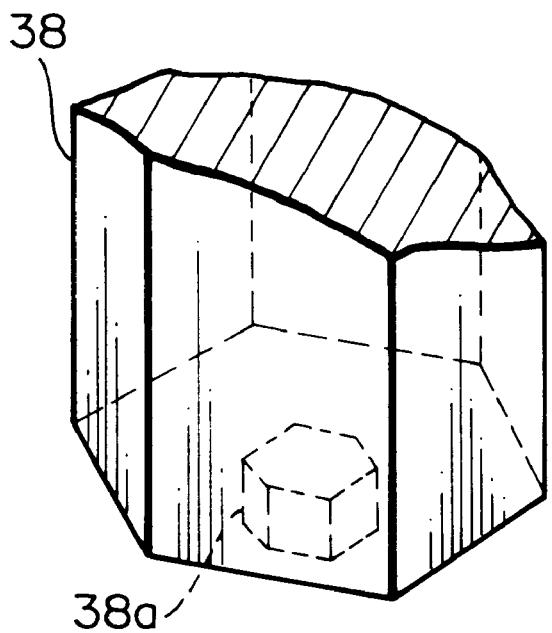
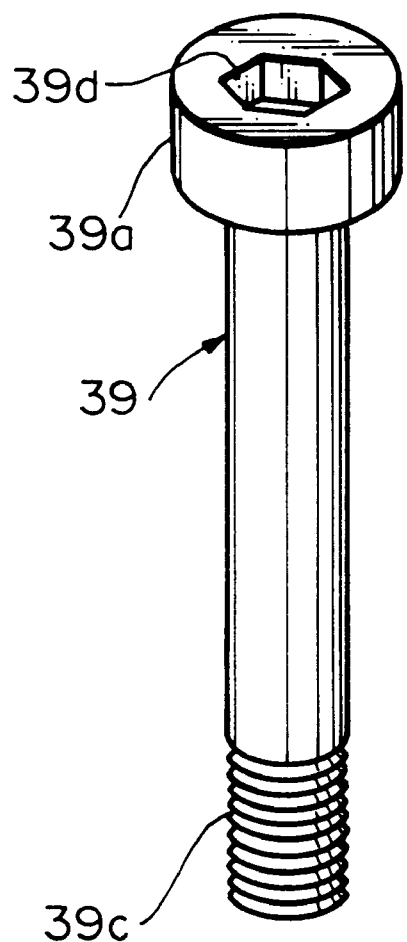
Fig. 8C
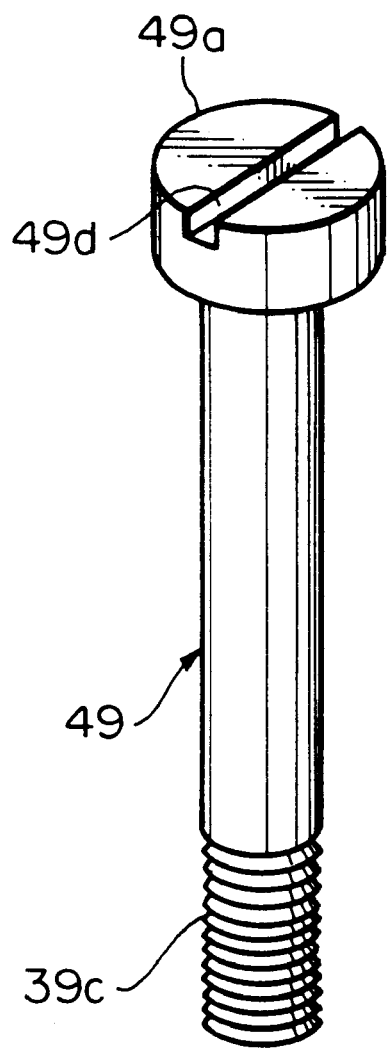

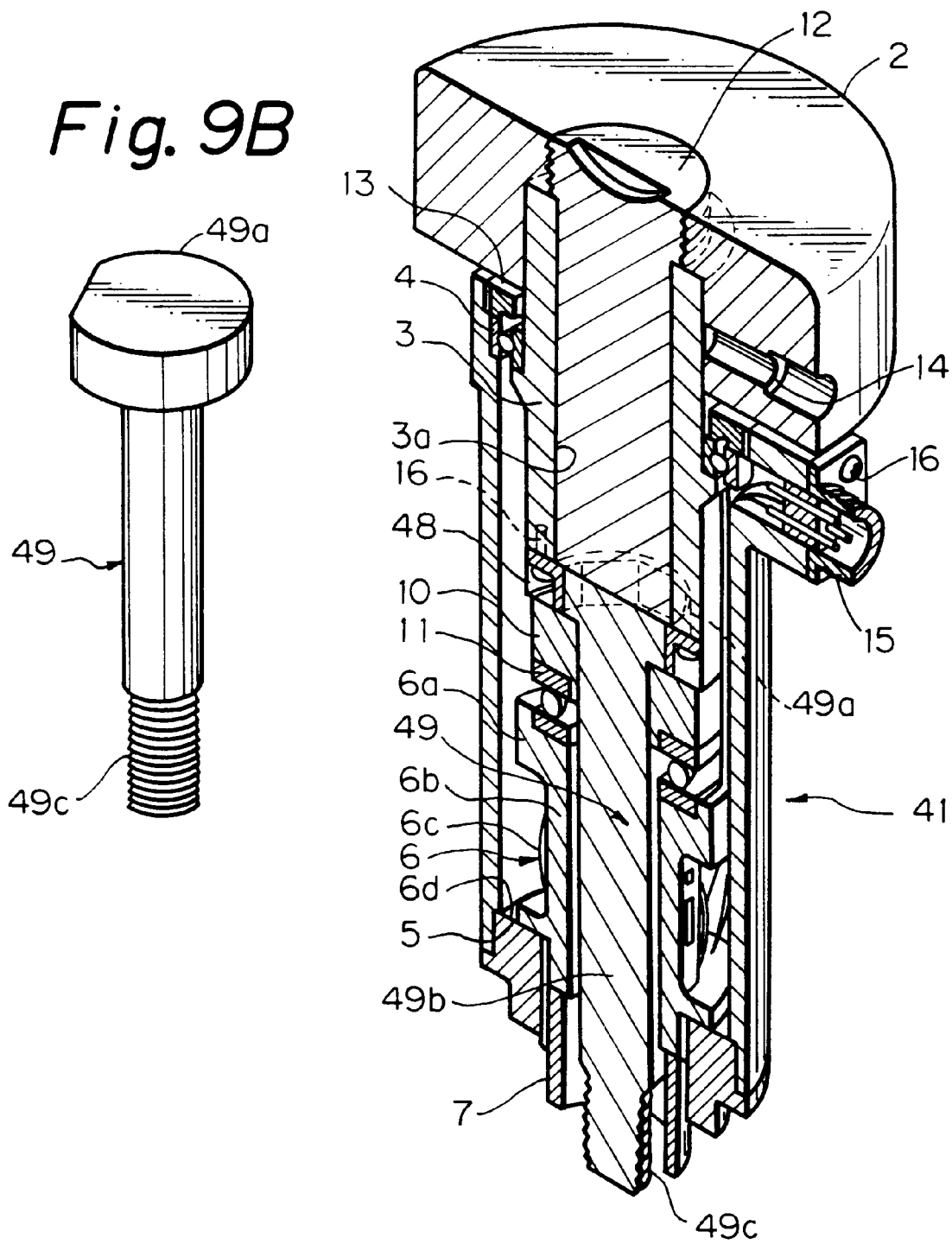

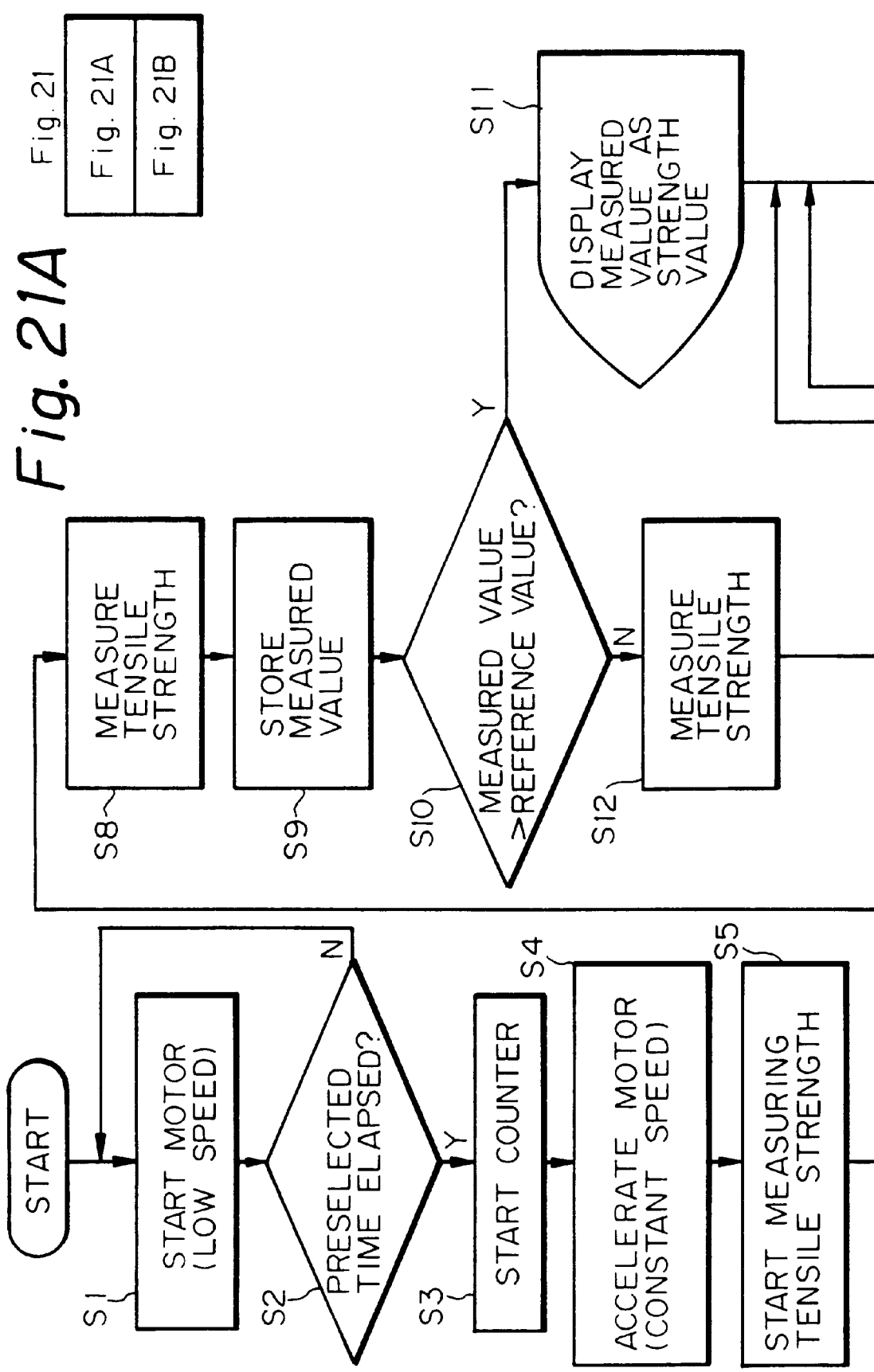

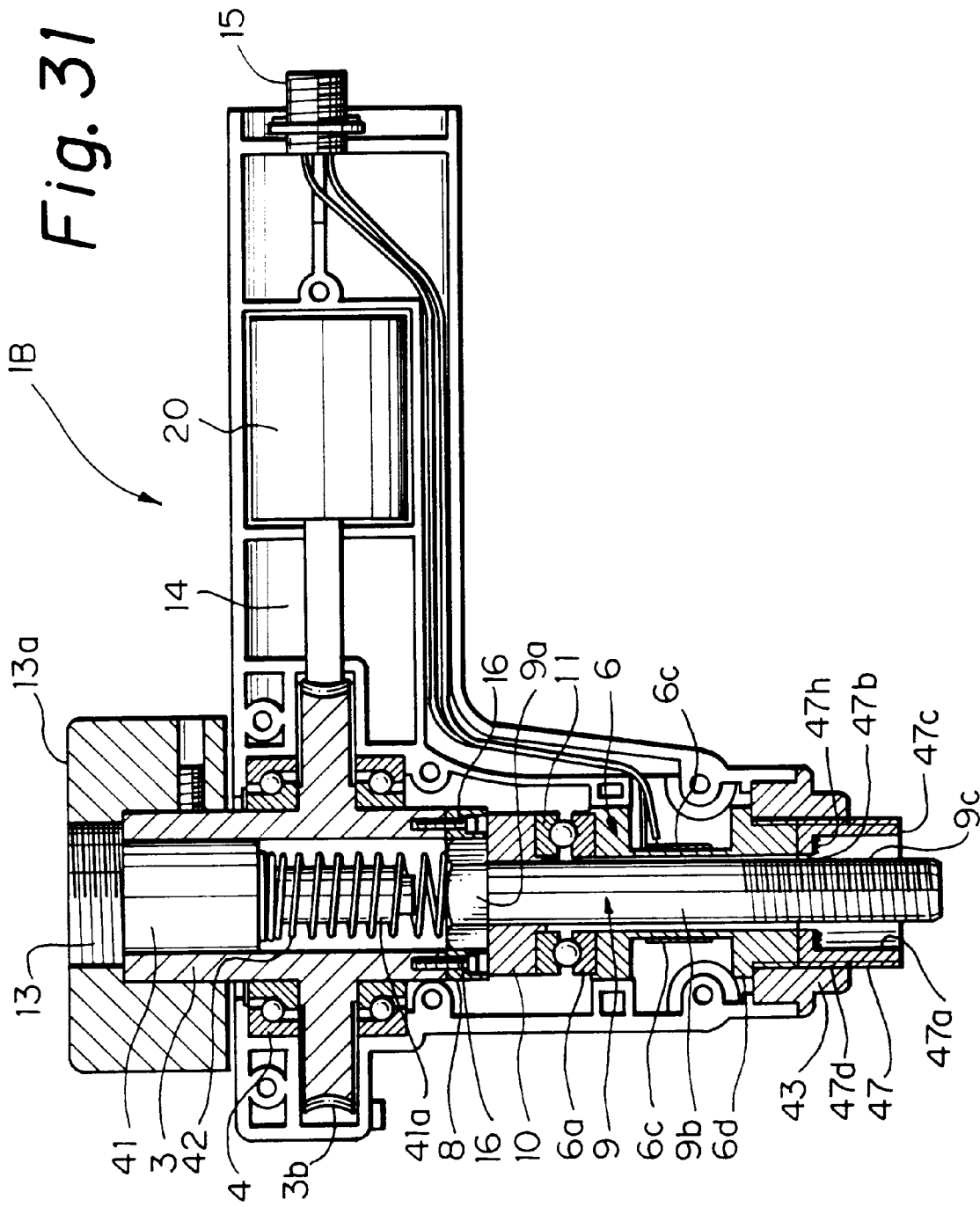

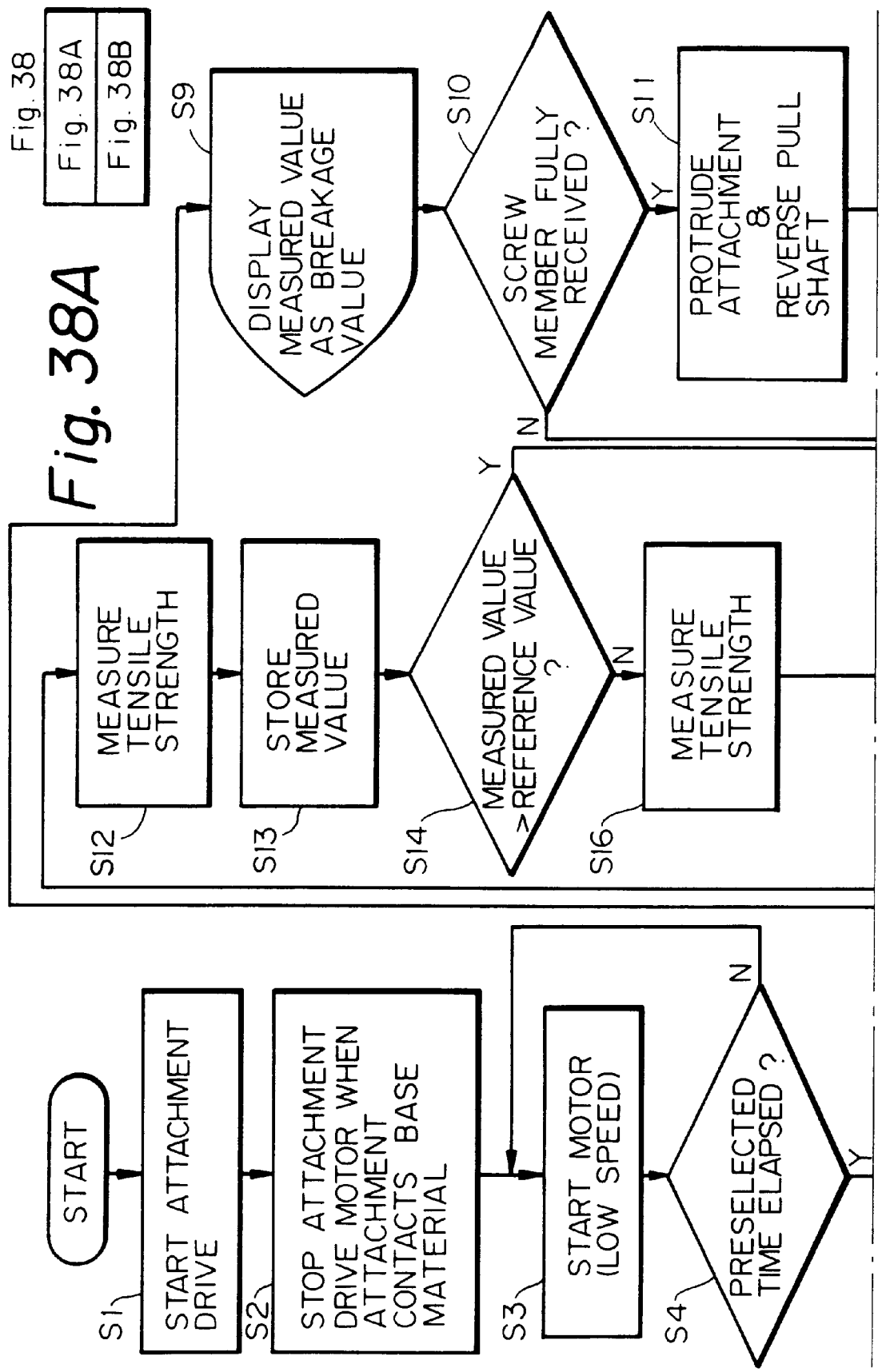

TENSILE STRENGTH TESTER

BACKGROUND OF THE INVENTION

The present invention relates to a tensile strength tester and, more particularly, to a tensile strength tester capable of measuring a tensile strength by pulling a screw member fitted in a base material out of the base material.

A resin molding, thin plate or similar article is often formed with screw portions and connected to another article by threaded engagement. To insure rigid connection, it is a common practice to implement each screw portion as an independent nut and connected to the base material by burying, welding, press fitting or similar technology. It is necessary to test the strength of connection between the screw member and the base member because the screw member should guarantee rigid connection between two articles. For the test, use is made of a tensile strength tester or tensile testing machine which exerts a tensile force on the screw member while fixing the base member in place, and measures the maximum connecting strength, i.e., the tensile strength of the base material and screw member in terms of a tensile force caused them to start separating from each other.

An Amsler type testing machine which is not portable is a typical conventional tensile strength tester. However, the problem with this type of tester is that preparation for measurement is troublesome and time-consuming while needing expertness. Further, the tester is a general purpose testing machine and therefore expensive. Moreover, it is difficult to measure the tensile strength of the base material and screw member at a work cite, e.g., the cite of injection molding. Particularly, the intention of the measurement of a tensile strength test is to improve the quality of products by feeding back the result of measurement to a production line. In this sense, a tester capable of readily measuring and testing the base material and screw member is desirable.

In light of the above, Japanese Patent Laid-Open Publication No. 3-125941, for example, discloses a tensile strength tester capable of being brought to a work cite and measuring or estimating the tensile strength of screw members with ease. However, the tester taught in this document has some problems left unsolved, as follows. The tester is too large and heavy to be easily handled by a person and not easily marketable. A portion where a rotatable member and a pulling member are connected is apt to become loose. The pulling member is not readily replaceable and obstructs easy maintenance of the tester. The tester operated by hand cannot stably measure tensile strength and should preferably be automated by use of, e.g., a motor.

SUMMARY OF THE INVENTION

It is therefore an object of the present invention to provide a tensile strength tester capable of transferring a torque while absorbing a counterforce at a position where a rotatable member and a pulling member are connected to each other, capable of preventing the connecting portion from becoming loose, and feasible for automation.

It is another object of the present invention to provide a tensile strength tester capable of promoting easy replacement of a pulling member and therefore easy maintenance and feasible for automation.

It is another object of the present invention to provide a tensile strength tester which is small size, light weight and feasible for automation.

BRIEF DESCRIPTION OF THE DRAWINGS

The above and other objects, features and advantages of the present invention will become apparent from the following detailed description taken with the accompanying drawings in which:

FIG. 8B is a fragmentary enlarged view of the second embodiment;

FIG. 8C is a perspective view showing a modification of a pull shaft included in the third embodiment;

FIG. 9A is a sectional perspective view showing a fourth manual drive type embodiment of the tensile strength tester in accordance with present invention in a plane containing the axis of the tester;

FIG. 9B is an enlarged view of a pull shaft included in the fourth embodiment;

FIG. 31 is a sectional front view showing a fourth motor drive type embodiment of the tensile strength tester in accordance with the present invention;

DESCRIPTION OF THE PREFERRED EMBODIMENTS

Figure 1:
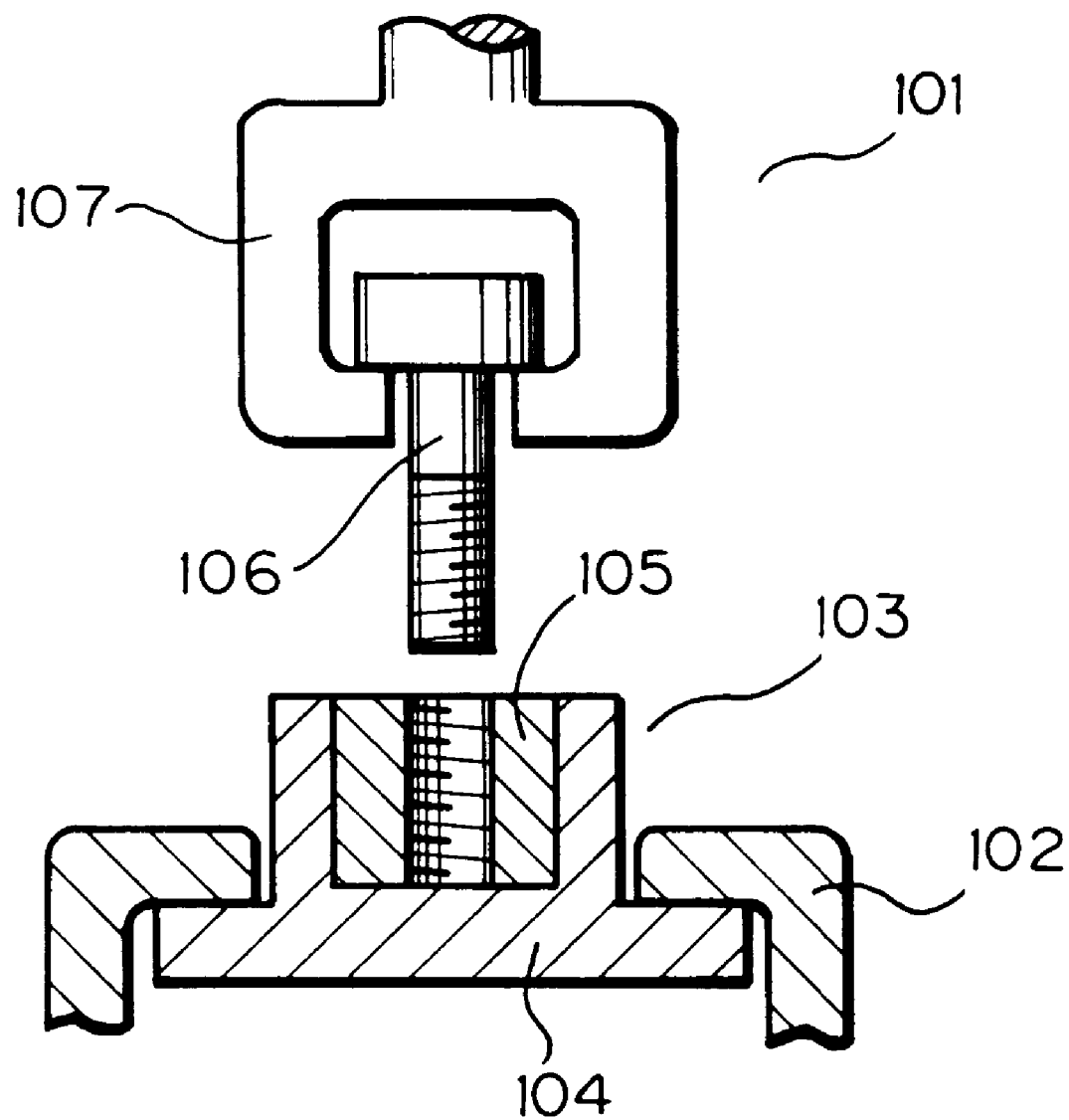
FIG. 1 is a fragmentary view showing a conventional tensile strength tester.

To better understand the present invention, brief reference will be made to a conventional tensile strength tester, shown in FIG. 1. As shown, the tensile strength tester is implemented as an Amsler type testing machine or similar tensile strength tester 101. The tester 101 includes a fixing portion 102 and a chuck 107 formed of metal. An article 103 to be measured and formed by injection molding is fixed in place by the fixing portion 102. The article 103 is made up of a base material 104 and a screw member 105 buried in the base material 104. The article 103 is cut out in such dimensions that the base material 104 can be mounted to the fixing portion 102 together with the screw member 105. For measurement, a bolt 106 is driven into the screw member 105. Subsequently, the chuck 107 is caused to chuck the bolt 106 and then pull it upward, as viewed in FIG. 1. The pulling force of the chuck 107 is increased until the screw member 105 has been fully pulled out of the base material 104. The tensile strength of the base material 104 and screw member 105 is determined in terms of a tensile force caused the screw member 105 to start separating from the base material 104.

However, the above conventional tester has some problems left unsolved, as follows. Because the article 103 must be cut out in a particular configuration matching with the fixing portion 102, preparation for the measurement is troublesome and time-consuming while needing expertness. The tester is a general purpose testing machine and therefore expensive. Moreover, because the tester is large size and not portable, it is almost impossible to measure the tensile strength of the base material 104 and screw member 105 at, e.g., the cite of injection molding. Particularly, the intention of the measurement of a tensile strength test is to improve the quality of products by feeding back the result of measurement to a production line. In this sense, a tester capable of readily measuring and testing the base material 104 and screw member 105 is desirable.

Figure 2:
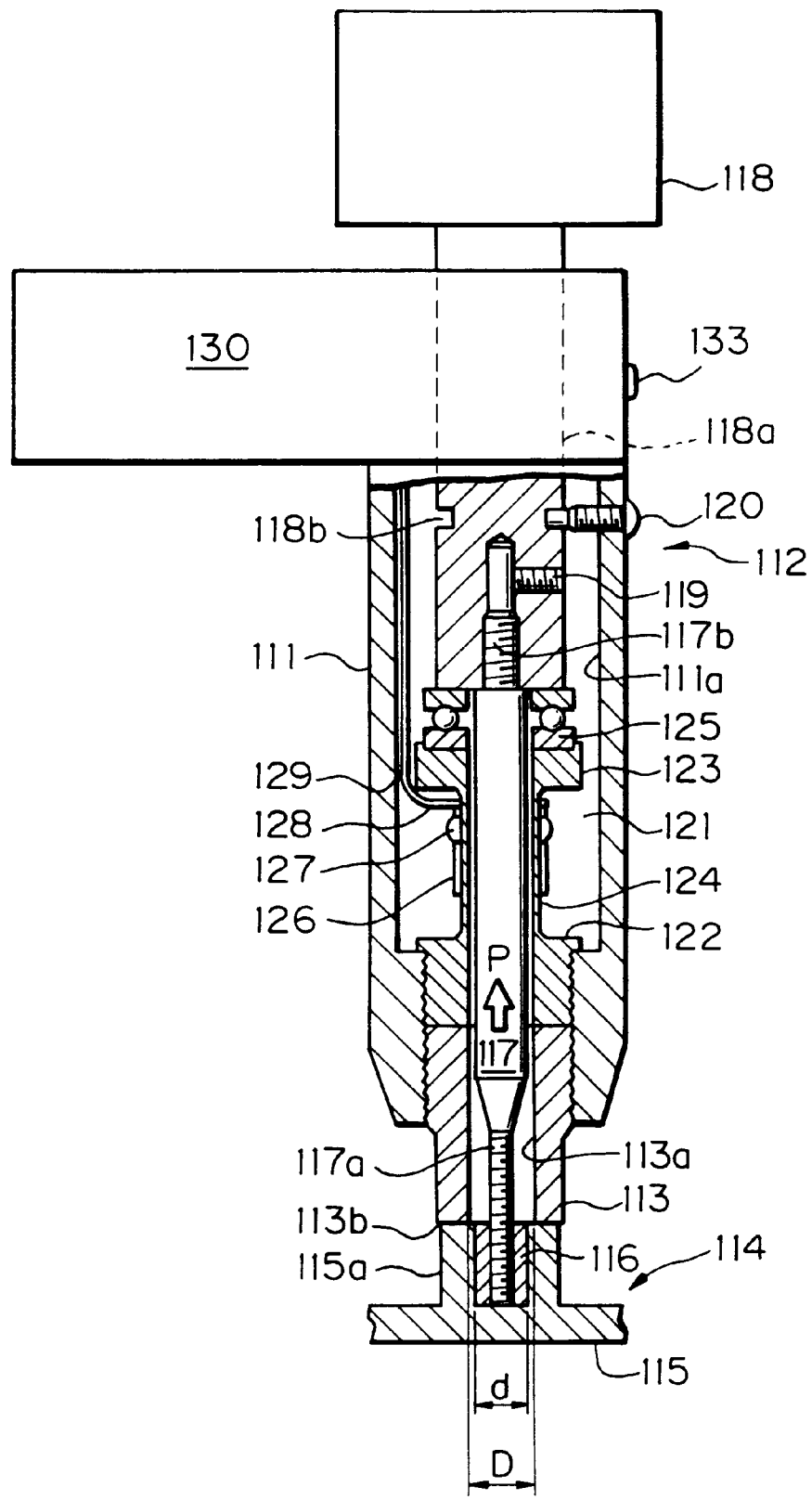
FIG. 2 is a sectional front view showing another conventional tensile strength tester.

FIG. 2 shows another conventional tensile strength tester which is small size and portable and capable of meeting the above demand. The tester to be described is taught in Japanese Patent Laid-Open Publication No. 3-125941 mentioned earlier. As shown, the tester, generally 112, includes a body 111 and a substantially hollow cylindrical seat attachment 113 fitted in the bottom of the body 111. An article 114 to be measured is made up of a base material 115 having a boss 115a and a screw member 116 formed in the boss 115a by insertion molding.

The seat attachment 113 is removably held in threaded engagement with the bottom portion of the drum 111. An axial bore 113a is formed throughout the seat attachment 113 and has an inside diameter D greater than the maximum outside diameter d of the screw member 116. At the time of measurement, a seat surface 113b forming the bottom of the seat attachment 113 rests on the top of the boss 115a around the screw member 116. A pull shaft 117 extends throughout the bore 113a of the seat attachment 113 coaxially with the attachment 113. One end of the pull shaft 117 is held in threaded engagement with a knob 118 mounted on the top of the body 111. The other end 117a of the pull shaft 117 is driven into the screw member 116 of the article 114.

Specifically, the end 117b of the pull shaft 117 is screwed into a boss 118a included in the knob 118. Then, the pull shaft 117 is fixed to the knob 118 by a screw 119. To replace the pull shaft 117, the screw 119 is loosened, and then the shaft 117 is pulled out from the knob 118.

A load transformer 121 has a first flange 122 at its bottom and a second flange 123 at its top. The first flange 122 is held in threaded engagement with the body 111 while the second flange 123 abuts against the boss 118a of the knob 118 via a thrust bearing 125. The flange 123 is mounted to the pull shaft 117 via the thrust bearing 125 and boss 118, so that a counterforce derived from a tensile force P generated in the pull shaft 117 acts on the flange 123 as a compressive force. A pressure sensing portion 124 is formed between and integrally with the flanges 122 and 123 and thin enough to elastically deform when subjected to the above compressive force. A strain gauge 126 is fitted on the pressure sensing portion 124 in order to measure the strain of the portion 124 subjected to the compressive force. Specifically, the two flanges 122 and 123 and pressure sensing portion 124 are implemented as a single hollow cylinder and held in threaded engagement with the body 111. The strain gauge 126 measures the tensile force P acting on the pull shaft 117 in terms of the strain (deformation) of the pressure sensing portion 124 in the direction of thrust.

However, the tester shown in FIG. 2 is not desirable in the handling aspect, as follows. The screw 119 and the end 117b of the pull shaft 117 become loose, and so do the boss 118a of the knob 118 and the end 117b of the shaft 117, resulting in play. The screw 119 becomes loose because the end of the pull shaft 117 against which the screw 119 abuts is thinner than the threaded engaging portion and reduces the contact area and because the shaft 117 is formed of a hard material for increasing strength. The end 117b becomes loose because it is turned in the reverse direction in the event of return after measurement and therefore subjected to resistance ascribable to, e.g., the biting of the screw portion. More specifically, while the friction of a seat surface usually acts against loosening, the seat surface of the above conventional tester is implemented by a ball bearing substantially free from friction and therefore does not act against loosening.

The boss 118a functions to transfer rotation and to receive a counterforce acting against a tensile force. The boss 118a transfers the counterforce to a ball bearing 125 at a position where the former contacts the latter and transfers a torque to the pull shaft 117. This is why the threaded engagement is essential.

Another problem with the tester shown in FIG. 2 is that the tester is too heavy to free the operator from fatigue and prevents the operator from taking a desired posture. Further, the screw 119 is surrounded by the body 111 while a screw 120 is received in a groove 118b in order to fix the body 111 in place. Therefore, when the pull shaft 117 should be replaced due to a change in the size or the diameter of the screw member 116, it is necessary to remove the screw 120 so as to remove the body 111 and then remove the screw 119. The screw 120 must be removed also when the screw 119 has a play. For these reasons, the tester of FIG. 2 is not easy to maintain or replace. In addition, when the pull shaft 117 is turned by hand via the knob 118, a great torque would render the movement of the shaft 117 and therefore measurement unstable due to, e.g., displacement. Therefore, the pull shaft 117 should preferably be automatically driven by a motor.

Preferred embodiments of the tensile strength tester in accordance with the present invention will be described hereinafter. First, embodiments allowing a torque to be applied by hand via a knob, i.e., manual tensile strength testers will be described.

Figure 3:
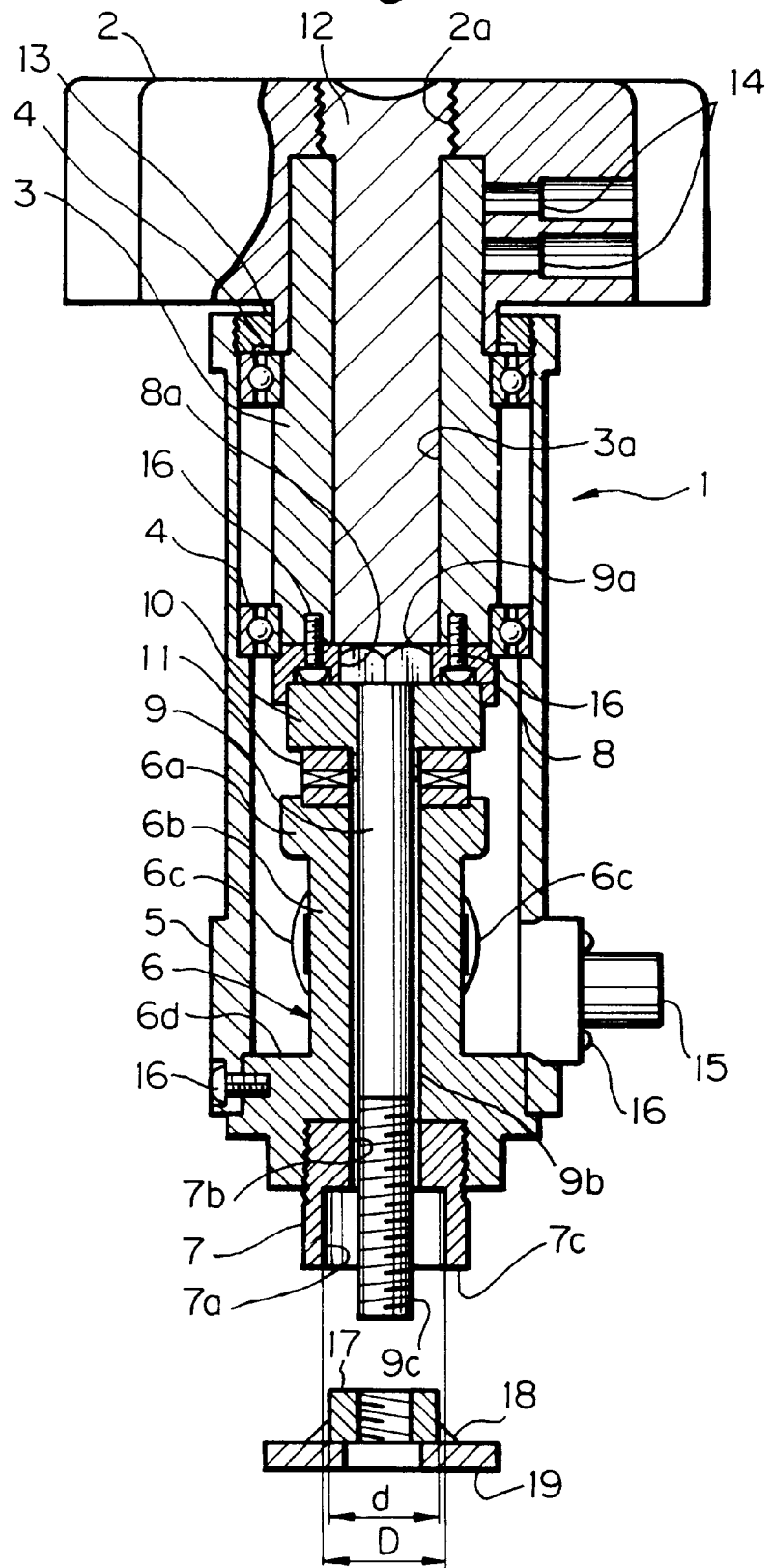
FIG. 3 is a sectional front view showing a first manual drive type embodiment of the tensile strength tester in accordance with the present invention.

Referring to FIG. 3, a first embodiment of the present invention using the manual drive scheme is shown and generally designated by the reference numeral 1. As shown, the tester 1 includes a knob 2. A sleeve or hollow drive shaft 3 is fixed to the knob 2 by setscrews 14. A casing 5 supports the sleeve 3 via radial bearings or single row, deep groove ball bearings 4. A compression type load transformer 6 is fixed to the lower end portion of the casing 5 by small screws 16 coaxially with the casing 5. A seat attachment 7 is removably held in threaded engagement with the bottom of the load transformer 6 coaxially with the casing 5. A drive plate 8 is fixed to the bottom of the sleeve 3 by small screws 16 and formed with a hexagonal hole 8a. A pull shaft 9 has a hexagonal head 9a received in the hexagonal hole 8a. A thrust bearing or needle-like roller bearing 11 rotatably supports the pull shaft 9 on the load transformer 6 via a base 10. A plug 12 is held in threaded engagement with a hole 2a formed at the center of the knob 2. The plug 12 is received in a hole 3a formed at the center of the sleeve 3 and abuts against the hexagonal head 9a of the pull shaft 9. An electric signal output from the load transformer 6 is fed out via a receptacle connector 15. An electric system 25 (see FIG. 4) is connected to the electrodes of the receptacle connector 15.

The tester 1 measures the tensile strength of a desired article 17. In the illustrative embodiment, the article 17 is assumed to be a screw member or nut 17 connected to a steel sheet 19 by welding 18.

The seat attachment 7 is formed with an axial bore 7a having an inside diameter D, and a hole 7b communicated to the bore 7a. The pull shaft 9 is loosely fitted in the hole 7b. The inside diameter D of the bore 7a is selected to be greater than the maximum outside diameter d of the screw member 17. When the tester 1 measures the tensile strength of the article 17, a seat surface 7c forming the bottom of the seat attachment 7 is placed on the the steel sheet 19 around the screw member 17. The attachment 7 therefore plays the role of a seat portion for allowing the tester 1 to be seated on the the steel sheet 19 and to support the sheet 19. Various kinds of seat attachments 7 each having a particular inside diameter are prepared. This, coupled with the fact that the seat attachment 7 is removably mounted to the load transformer 6, allows the attachment 7 to be easily replaced with another seat attachment matching with the maximum diameter of the screw member 17. Further, because the seat attachment 7 is screwed into the load transformer 6, the former can be protruded from the latter to any desired position.

The pull shaft 9 is passed through the hole 7b of the seat attachment 7 coaxially with the attachment 7 and includes a shank 9b and the previously mentioned hexagonal head 9a greater in diameter than the shank 9b. The shank 9b has a threaded portion 9c at its end. When the threaded portion 9c is driven into the screw member 17, a torque applied to the drive plate 8 is transferred to the pull shaft 9 via the head 9a received in the hexagonal hole 8a of the drive plate 8.

The sleeve 3 to which the drive plate 8 is fixed is rotatably supported via the upper and lower ball bearings 4. A seal ring 13 is mounted on the upper ball bearing 4 in order to intercept impurities. The hole 3a of the sleeve 3 has a diameter greater than the maximum outside diameter of the hexagonal head 9a of the pull shaft 9, so that the shaft 9a can be pulled out of the hole 3a.

When the knob 2 is turned by hand, the rotation of the knob 2 is transferred to the sleeve 3 fixed to the knob 2 by the setscrews 14. The rotation of the sleeve 3 is transferred to the pull shaft 9 via the drive plate 8. As a result, the pull shaft 9 exerts a tensile force corresponding its rotation angle on the nut 17 via the hexagonal head 9a, base 10, roller bearing 11, load transformer 6 and seat attachment 7 while exerting a counterforce on the steel sheet 19.

Various kinds of pull shafts 9 each having a threaded portion 9c of particular diameter are also prepared. Only if the plug 12 is removed from the knob 2, the pull shaft 9 can be pulled out of the hole 3a of the sleeve 3. Therefore, the pull shaft 9 can be easily replaced with another pull shaft matching with the diameter of the nut 17.

The roller bearing 11 mounted on the top of the load transformer 6 as a thrust bearing is highly durable even when subjected to a heavy load. The roller bearing 11 may be replaced with a ball bearing if the tester 1 is free from heavy loads. Further, use may be made of a tapered roller bearing.

The base 10 intervening between the thrust bearing 11 and the head 9a of the pull shaft 9 has a preselected substantial thickness. When the diameter of the head 9a is smaller than the maximum outside diameter of the thrust bearing 11, i.e., when the contact area between the head 9a and the bearing 11 is relatively small, the base 10 prevents a local load from acting on the bearing 11. Specifically, the thick base 10 implements the propagation of a stress at 45 degrees and thereby causes a load to act evenly on the thrust bearing 11. The base 10 therefore allows the head 9a to be reduced in size, enhancing a small size, light weight configuration.

The casing 5 constituting the body of the tester 1 is a hollow cylinder having a suitable diameter which can be held by one hand.

Figure 4:
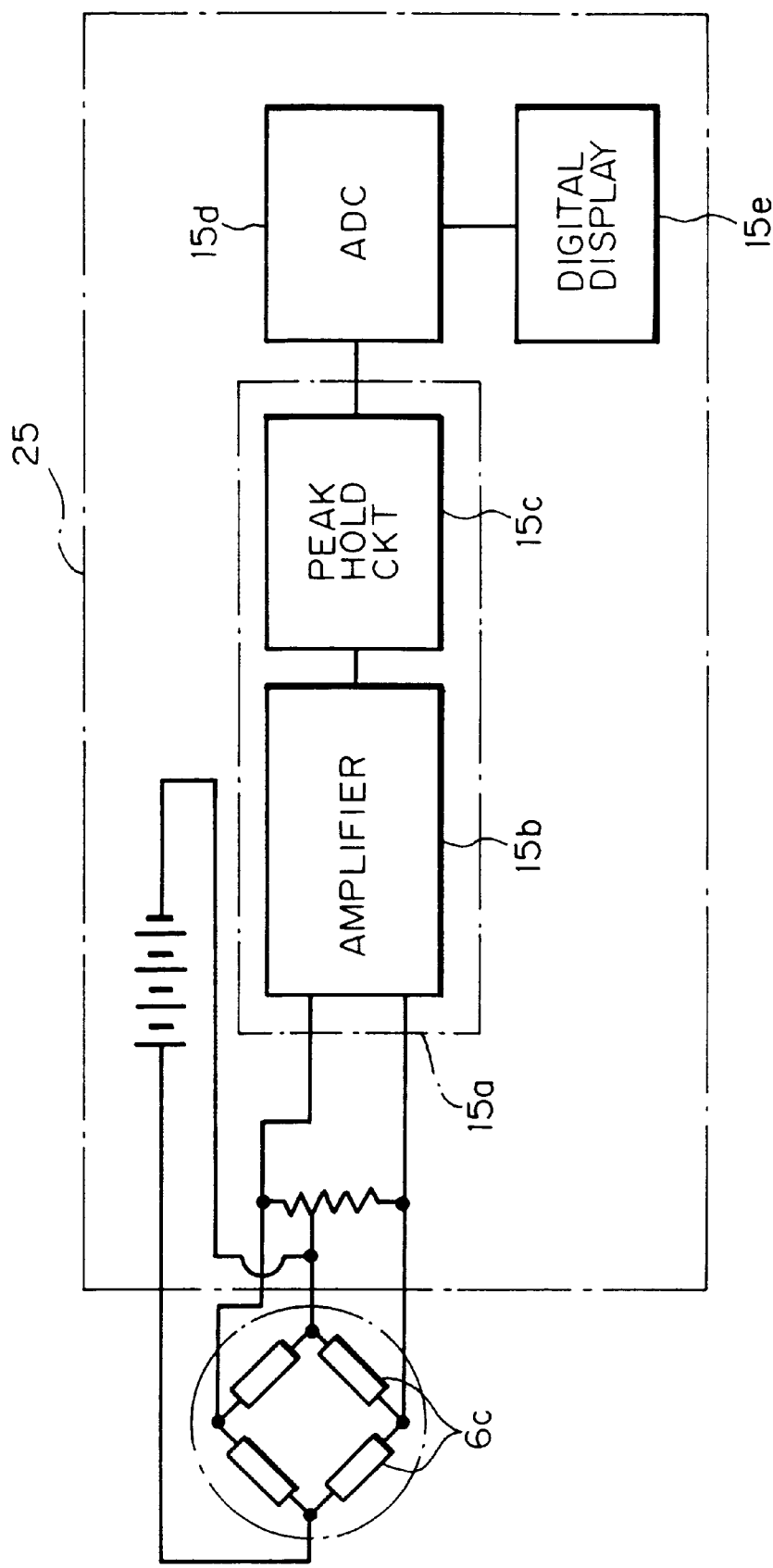
FIG. 4 is a block diagram schematically showing an electric system particular to the first embodiment.

The load transformer 6 is fixed to the bottom of the casing 5 and made up of a first flange 6d, a second flange 6a, a pressure sensing portion 6b intervening between the two flanges 6d and 6a, and four strain gauges 6c fitted on the circumference of the pressure sensing portion 6b at equally spaced locations. The first or lower flange 6d is fixed to the casing 5 by a small screw 16. The second or upper flange 6a abuts against the underside of the head 9a of the pull shaft 9 via the thrust bearing 11 and base 10. In this configuration, the load transformer 6 receives, as a compressive force, a counterforce derived from a tensile force generated in the shaft 9. The pressure sensing portion 6b is thin enough to elastically deform when subjected to the above compressive force. The strain gauges 6c measure the strain of the pressure sensing portion 6b when the compressive force acts on the portion 6b. As shown in FIG. 4, the strain gauges 6c are implemented as a bridge circuit and transform the strain to an electric signal for the measurement of the load. The thin configuration of the portion 6b not only enhances sensitivity, but also implements a space for arranging the strain gauges 6c.

The thin pressure sensing portion 6b intervening between the first and second flanges 6d and 6a constitutes a part of the casing 5. The strain gauges 6c fitted on the pressure sensing portion 6b measure a tensile force acting on the pull shaft 9 in terms of a strain (deformation) in the direction of thrust.

In the illustrative embodiment, the receptacle connector 15 is located in the vicinity of the strain sensors 6c. This successfully reduces the wiring length of the tester 1.

Referring to FIG. 4, the electric system 25 of the illustrative embodiment will be described. As shown, when the pressure sensing portion 6b elastically deforms due to the compressive force, the strain gauges 6c produce an electric signal proportional to the strain rate of the portion 6b. The electric signal is input to the electric system 25 via intermediate terminals and wirings each having a shield structure. A controller 15a includes a microcomputer, not shown, an amplifier 15b, and a peak hold circuit 15c. There are also shown in FIG. 4 an analog-to-digital converter (ADC) 15d and a digital display 15e. The electric signal output from the strain gauges 6c is amplified and digitized and has its peak held. As a result, a peak value constantly appears on the digital display 15e.

Before the operation of the above tester 1, the pull shaft 9 whose threaded portion 9c corresponds in diameter to the nut 17 is mounted to the tester 1. Specifically, after the plug 12 has been removed from the knob 2, the pull shaft 9 is inserted into the hole 3a of the sleeve 3. After the head 9a of the pull shaft 9 has been received in the hexagonal hole 8a of the drive plate 8, the plug 12 is driven into the knob 2 until the end of the plug 12 abuts against the head 9a. In this condition, the pull shaft 9 is prevented from moving in the axial direction.

For measurement, the seat surface 7c of the seat attachment 7 is caused to rest on the steel sheet 19, and then the knob 2 is turned by hand in order to drive the threaded portion 9c of the pull shaft 9 into the nut 17. As the knob 2 is further turned, the rotation angle of the pull shaft 9 sequentially increases from the rotation angle at which the seat attachment 7 has abutted against the steel sheet 19. As a result, a force tending to pull the nut 17 out of the steel sheet 19 and proportional to the above rotation angle acts on the nut 17 due to the threaded engagement of the threaded portion 9c and nut 17. Because the seat attachment 7 fixed to the load transformer 6 has an inside diameter greater than the maximum diameter of the nut 17 and because the pull shaft 9 is coaxial with the attachment 7, the seat surface 7c automatically closely contacts the steel sheet 9 around the nut 17. The seat surface 7a therefore bears the counterforce of the pull shaft 9 via the load transformer 6, thrust bearing 11, base 10, and head 9a. The counterforce acting against the tensile force generated in the pull shaft 9 is transferred to the second flange 6d of the load transformer in the direction opposite to the above direction. Consequently, a compressive force equal, but opposite in direction, to the force pulling the nut 17 acts on the pressure sensing portion 6b. At this instant, the thrust bearing 11 serves to reduce the rotation load of the knob 2.

The tensile force generated in the pull shaft 9 compresses the pressure sensing portion 6b of the load transformer 6 in the axial direction. As a result, an electric signal proportional to the tensile force acting on the nut 17 is sent from the strain gauges 6c to the electric system 25 via the intermediate terminals and wirings. The amplifier 15b amplifies the electric signal while the ADC 15d digitizes the amplified electric signal. The resulting digital value appears on the display 15e and allows the tensile force pulling the nut 17 to be read.

As the knob 2 is further turned, the force tending to pull out the nut 17 finally overcomes the force binding the steel sheet 19 and nut 17 to each other and causes the nut 17 to begin to leave the steel sheet 19. At this instant, the tensile force P reaches its maximum value and is read on the display 15e. The tester 1 therefore allows the tensile strength of the article to be measured at the cite immediately. If desired, a lubrication film implemented by oily Teflon or liquid Teflon may be formed between the threaded portion 9c of the pull shaft 9 and the nut 17 in order to generate a great tensile force P with a weak force for turning the knob 2. This will extend the life of the pull shaft 9 to be repeatedly used.

The tester 1 can adapt itself to the configuration and dimensions of the nut or screw member 17 only if the seat attachment 7 and pull shaft 9 are replaced with adequate ones, i.e., without resorting to the replacement of the knob 2. The tester 1 is therefore miniature and portable and makes it needless to cut out the nut portion from the steel sheet 19. Such a tester 1 can be used to measure a tensile strength at a cite.

The pressure sensing portion 6b is implemented as a thin elastically deformable portion. This, coupled with the strain gauges 6c responsive to the deformation of the portion 6b, simplifies the construction and reduces the size of the tester 1. Moreover, because the wirings connecting the load transformer 6 to the electric system 25 are provided with a shield structure and arranged within the casing 5, the tester 1 is highly resistive to noise and prevents the wirings from being cut off during measurement. Consequently, not only reliable measurement but also easy operation are promoted.

Figure 5:
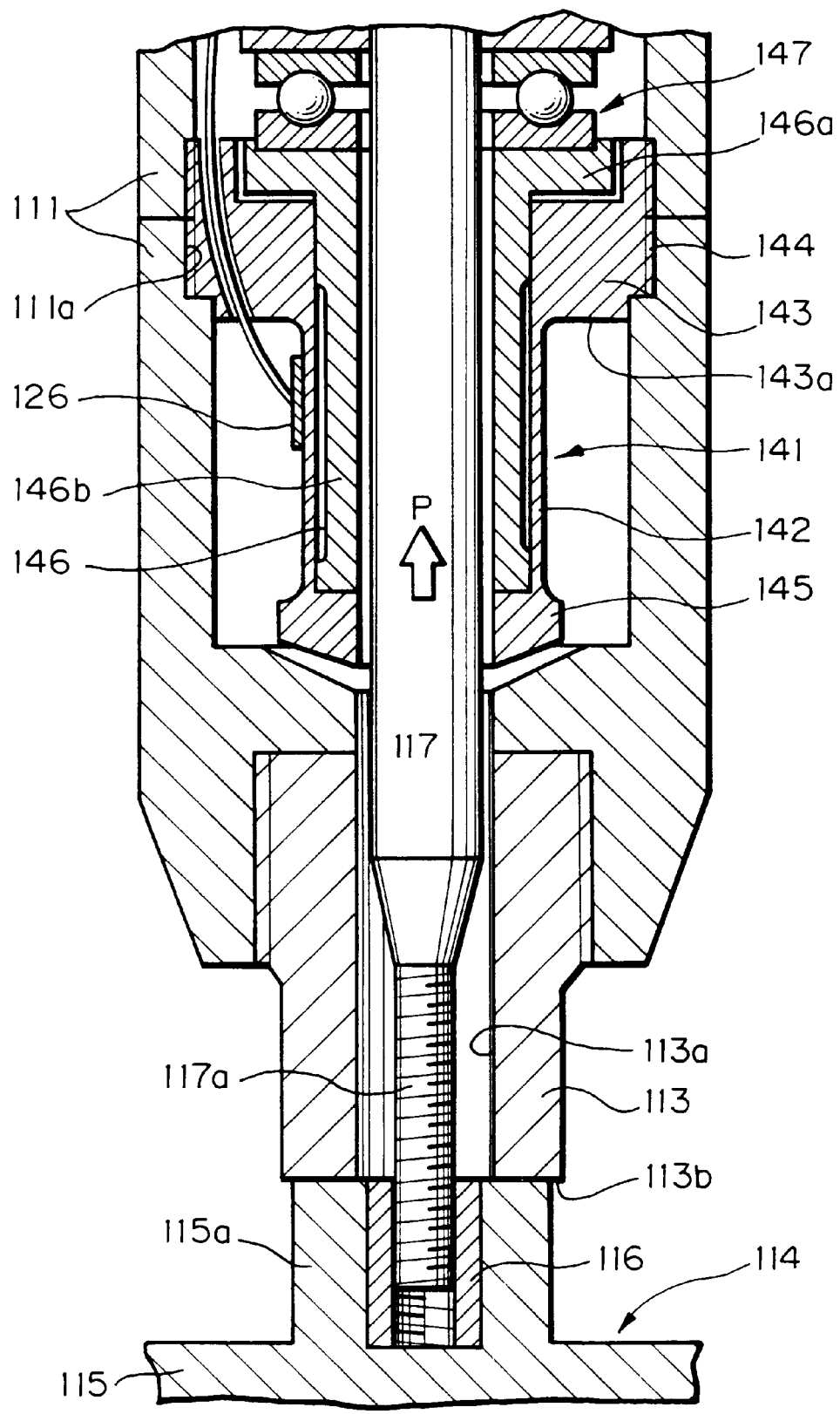
FIG. 5 is a sectional front view showing a modification of a load transformer included in the first embodiment.

FIG. 5 shows a modification of the above embodiment including a hollow cylindrical tension type load transformer 141. As shown, the load transformer 141 includes an intermediate portion 142 forming a thin portion and strain gauges 126 responsive to the strain (deformation) of the intermediate portion 142 in the direction of thrust. One end of the load transformer 141 is fixed to the upper portion of a casing 111 by a thread 144 via a first flange 143 formed integrally with the intermediate portion 142. To allow the first flange 143 to be smoothly engaged with the inner periphery 111a of the casing 111, the flange 143 is formed with a stepped portion 143a coaxial with the casing 111. When the flange 143 is fixed to the casing 111, the load transformer 141 is automatically positioned coaxially with a pull shaft 117. A second flange 145 is formed at the other end of the load transformer 141 and contiguous with the intermediate portion 142. A hollow cylindrical transfer shaft 146 is coaxially received in the load transformer 141 and abuts against the upper end of the second flange 145 at its lower end. The pull shaft 117 is passed through the transfer shaft 146, as illustrated.

Figure 6:
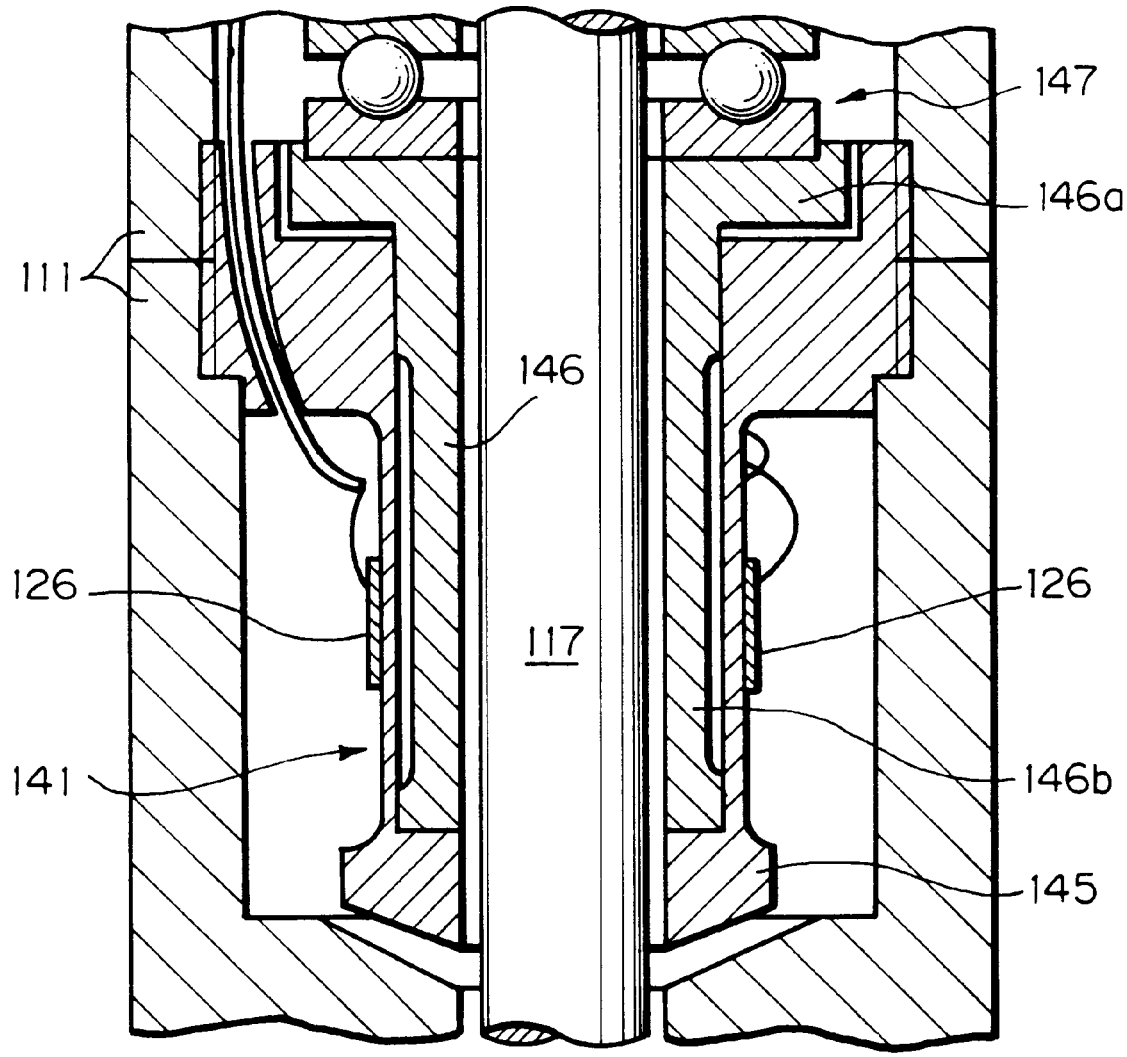
FIG. 6 is a section showing a modification of a transfer shaft included in the load transformer.

In the above modification, the lower end of the transfer shaft 146 abuts against the upper end of the second flange 145, as stated above. Alternatively, as shown in FIG. 6, the lower end of the transfer shaft 146 may be screwed into the second flange 145. The crux is that the transfer shaft 146 be coaxial with the load transformer 141.

The transfer shaft 146 is formed with a flange 146a at its upper end. The hollow cylindrical portion 146b of the transfer shaft 146 has a height greater than the inside depth of the load transformer, so that a gap of preselected dimension is formed between the flange 146a and the flange 143. A detent pin, for example, may be studded on the flange 143 and engaged with the flange 146a in order to prevent the transfer shaft 146 from following the rotation of the pull shaft 117.

A thrust bearing 147 is positioned between the flange 146a of the transfer shaft 146 and a knob 118. The transfer shaft 146 and thrust bearing 147 are fixed to the casing 111 while being positioned by, e.g., a stop ring not shown. The stop ring prevents the transfer shaft 146 and thrust bearing 147 from slipping out of the casing 111 and insures the smooth rotation of the bearing 147. In this manner, the flanges 143 and 145 and intermediate portion 142 of the load transformer 141 are fixed to the casing 111 together, and the portion 142 forms a thin portion constituting a part of the casing 111.

In operation, after a seat surface 113b included in a seat attachment 113 has been seated on a screw portion 116 around the boss 115a of a base material 115, the knob 118 is turned by hand. The rotation of the knob 118 is transferred to the pull shaft 117. When a threaded portion 117a included in the pull shaft 117 is driven into the screw member 116, a force P tending to pull the screw member 116 upward, as viewed in FIG. 5, out of the base material 115 acts on the screw member 116. A counterforce acting against the tensile force P is transferred to the second flange 145 of the load transformer 141 via the pull shaft 117, thrust bearing 147 and transfer shaft 146. As a result, a tensile force equal to the above force P acts on the intermediate portion 142 because the first flange 143 is fixed to the casing 111. The pull shaft 117 is rotated by such a force. When the force P corresponding to the rotation angle θ of the shaft pull 117 acts on the screw member 116, the intermediate portion 142 is deformed by the tensile force equal to the force P. Consequently, the strain gauges 126 fitted on the outer periphery of the intermediate portion 142 deform and send an electric signal proportional to the force P to the electric system 25 shown in FIG. 4. As for the rest of the construction and operation, the modification is identical with the previous embodiment.

Referring again to FIG. 3, the plug 12 inserted in the hole 3a of the sleeve 3 is held in threaded engagement with the knob 2 in order to prevent the pull shaft 9 from slipping out upward. The seat attachment 7 has an inside diameter greater than the maximum outside diameter of the nut 17 is held in threaded engagement with the end of the load transformer 6 which bears the pulling force or separating force via the thrust bearing 11. The attachment 7 can therefore be easily replaced in accordance with the diameter of the nut 17. The sleeve 3 is supported by the ball bearing 4 coaxially with the casing 5 in such a manner as to be rotatable, but not movable in the axial direction.

The above embodiment prevents the pull shaft 9 from being loosened and allows it to be replaced easily and rapidly when the diameter of the article to be tested is changed or when the shaft 9 wears or is broken or otherwise damaged. It is to be noted that the nut 17 is representative of various kinds of screw members, including nuts and bolts, connected to iron and other metal sheets and ABS and other plastic sheets by burying, press fitting, molding and other technologies. This is also true with various embodiments to be described hereinafter.

Figure 7:
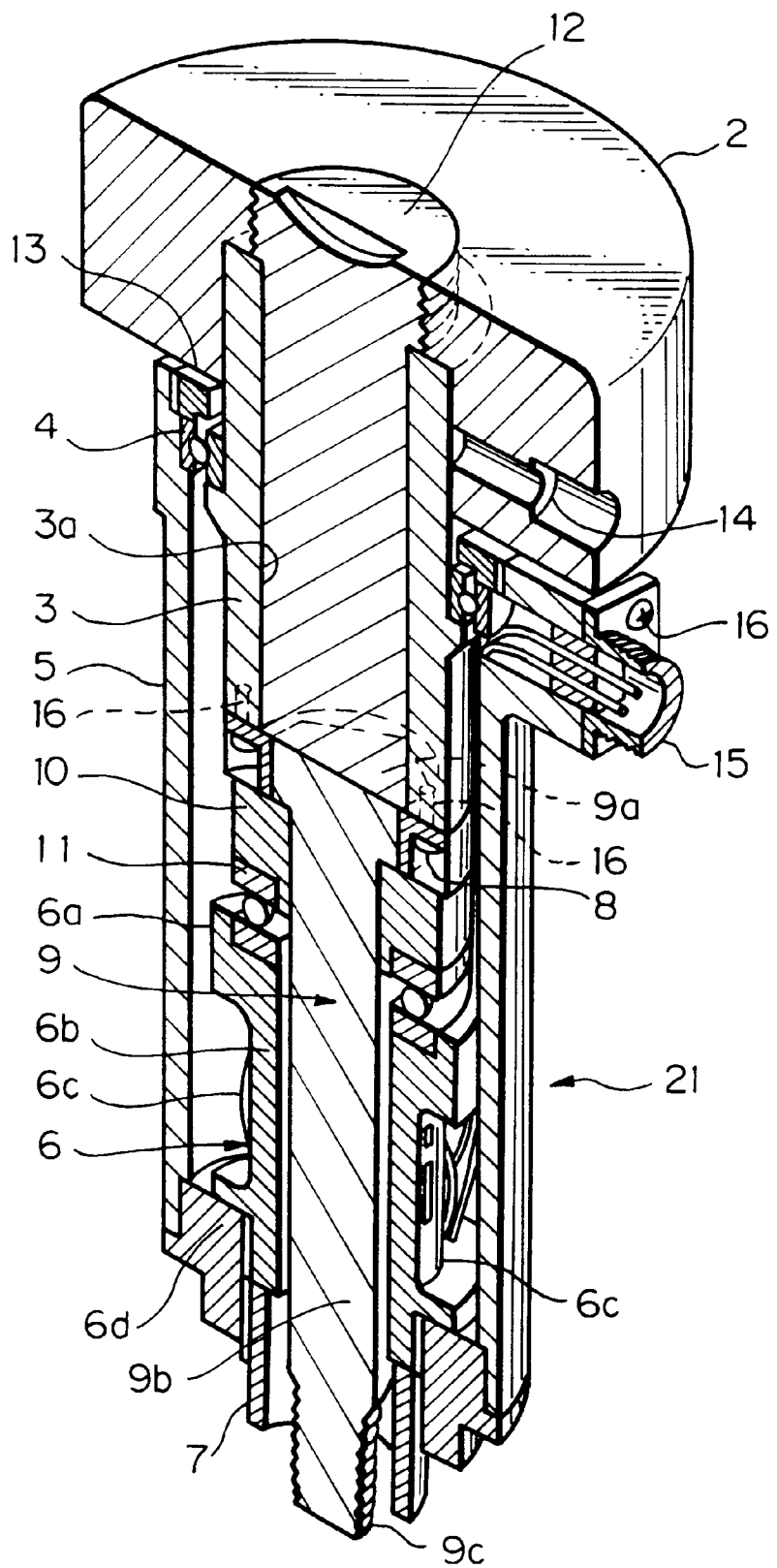
FIG. 7 is a sectional perspective view showing a second manual drive type embodiment of the tensile strength tester in accordance with the present invention in a plane containing the axis of the tester.

FIG. 7 shows a second manual drive type embodiment of the tensile strength tester in accordance with the present invention. As shown, a tensile strength tester, labeled 21, is identical with the tensile strength tester 1 except that the receptacle connector 15 is located in the vicinity of the knob 2. This configuration is advantageous in that when the screw member 17 is positioned in a narrow space, e.g., in a deep hole, the receptacle connector 15 does not obstruct the insertion of the pull shaft 9. The tester 21 can therefore measure even a portion whose diameter is close to the diameter of the casing 5.

In the first embodiment, the drive plate 8 with the hexagonal hole 8a mating with the hexagonal head 9a of the pull shaft 9 is fixed to the end of the sleeve 3 by the screws 16. Alternatively, the sleeve 3 may be provided with a bottom and have a hole (hexagonal hole) formed in the bottom. Of course, the hole may be provided with a configuration other than rectangle so long as it is capable of exerting a rotating force.

Figure 8A:
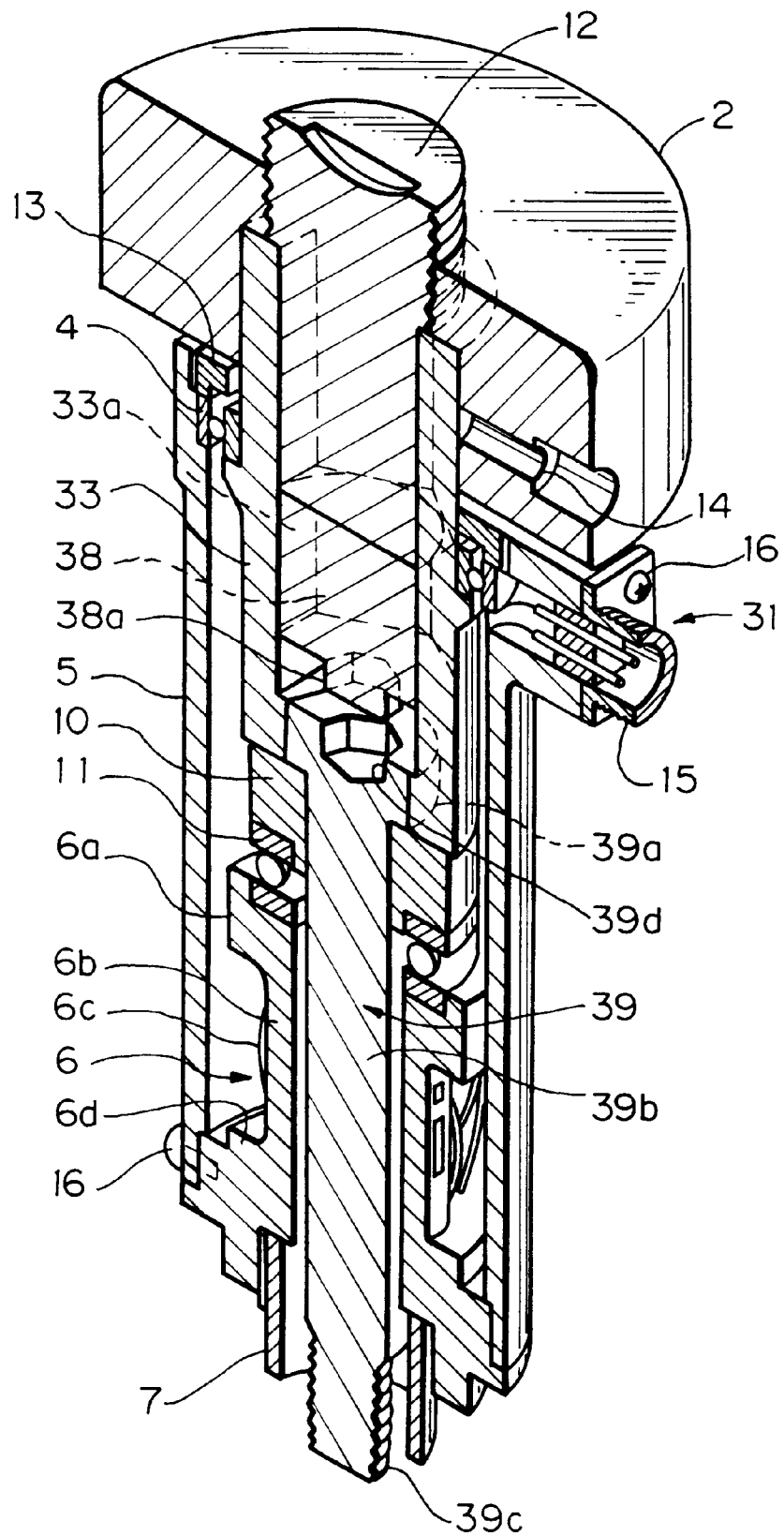
FIG. 8A is a sectional plan view showing a third manual drive type embodiment of the tensile strength tester in accordance with the present invention in a plane containing the axis of the tester.

FIGS. 8A–8C show a third manual drive type embodiment of the present invention while FIGS. 9A and 9B show a fourth manual drive type embodiment of the present invention. As shown, the third embodiment includes a pull shaft 39 implemented by a bolt having a head 39a formed with a hexagonal hole 39d and a threaded portion 39c at the end opposite to the head 39a. In this case, a hexagonal rod 38 having a projection 38c capable of mating with the hole 39d is positioned at the center of the end of a sleeve 33. Again, the hole 39d is not limited to a hexagonal hole. For example, as shown in FIG. 9C, use may be made of a pull shaft 49 having a head 49a formed with a groove 49d and a threaded portion 49c, and a projection, not shown, formed on the sleeve 33 and mating with the groove 49d. Further, as shown in FIGS. 9A and 9B, the head 49a of the pull shaft 49 may be implemented as a partly removed circle, in which case the drive plate 48 will be formed with a recess mating with such a circle. These configurations each prevents the pull shaft 49 from loosening, facilitates the replacement of the shaft 49, and allows the rotating force to be easily applied to the shaft 49.

Figure 10:
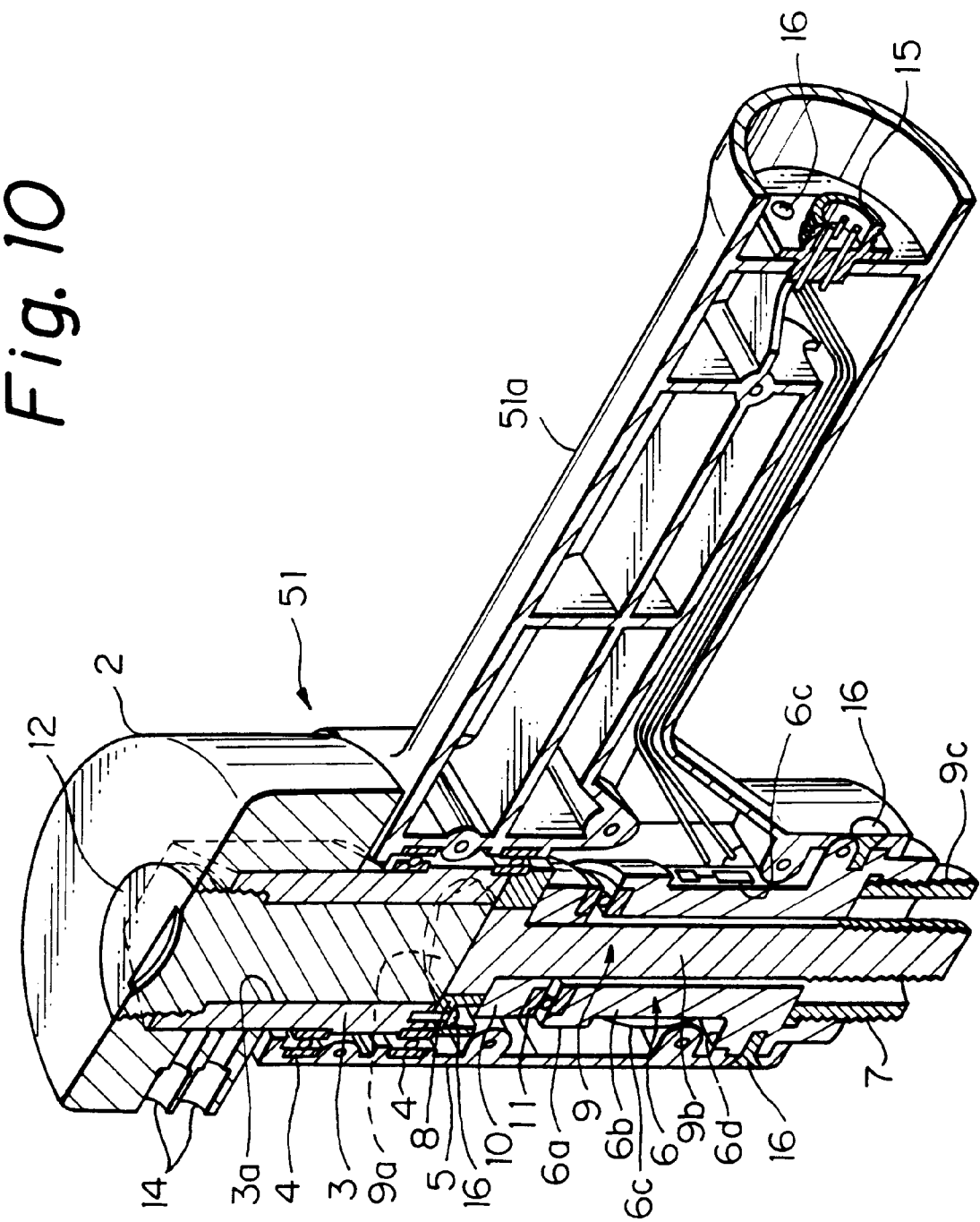
FIG. 10 is a sectional perspective view showing a fifth manual drive type embodiment of the tensile strength tester in accordance with the present invention in a plane containing the axis of the tester.

A fifth manual drive type embodiment of the present invention is shown in FIG. 10. As shown, a tensile strength tester, generally 51, includes a grip 51a extending out from the casing 5 in the radial direction. The wirings are arranged within the grip 51a while the receptacle connector 15 is arranged on the radially outermost end of the grip 51a. During measurement, the tester 51 has its grip 51a held by hand. This embodiment is easier to operate and allows a heavier load to be applied than the previous embodiments.

Figure 11:
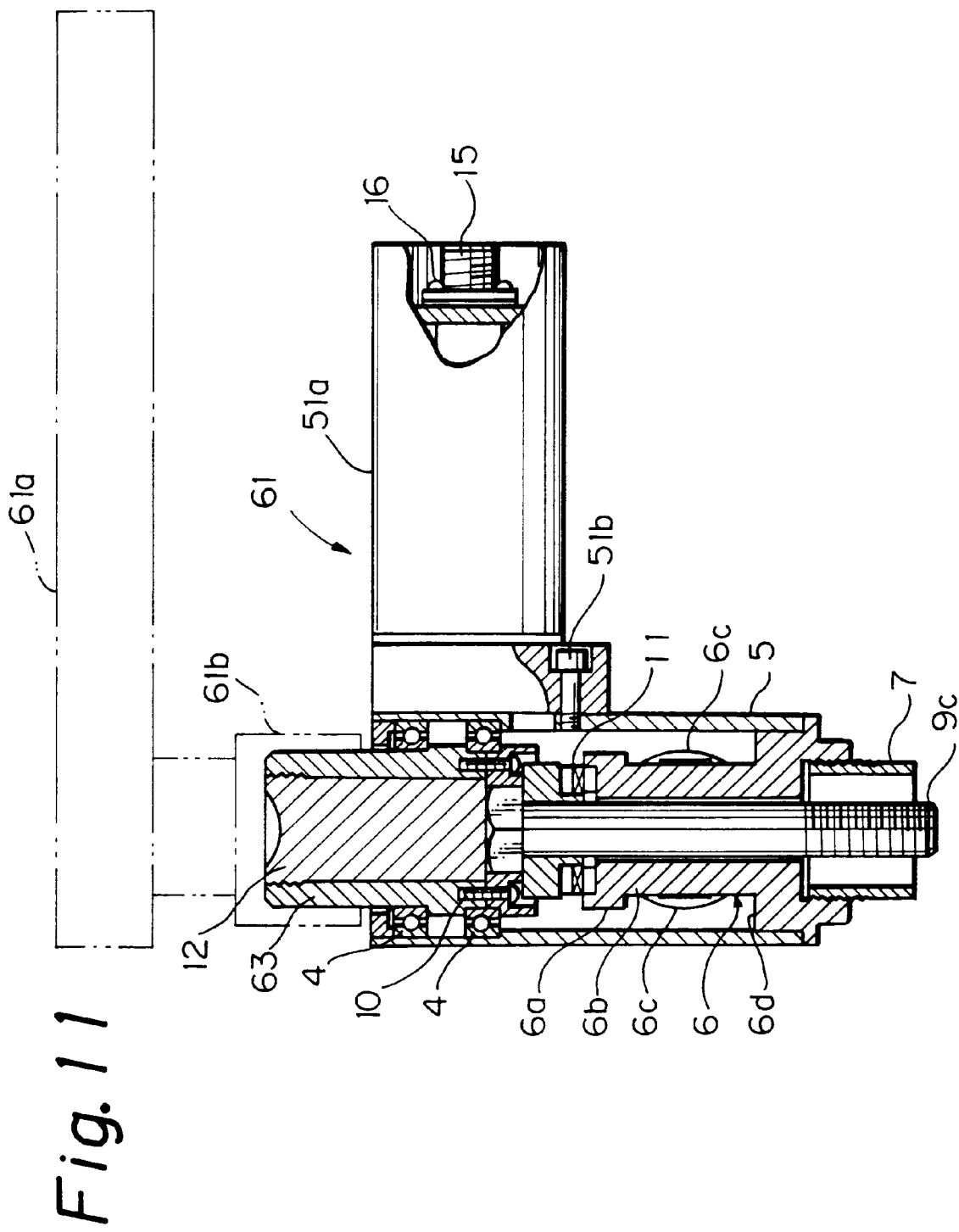
FIG. 11 is a sectional front view showing a sixth manual drive type embodiment of the tensile strength tester in accordance with the present invention.
Figure 12:
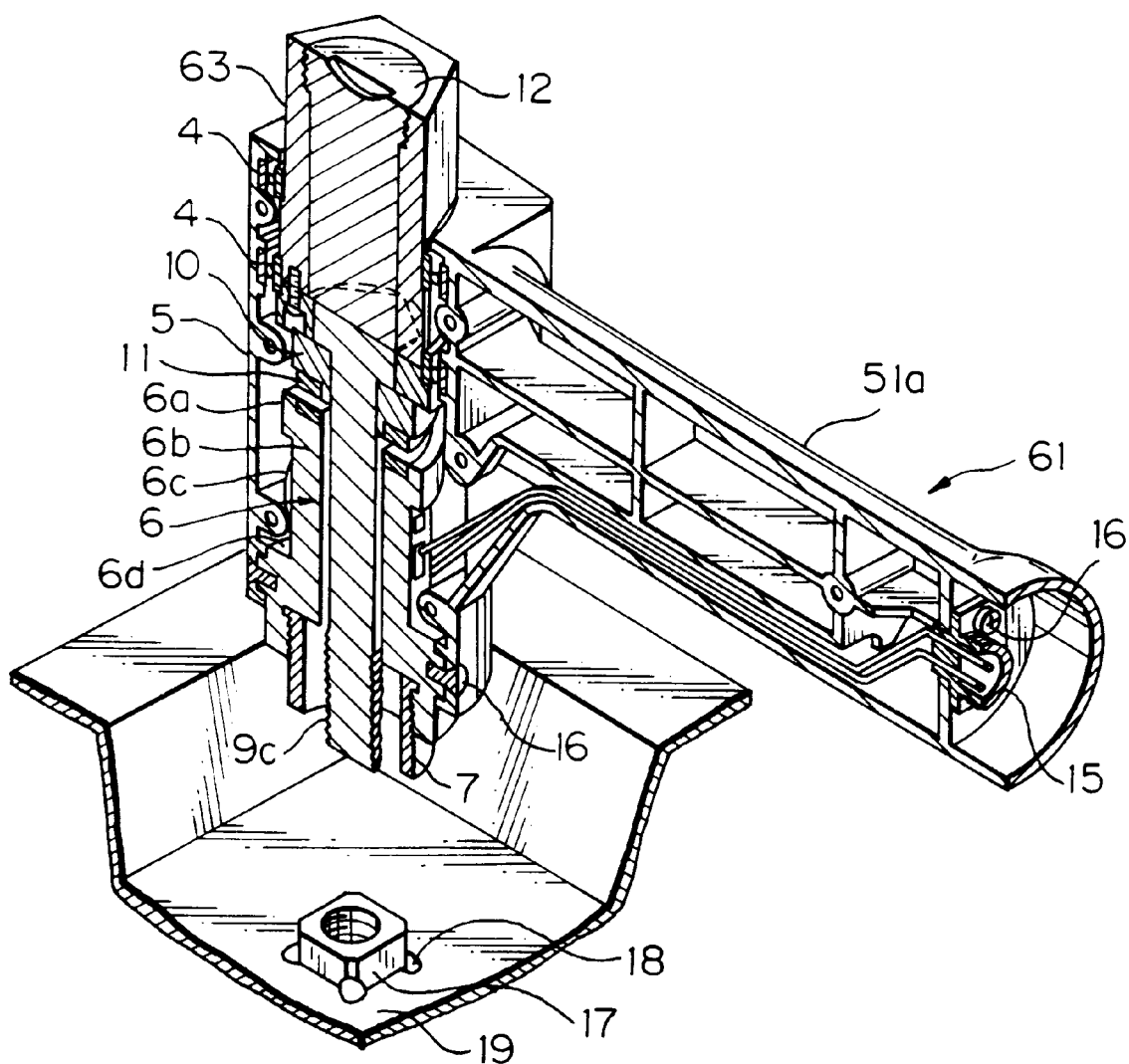
FIG. 12 is a sectional perspective view showing the sixth embodiment without a ratchet handle in a plane containing the axis of the tester.
Figure 13:
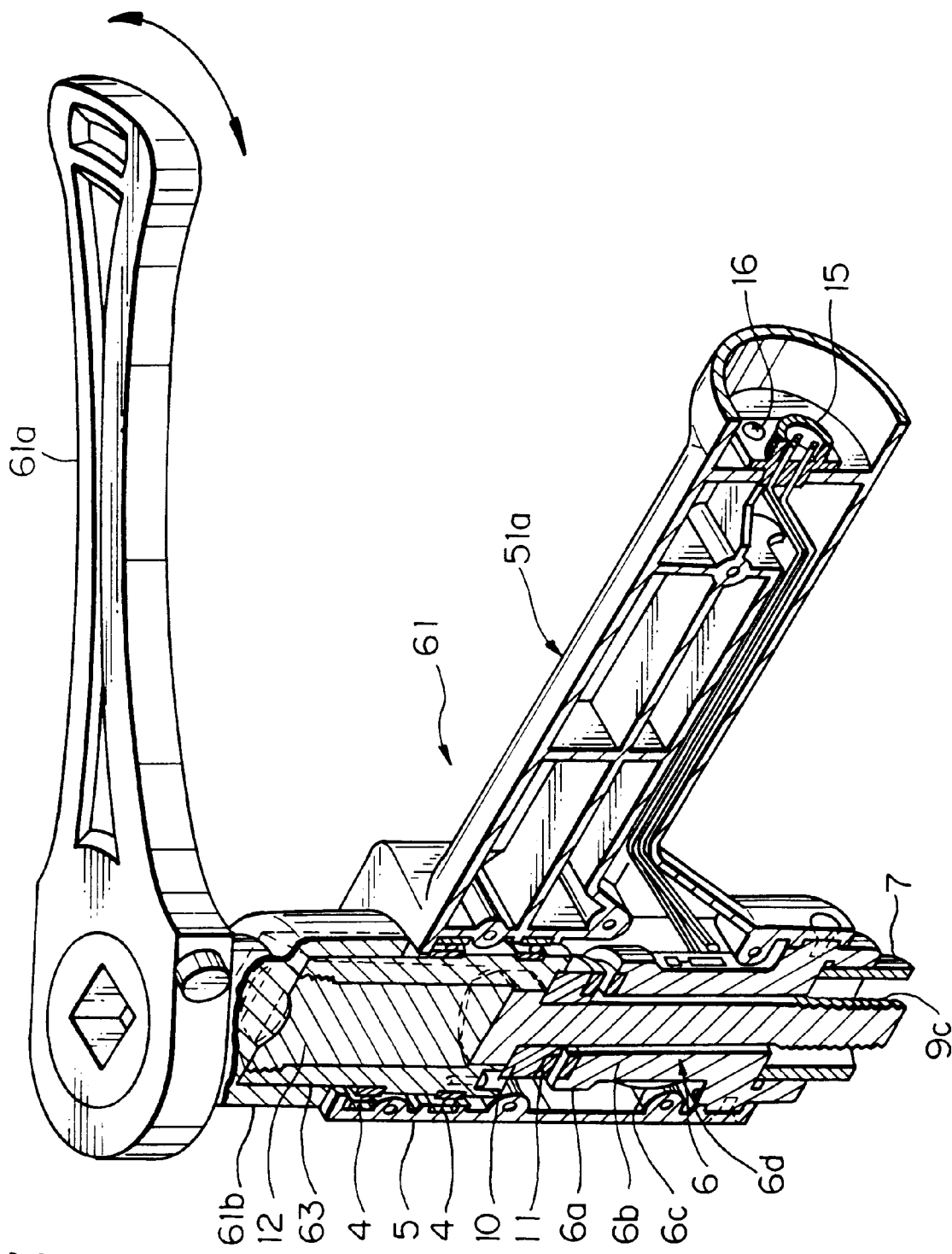
FIG. 13 is a view similar to FIG. 12, showing the sixth embodiment with the ratchet handle.

FIGS. 11–13 show a sixth embodiment of the present invention using the manual drive scheme. FIG. 12 shows a tensile strength tester, generally 61, without a ratchet handle 61a while FIG. 13 shows the tester 61 with the ratchet handle 61a. The tester 61, like the tester 1 of FIG. 3, includes the strain gauges 6c fitted on a member supporting the pull shaft 9 via the thrust bearing 4, so that the compressive force counteracting the tensile force is detected and output in the form of a voltage. Alternatively, a displacement gauge, for example, may be used to measure the elastic deformation of the head of the pull shaft 9. A sleeve 63 has a hexagonal hole at its end in order to drive the pull shaft 9 with the hexagonal hole mating with the hexagonal head 9a of the shaft 9. The sleeve 63 is so sized as to allow the pull shaft 9 to be freely passed therethrough.

As shown in FIG. 11, the drive plate 8 having the hexagonal hole mating with the hexagonal head 9a is fixed to the end of a sleeve 63 by screws, as in the first embodiment. Alternatively, the sleeve 63 may be provided with a bottom and have a drive hole (hexagonal hole) formed in the bottom. Again, the drive hole is not limited to a hexagonal hole. When the pull shaft 9 is implemented by a bolt with a hexagonal hole, a hexagonal rod capable of mating with the hexagonal hole should only be positioned at the center of the end of the sleeve 63. Such a configuration also prevents the pull shaft 9 from loosening, facilitates the replacement of the shaft 9, and allows the rotating force to be easily applied to the shaft 9.

The plug 12 is screwed into the bore of the sleeve 63 in order to prevent the pull shaft 9 from slipping out, as in the first embodiment. The seat attachment 7 including a sleeve whose inside diameter is greater than the maximum outside diameter of the nut or similar article is held in threaded engagement with the other end of the member 6 which bears the pulling force or separating force via the thrust bearing 11. Therefore, the sleeve of the seat attachment 7 can be easily replaced. The sleeve 63 is supported by the casing 5 via a ball bearing in such a manner as to be rotatable, but not axially movable, as in the first embodiment.

The end of the sleeve 63 on which the ratchet handle 61a is mounted is shown as having a hexagonal section by way of example. The crux is that the above end of the sleeve 63 be engageable with the ratchet handle 61a and capable of transferring a rotating force. When a one-way bearing is provided at the center of rotation of the ratchet handle 61a, the end of the sleeve 63 may even be circular.

The grip 51a supports the casing 5 of the tester 61 while the ratchet handle 61a exerts a rotating force, so that a great rotating force may be applied. In this configuration, a pulling force or separating force as great as 1 ton to 2 tons can be easily generated.

The embodiments shown and described each is usable to measure even the tensile force of a nut formed by the insertion molding of resin, a pressed nut, or a welded nut. Further the applicable range of the illustrative embodiment includes bearings press fitted in gears and sprockets.

Figure 14:
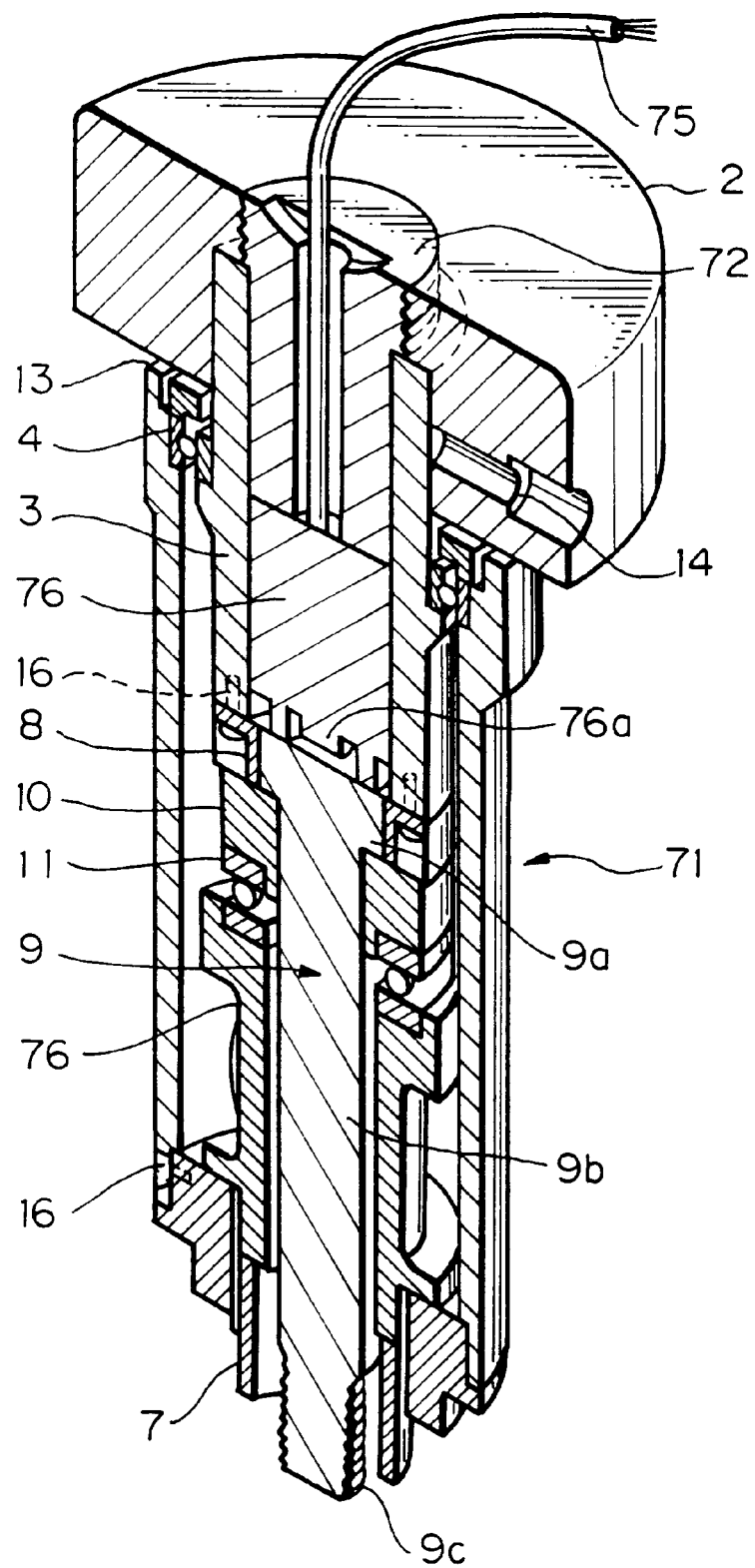
FIG. 14 is a sectional perspective view showing a seventh manual drive type embodiment of the tensile strength tester in accordance with the present invention in a plane containing the axis of the tester.

In each of the previous embodiments, the strain gauges are fitted on the member supporting the pull shaft via a thrust bearing, so that the compressive force counteracting the pulling force is detected and output in the form of a voltage. FIG. 14 shows a tensile strength tester 71 representative of a seventh manual drive type embodiment of the present invention. As shown, the tester 71 detects the elastic deformation of the head 9a of the pull shaft 9 with, e.g., a displacement gauge implemented by an eddy current displacement sensor. The principle of the eddy current displacement sensor is as follows. When iron or similar metal is placed in a high frequency magnetic field, an eddy current flows on the surface of the metal due to electromagnetic induction in accordance with the magnetic field and distance. The eddy current forms a magnetic field opposite in direction to the magnetic field which generated the eddy current (Lenz's law). Therefore, when iron or similar metal approaches the high frequency magnetic field, it weakens the magnetic field. It follows that by measuring the degree to which the original magnetic field is weakened, it is possible to determine a distance between the metal and the sensor.

Embodiments of the present invention using a motor drive scheme, as distinguished from the manual drive scheme, will be described hereinafter.

Figure 15:
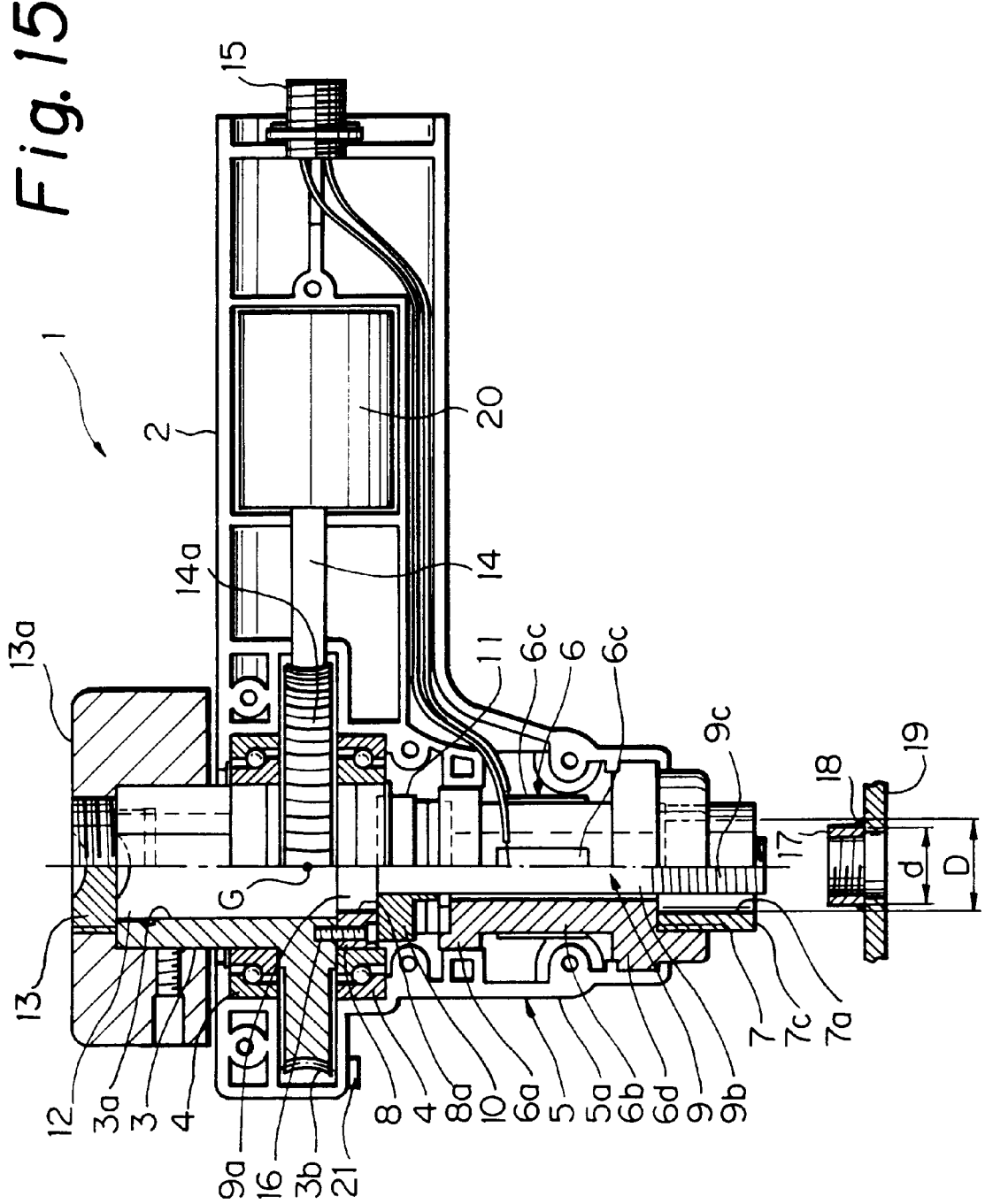
FIG. 15 is a sectional front view showing a first motor drive type embodiment of the tensile strength tester in accordance with the present invention.
Figure 16:
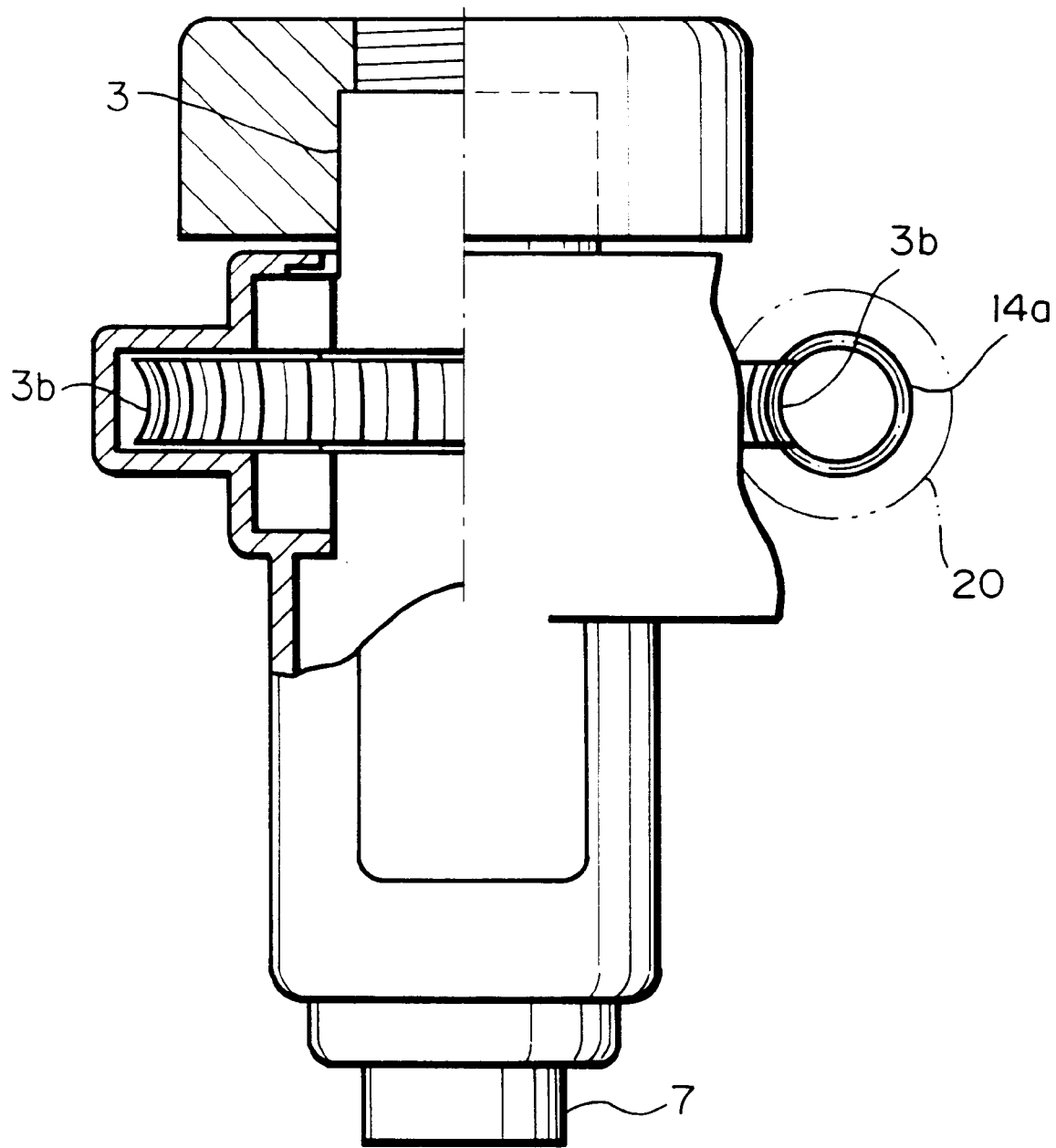
FIG. 16 is a side elevation of the embodiment shown in FIG. 15.

FIGS. 15 and 16 show a first motor drive type embodiment. As shown, a tensile strength tester 1, again labeled 1, includes a grip 2 extending out from the body portion 5a of a casing 5 in the radial direction. A motor or drive means 20 is received in the grip 2. A drive shaft 14 protrudes from the motor 20 and has a worm 14a at its free end. A worm gear 3b is mounted on a sleeve or drive shaft 3. The sleeve 3 is rotatably supported by the casing 5 via radial bearings or single row, deep groove ball bearings 4. A compression type load transformer 6 is fixed to the bottom of the body 5a of the casing 5 coaxially with the body 5a. A seat attachment 7 is held in coaxial threaded engagement with the lower portion of the load transformer 6. A drive plate 8 formed with a hexagonal hole 8a is fixed to the bottom of the sleeve 3 by small screws 16. A pull shaft 9 has a hexagonal head 9a mating with the hexagonal hole 8a of the drive plate 8. A thrust bearing or needle-like roller bearing 11 rotatably supports the pull shaft 9 on the load transformer 6 via a base 10. A plug 12 is inserted in the bore 3a of the sleeve 3 and abuts against the head 9a of the pull shaft 9. A cap 13 abuts against the plug 12. A receptacle connector 15 allows power to be fed to the motor 20 therethrough and allows an electric signal output from the load transformer 6 to be sent out therethrough. An electric system 25 (see FIG. 17) is connected to the electrodes of the receptacle connector 15.

Figure 17A:
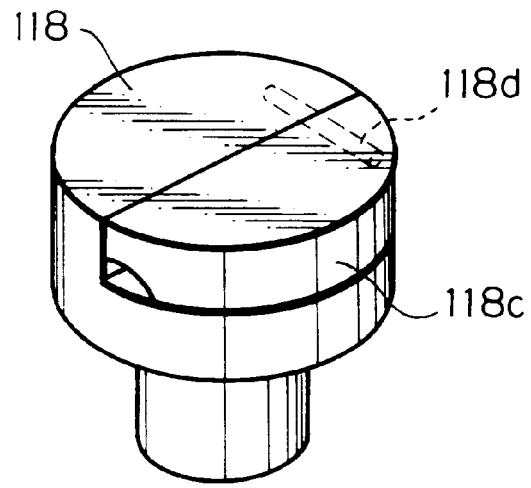
FIGS. 17A and 17B are perspective views showing a specific configuration of a knob included in the embodiment of FIG. 15.
Figure 17B:
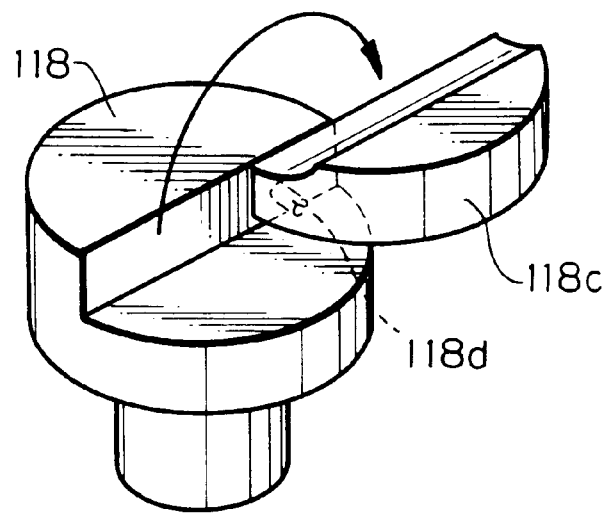
Figure 18:
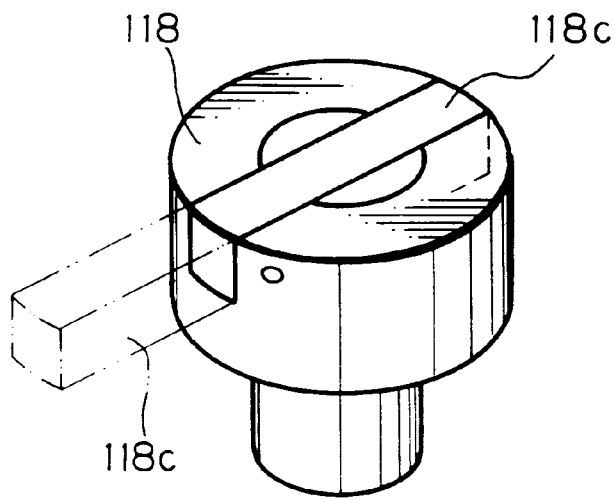
FIG. 18 is a perspective view showing another specific configuration of the knob.

FIGS. 17A and 17B show a specific configuration of the grip 2. As shown, a grip, labeled 118, includes a handle member 118c capable of being rotated about a pin 118d in the direction perpendicular to the axial direction of the grip 2 to a position where it protrudes radially outward from the grip 118. In such a position of the handle member 118c, a sufficient operating torque is available. FIG. 18 shows a modification of the grip 118. If desired, the grip 118 may be replaced with a shaft member capable of being protruded radially outward from the grip.

An ON/OFF switch 21 (see FIG. 19) for selectively turning on or turning off the motor 20 is mounted on the casing 5 in the vicinity of the body 5a. Because a force pressing the switch 21 acts in the vicinity of the center of gravity of the tester, it is prevented from displacing the tester 1.

The bearings 4 are spaced from each other in the axial direction of the tester 1. The worm gear or drive transmitting means 3b is interposed between the bearings 4. With this configuration, it is possible to reduce a thrust load. The center of gravity of the tester 1 should preferably be located between the bearings 4.

The tester 1 measures the tensile strength of a desired article 17. In the illustrative embodiment, the article 17 is assumed to be a screw member or nut 17 welded to a steel sheet.

The seat attachment 7 is formed with an axial bore 7a having an inside diameter D, and a hole 7b communicated to the bore 7a. The pull shaft 9 is loosely fitted in the hole 7b. The inside diameter D of the bore 7a is selected to be greater than the maximum outside diameter d of the screw member 17. When the tester 1 measures the tensile strength of the article 17, a seat surface 7c forming the bottom of the seat attachment 7 rests on the top of the steel sheet 19 around the screw member 17. The attachment 7 therefore plays the role of a seat portion for allowing the tester 1 to be seated on the the steel sheet 19 and to support the sheet 19. Various kinds of seat attachments 7 each having a particular inside diameter are prepared. This, coupled with the fact that the seat attachment 7 is removably mounted to the load transformer 6, allows the attachment 7 to be easily replaced with another seat attachment matching with the maximum diameter of the screw member 17. Further, because the seat attachment 7 is screwed into the load transformer 6, the former can be protruded from the latter to any desired position.

The pull shaft 9 is passed through the hole 7b of the seat attachment 7 coaxially with the attachment 7 and includes a shank 9b and the previously mentioned hexagonal head 9a greater in diameter than the shank 9b. The shank 9b has a threaded portion 9c at its end. When the threaded portion 9c is driven into the screw member 17, a torque applied to the drive plate 8 is transferred to the pull shaft 9 via the head 9a received in the hexagonal hole 8a of the drive plate 8.

The bore 3a of the sleeve 3 to which the drive plate 8 is fixed has a diameter greater than the maximum outside diameter of the head 9a of the pull shaft 9, so that the shaft 9a can be freely pulled out of the bore 3a.

When the motor 20 is energized, the output torque of the motor 20 is transmitted to the sleeve 3 via the drive shaft 14, worm 14a, and work gear 3b. The resulting rotation of the sleeve 3 is transferred to the drive plate 8 and therefrom to the pull shaft 9. As a result, the pull shaft 9 exerts a tensile force corresponding to its rotation angle on the nut 17 via the head 9a, base 10, roller bearing 11, load transformer 6, and seat attachment while exerting a counterforce on the steel sheet 19.

The worm 14 and worm gear 3b playing the role of drive transmitting means allows even several tons of load to be applied to the nut 17 and allows the motor 20 to be reduced in size.

Various kinds of pull shafts 9 each having a threaded portion 9c of particular diameter are also prepared. Only if the plug 12 is removed from the knob 2, the pull shaft 9 can be pulled out of the hole 3a of the sleeve 3. Therefore, the pull shaft 9 can be easily replaced with another pull shaft matching with the diameter of the nut 17.

The roller bearing 11 mounted on the top of the load transformer 6 as a thrust bearing is highly durable even when subjected to a heavy load. The roller bearing 11 may be replaced with a ball bearing if the tester 1 is free from heavy loads. Further, use may be made of a tapered roller bearing.

The base 10 intervening between the thrust bearing 11 and the head 9a of the pull shaft 9 has a preselected substantial thickness. When the diameter of the head 9a is smaller than the maximum outside diameter of the thrust bearing 11, i.e., when the contact area between the head 9a and the bearing 11 is relatively small, the base 10 prevents a local load from acting on the bearing 11. Specifically, the thick base 10 implements the propagation of a stress at 45 degrees and thereby causes a load to act evenly on the thrust bearing 11. The base 10 therefore allows the head 9a to be reduced in size, enhancing a small size, light weight configuration.

The load transformer 6 is fixed to the bottom of the casing 5 and made up of a first flange 6d, a second flange 6a, a pressure sensing portion 6b intervening between the two flanges 6d and 6a, and four strain gauges 6c fitted on the circumference of the pressure sensing portion 6b at equally spaced locations. The first or lower flange 6d is fixed to the casing 5. The second or upper flange 6a abuts against the underside of the head 9a of the pull shaft 9 via the thrust bearing 11 and base 10. In this configuration, the load transformer 6 receives, as a compressive force, a counterforce derived from a tensile force generated in the shaft 9. The pressure sensing portion 6b is thin enough to elastically deform when subjected to the above compressive force. The strain gauges 6c measure the strain of the pressure sensing portion 6b when the compressive force acts on the portion 6b. As shown in FIG. 4, the strain gauges 6c are implemented as a bridge circuit and transform the strain to an electric signal for the measurement of the load. The thin configuration of the portion 6b not only enhances sensitivity, but also implements a space for arranging the strain gauges 6c.

The thin pressure sensing portion 6b intervening between the first and second flanges 6d and 6a constitutes a part of the casing 5. The strain gauges 6c fitted on the pressure sensing portion 6b measure a tensile force acting on the pull shaft 9 in terms of a strain (deformation) in the direction of thrust.

Figure 19:
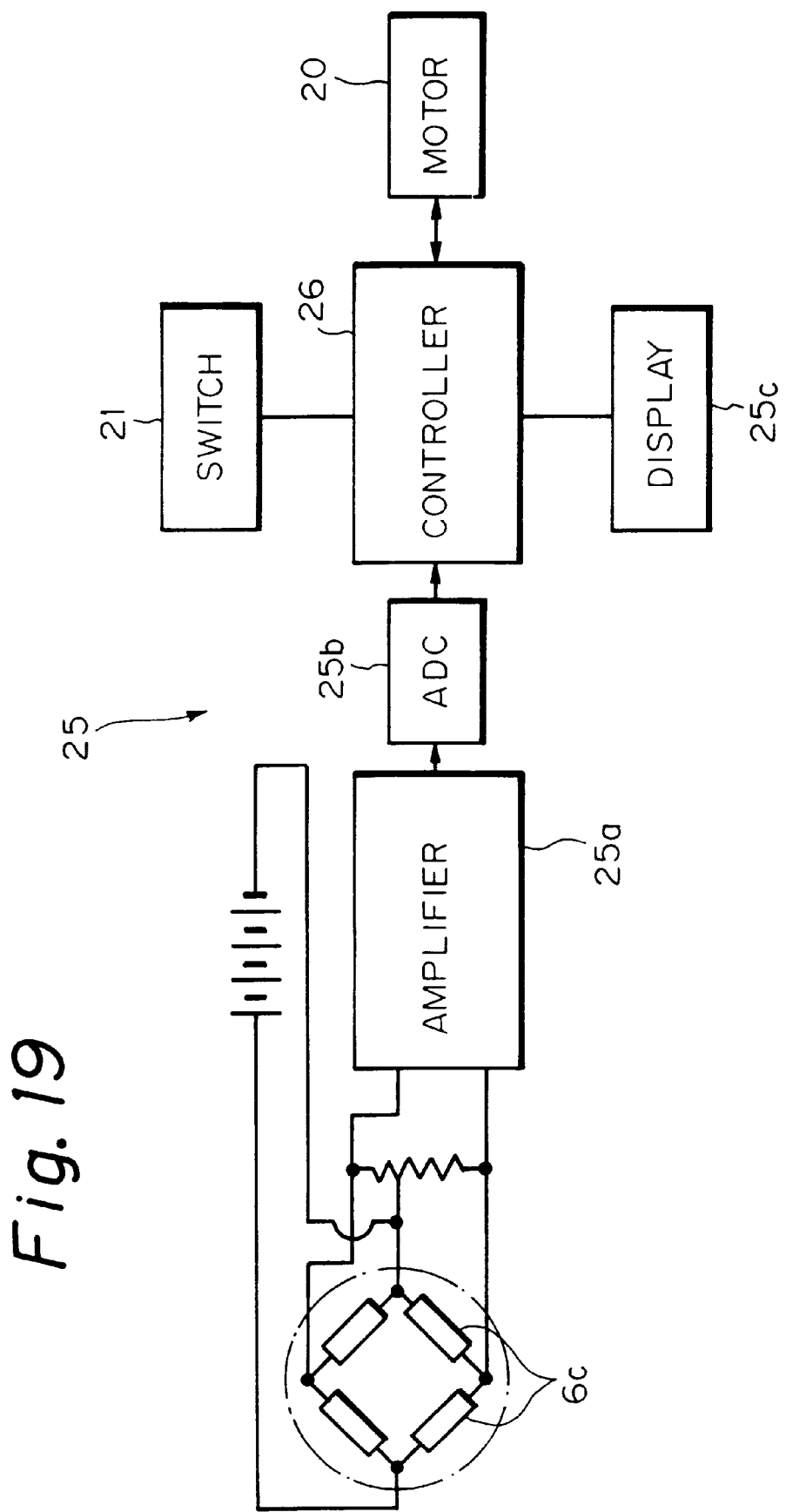
FIG. 19 is a block diagram schematically showing an electric system particular to the embodiment of FIG. 15.
Figure 20:
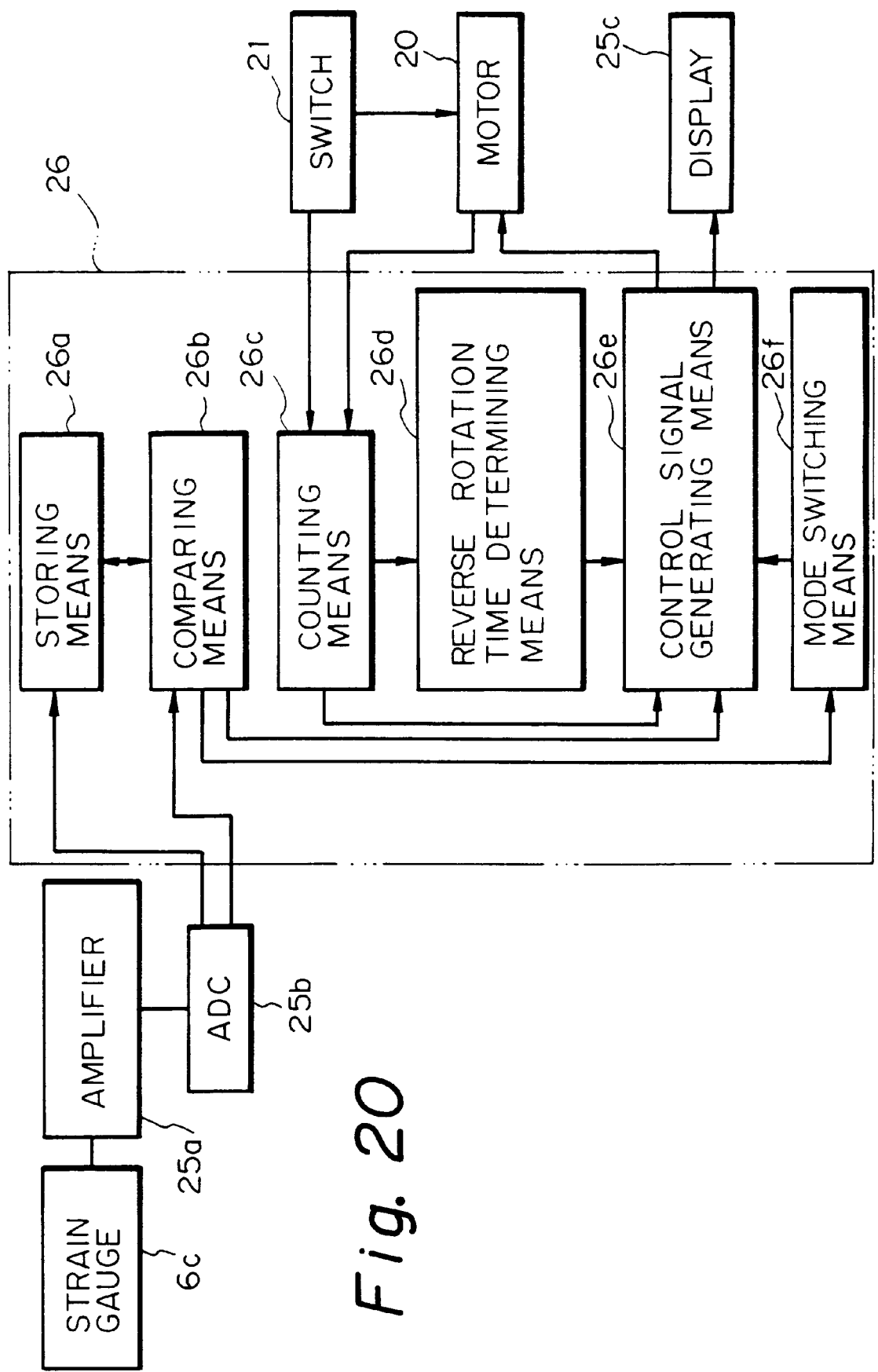
FIG. 20 is a block diagram schematically showing a controller included in the electric system of FIG. 19.

As shown in FIG. 19, the electric system 25 of the illustrative embodiment includes an amplifier 25a, an ADC 25b, a controller 26, a display 20, and the previously mentioned switch 21. As shown in FIG. 20, the controller 26 may be implemented as a microcomputer and includes storing means 26a, comparing means 26b, counting means 26c, reverse rotation time determining means 26d, control signal generating means 26e, and mode switching means 26f. The storing means 26a is capable of storing one or both of a preselected reference tensile force and a measured tensile force. The comparing means 26b compares a tensile force measured by the strain gauges 6c with the reference tensile force stored in the storing means 26a. In addition, the comparing means 26b compares the measured value stored in the storing means 26a with a value measured by the strain gauges later. The counting means 26c counts the duration of rotation of the motor 20 based on the number of rotations. The reverse rotation time determining means 26d determines the duration of reverse rotation of the motor 20 on the basis of the output of the counting means 26c. The control signal generating means 26e sends a measurement start signal to the strain gauges 6c and sends a drive signal to the motor 20. The mode switching means 26f selects one of a breakage value mode, a strength value mode, and a peak value mode at a time. The breakage value mode, strength value mode and peak value mode are respectively represented by steps S5–S7, steps S8–S11, and steps S12–S17 shown in FIG. 21.

Figure 21B:
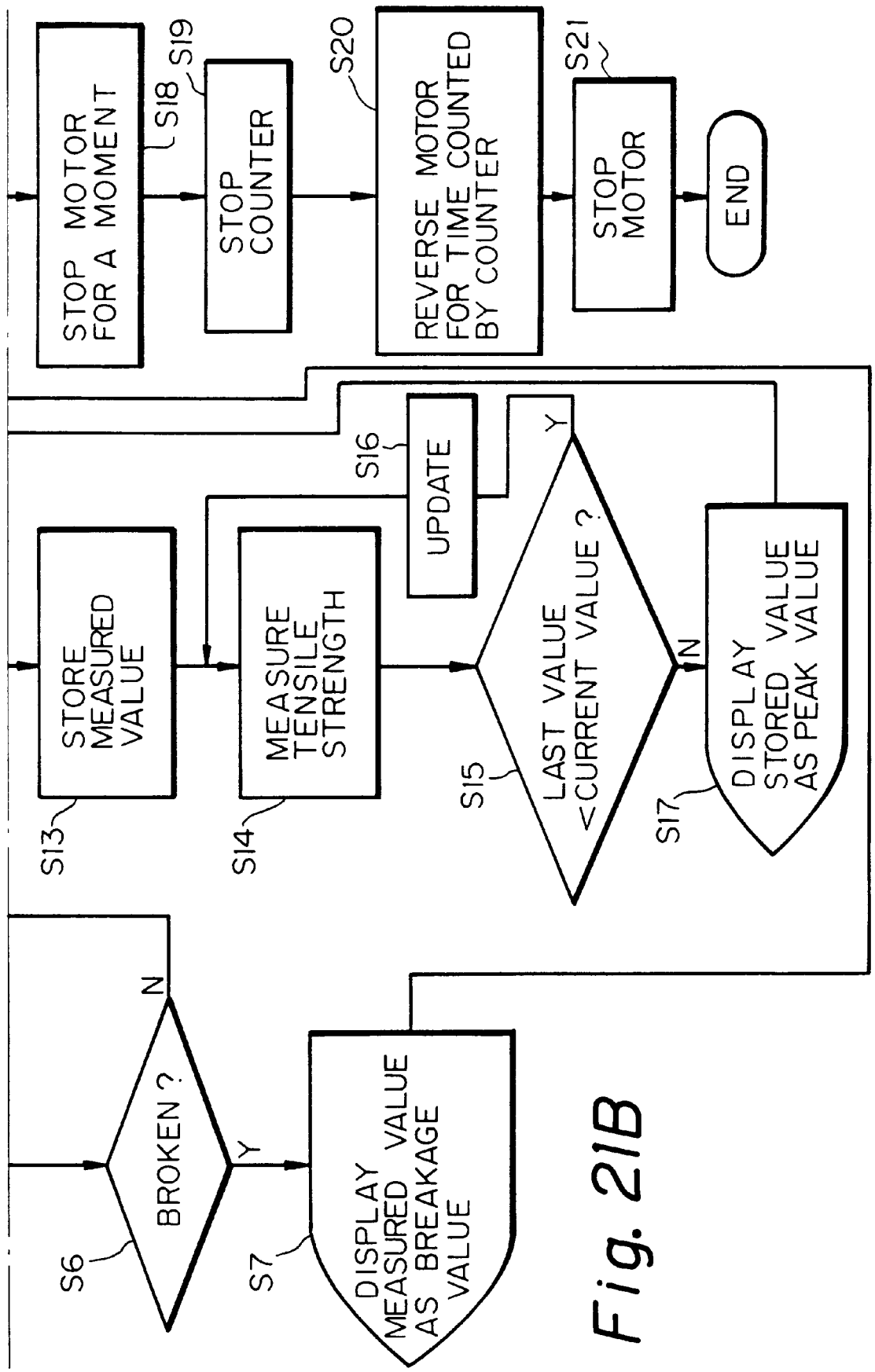
FIG. 21 is a flowchart demonstrating the operation of the embodiment of FIG. 15.

FIG. 21 shows a control program particular to the illustrative embodiment. As shown, the motor 20 is caused to start rotating at a low speed (step S1). On the elapse of a preselected period of time (Y, step S2), the counting means 26c is caused to start counting (step S3). Subsequently, the motor 20 is caused to rotate at a high speed (step S4). In this condition, a tensile force is measured on the basis of an electric signal output from the strain gauges 6c and proportional to the tensile force of the screw member (step S5). Then, whether or not the screw member has broken is determined on the basis of whether or not the output signal of the strain gauges 6c has sharply changed (step S6).

If the answer of the step S6 is positive (Y), then the measured value is displayed on the display 25c as a breakage value (step S7). The step S7 is followed by a step S18. If the answer of the step S6 is negative (N), a tensile force is measured on the basis of the electric signal output from the strain gauges 6c and proportional to the tensile force of the screw member (step S8). The measured tensile strength is written to the storing means 26a (step S9). The measured tensile strength written to the storing means 26a is compared with the reference tensile strength (step S10). If the measured strength is greater than the reference strength (Y, step S10), then the measured value is displayed on the display 25c as a strength value (step S11). The step S11 is followed by a step S18.

If the answer of the step S10 is N, a tensile strength is again measured on the basis of an electric signal output from the strain gauges 6c (step S12). The measured strength is written to the storing means 26a (step S13). A tensile strength is gain measured (step S14) and compared with the strength stored in the storing means 26a (step S15). If the current measured value is greater than the last measured value (Y, step S15), then the measured value stored in the storing means 26a is replaced with the current measured value (step S16), and the program returns to the step S14. If the answer of the step S15 is N, then the stored value is displayed on the display 25c as a peak value (step S17). This is also followed by the step S18.

In the step S18, the motor 20 is deenergized for a moment. Then, the counting means 26c started to operate in the step S3 is caused to stop operating (step S19). Subsequently, the motor 20 is rotated in the reverse direction over a period of time corresponding to the number of rotations counted by the counting means 26c (step S20). Thereafter, the motor 20 is deenergized (step S21).

The operation of the above embodiment is as follows. Before operation, the pull shaft 9 whose threaded portion 9c corresponds in diameter to the nut 17 is mounted to the tester 1. Specifically, after the cap 13 and plug 12 have been sequentially removed from the knob 2, the pull shaft 9 is inserted into the hole 3a of the sleeve 3. After the head 9a of the pull shaft 9 has been received in the hexagonal hole 8a of the drive plate 8, the plug 12 is driven into the knob 2 until the end of the plug 12 abuts against the head 9a. In this condition, the pull shaft 9 is prevented from moving in the axial direction.

For measurement, the seat surface 7c of the seat attachment 7 is caused to rest on the steel sheet 19. Then, the motor 20 is caused to rotate at the low speed. The rotation of the motor 20 is transferred to the pull shaft 9 via the worm 14a, worm gear 3b, sleeve or drive shaft 3, and drive plate 8. As a result the threaded portion 9c of the pull shaft 9 is screwed into the nut 17. When the motor 20 is caused to rotate at the high speed, the rotation angle of the pull shaft 9 sequentially increases from the rotation angle at which the seat attachment 7 has abutted against the steel sheet 19. As a result, a force tending to pull the nut 17 out of the steel sheet 19 and proportional to the above rotation angle acts on the nut 17 due to the threaded engagement of the threaded portion 9c and nut 17. Because the seat attachment 7 fixed to the load transformer 6 has an inside diameter greater than the maximum diameter of the nut 17 and because the pull shaft 9 is coaxial with the attachment 7, the seat surface 7c automatically closely contacts the steel sheet 9 around the nut 17. The seat surface 7a therefore bears the counterforce of the pull shaft 9 via the load transformer 6, thrust bearing 11, base 10, and head 9a. A counterforce acting against the pulling force generated in the pull shaft 9 is transferred to the second flange 6d of the load transformer in the direction opposite to the above direction. Consequently, a compressive force equal, but opposite in direction, to the force pulling the nut 17 acts on the pressure sensing portion 6b. At this instant, the thrust bearing 11 serves to reduce the rotation load of the motor 20.

The tensile force generated in the pull shaft 9 compresses the pressure sensing portion 6b of the load transformer 6 in the axial direction. As a result an electric signal proportional to the tensile force acting on the nut 17 is sent from the strain gauges 6c to the electric system 25 via the intermediate terminals and wirings. The amplifier 25a amplifies the electric signal while the ADC 25b digitizes the amplified electric signal. The resulting digital value appears on the display 25c and allows the force tending to pull out the nut 17 to be read.

As stated above, in the illustrative embodiment, the electric system 25 measures the maximum tensile force, tensile strength and so forth of the screw member 17.

The tester 1 can adapt itself to the configuration and dimensions of the nut or screw member 17 only if the seat attachment 7 and pull shaft 9 are replaced with adequate ones, i.e., without resorting to the replacement of the knob 2. The tester 1 is therefore miniature and portable and makes it needless to cut out the nut portion from the steel sheet 19. such a tester 1 can be used to measure a tensile strength to be measured at a cite.

The pressure sensing portion 6b is implemented as a thin elastically deformable portion. This, coupled with the strain gauges 6c responsive to the deformation of the portion 6b, simplifies the construction and reduces the size of the tester 1. Moreover, because the wirings connecting the load transformer 6 to the electric system 25 are provided with a shield structure and arranged within the casing 5, the tester 1 is highly resistive to noise and prevents the wiring from being cut off during measurement. Consequently, not only reliable measurement but also easy operation are promoted.

The above embodiment prevents the pull shaft 9 from being loosened and allows it to be replaced easily and rapidly when the diameter of the article to be tested is changed or when the shaft 9 wears or is broken or otherwise damaged. In addition, the tester 1 can be positioned vertically by hand while guaranteeing the replaceability of the pull shaft 9. This insures the stable operation of the tester 1 despited that it is automatically driven by the motor 20.

The drive transmitting means is implemented by the worm 14a and worm gear 3b meshing with the worm 14a, so that even a small motor 20 can easily output a great torque. This enhances the free arrangement of the motor 20, i.e., allows it to be received in the grip 2.

Figure 22A:
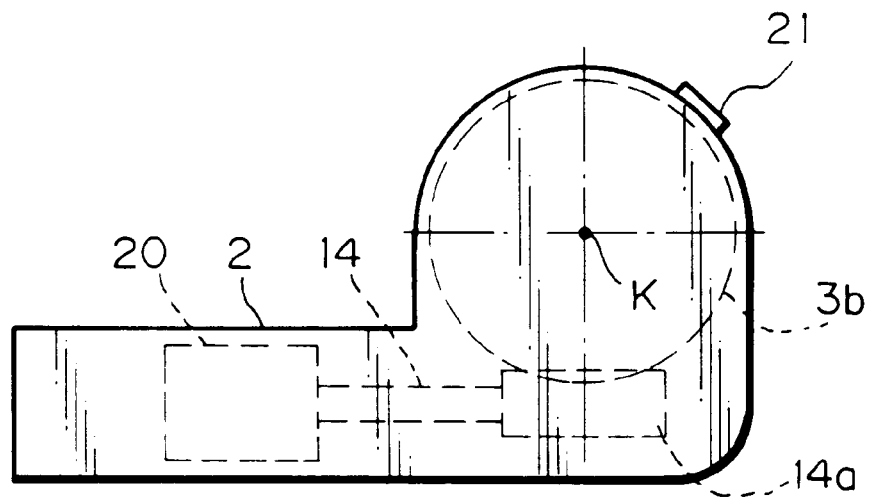
FIGS. 22A and 22B are plan views showing the embodiment of FIG. 15.

As shown in FIG. 22A, the drive shaft 14 of the motor 20 and therefore the grip 2 is offset from the center of rotation of the sleeve 3. It is therefore easy to see the positional relation between the pull shaft 9 and the screw member 17 when the they are seen in the direction parallel to the grip 2.

The motor 20, worm 14a, worm gear 3b and grip 2 are positioned on a horizontal axis extending through the center of gravity G (see FIG. 15) of the tester 1. Therefore, the drive of the motor 20 and the rotation of the pull shaft 9 insure a stable holding ability. In addition, the center of gravity G is stabilized.

A thrust load is reduced because the sleeve 3 is supported by a plurality of bearings 4 axially spaced from each other and because the worm 14a and worm gear 3b are positioned between the bearings 4.

Figure 23A:
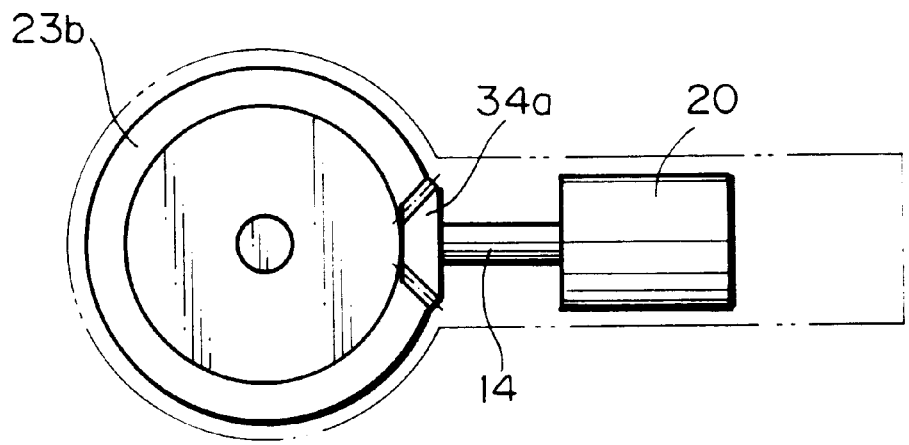
FIGS. 23A and 23B are respectively a plan view and a side elevation showing a modification of the embodiment of FIG. 15.
Figure 23B:
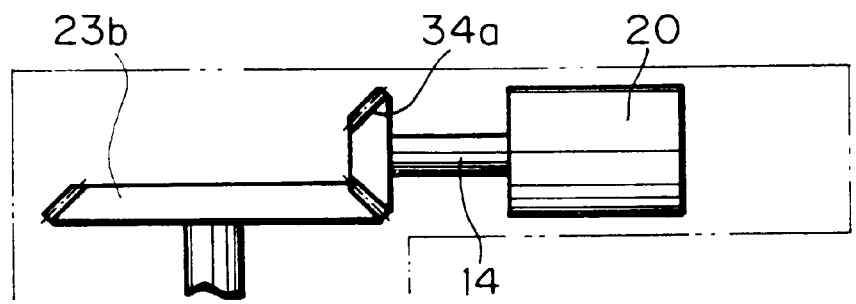

As shown in FIGS. 23A and 23B, the drive transmitting mans may be implemented as bevel gears 34a and 23b. With this arrangement, too, it is possible to locate the grip 2 on the horizontal line extending through the center of gravity in a simple construction.

The ON/OFF switch 21 assigned to the motor 20 is positioned in the vicinity of the body 5a of the grip 2. Therefore, even when the center of gravity G is deviated from the center of rotation due to an offset, a force exerted on the switch 21 for operating it acts at a position close to the center of gravity G. This reduces the influence of the above force on the body of the tester 1.

Figure 23C:
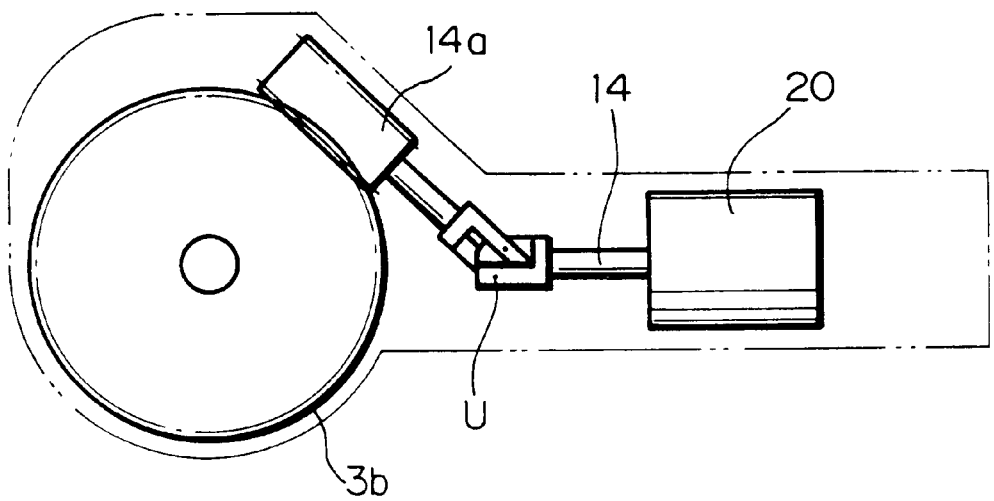
FIG. 23C is a plan view showing another modification of the embodiment of FIG. 15.

As shown in FIG. 23C, the drive shaft 14 may be connected to the worm 14a via a universal joint U. This, coupled with the fact that the grip 2 is located on a horizontal line extending though the center of rotation of the sleeve 3, reduces the deviation of the center of gravity G which would cause the body of the tester 1 to move.

Figure 22B:
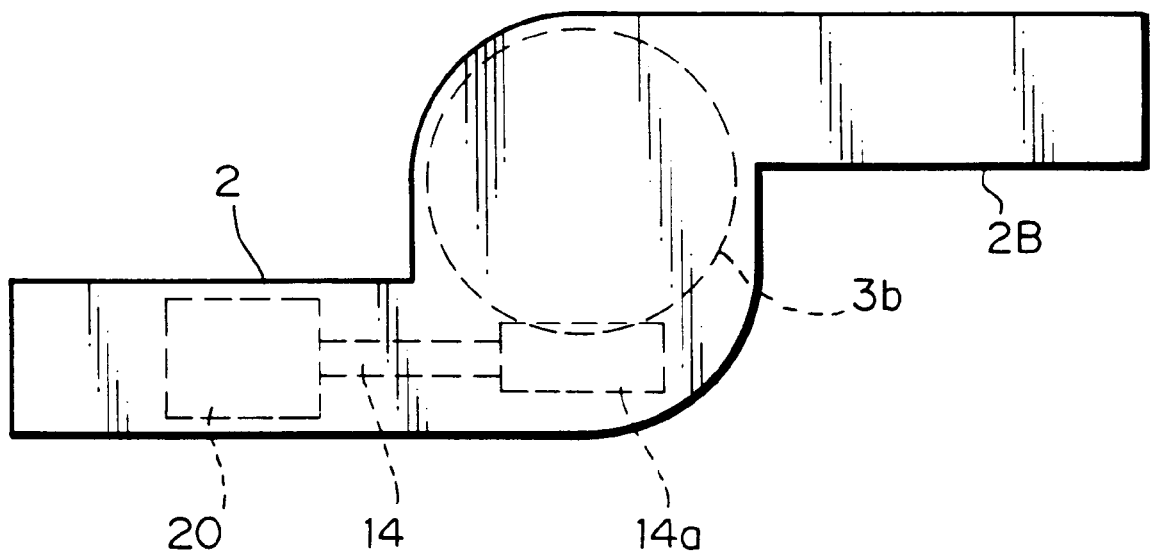

As shown in FIG. 22B, a second grip 2B may extend out from the body 5a of the casing 5 at a position different from the grip 2. When the center of gravity G is displaced due to offset, the second grip 2B reduces the movement of the body of the tester 1 and thereby enhances the holding ability. As shown in FIG. 22A, the switch 21 may be located at the opposite side to the grip 2 with respect to the axis of rotation K. This is also successful to prevent the body of the tester 1 from being displaced by a force exerted on the switch 21.

The second grip 2B is symmetrical in configuration to the grip 2 accommodating the motor 20 therein, so that the center of gravity G can be prevented from being displaced due to an offset.

The drive plate 8 with the hexagonal hole 8a mating with the hexagonal head 9a of the pull shaft 9 is fixed to the end of the sleeve 3 by the screws 16. Alternatively, the sleeve 3 may be provided with a bottom and have a hole (hexagonal hole) formed in the bottom. Of course, the hole may be provided with a configuration other than rectangle so long as it is capable of exerting a rotating force.

Figure 24:
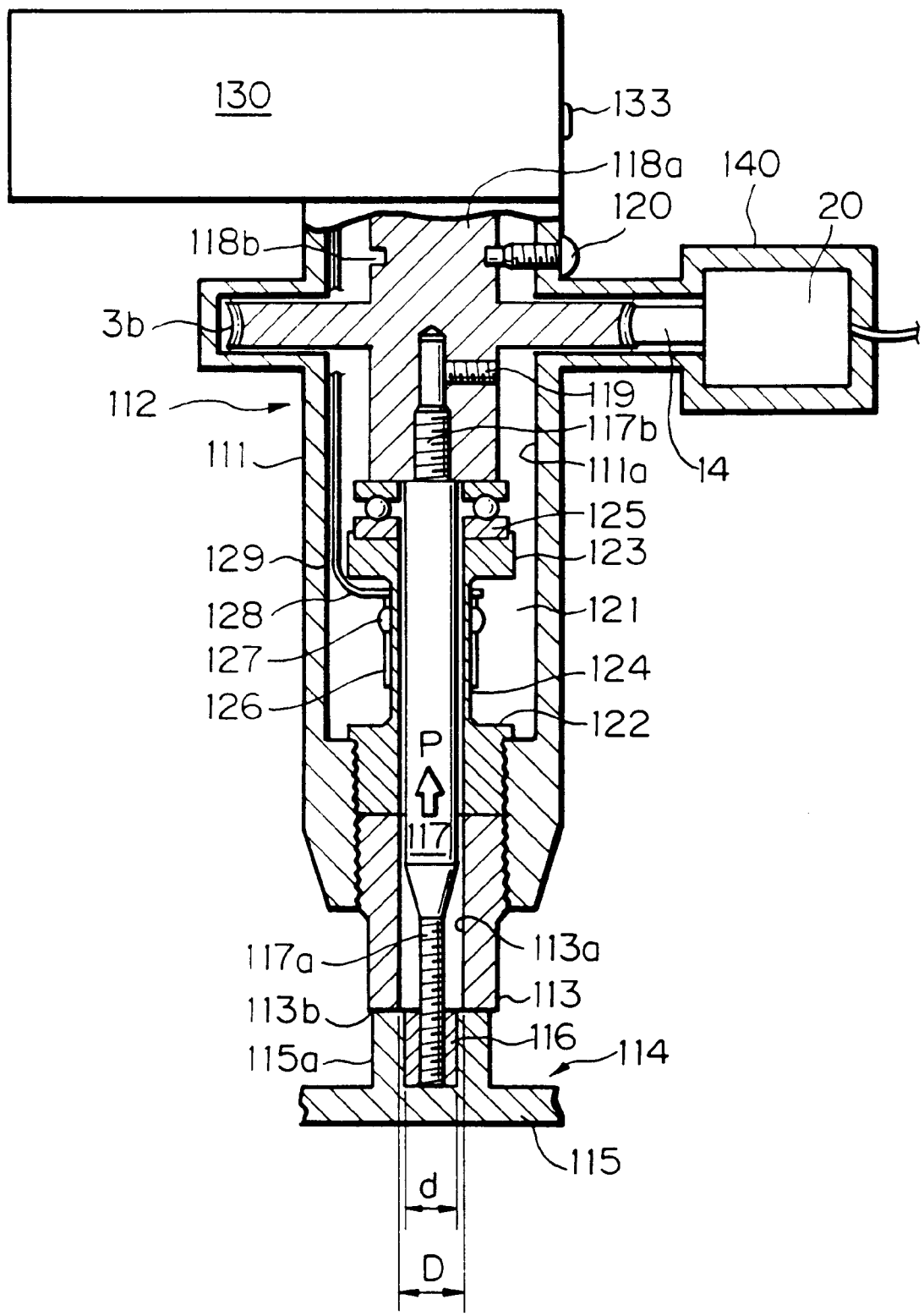
FIG. 24 is a sectional front view showing a second motor drive type embodiment of the tensile strength tester in accordance with the present invention.

Reference will be made to FIGS. 17A, 17B, 18, 24 and 25 for describing a second motor drive type embodiment of the present invention. As shown in FIG. 24, a tensile strength tester, generally 112, includes a hollow cylindrical casing 111 having an adequate diameter to be held by one hand. A hollow cylindrical seat attachment 113 is fitted in the bottom of the casing 111. An article 114 to be tested is made up of a base material 115 formed by, e.g., injection molding and including a boss 115a and a screw member 116 formed in the boss 115a by insertion molding. The tester 112 measures the tensile strength of the article 114. In the illustrative embodiment, the screw member 116 is assumed to be a buried nut.

The seat attachment 113 is removably screwed into the bottom of the casing 111 and formed with an axial bore 113a having an inside diameter D. The diameter D is greater than the maximum outside diameter d of the screw member 116. When the tester 112 measures the tensile strength of the article 114, a seat surface 113b forming the bottom of the seat attachment 113 rests on the top of the boss 115a around the screw member 116. The attachment 113 therefore plays the role of a seat portion for allowing the tester 112 to be seated on the base material 115 and to support the material 115. Various kinds of seat attachments 113 each having a particular inside diameter are prepared. This, coupled with the fact that the seat attachment 113 is removably mounted to the casing 111, allows the attachment 113 to be easily replaced with another seat attachment matching with the maximum diameter of the screw member 116. Further, because the seat attachment 113 is screwed into the casing 111, the former can be protruded from the latter to any desired position.

A pull shaft 117 is passed through the hole 113a of the seat attachment 113 coaxially with the attachment 113. The pull shaft 117 includes a threaded portion 117a capable of mating with the screw member 116 at one end. The other end of the pull shaft 117 is held in threaded engagement with a knob 118 (FIGS. 17A, 17B and 18) mounted on the top of the casing 111. Specifically, the pull shaft 117 is rotatably and coaxially mounted on the casing 111 such that when rotated by a knob 118, the shaft 117 exerts a tensile force P corresponding to its rotation angle on the screw member 116 while exerting a counterforce on the base material 115 via the casing 111. Various kinds of pull shafts 117 each having a threaded portion 117a of particular diameter are prepared. Because the pull shaft 117 is removably mounted to the casing 111, the shaft 117 can be easily replaced with another pull shaft matching with the diameter of the screw member 116.

The knob 118 mounted on the casing 111 includes a boss 118a. After the end 117b of the pull shaft 117 has been screwed into the boss 118a, a setscrew 119 is driven into the boss 118a in order to fix the end 117b to the boss 118a. The pull shaft 117 can be easily replaced only if the setscrew 119 is loosened in order to remove the shaft 117 from the knob 118. A groove 118b is formed in the boss 118a over the entire circumference. A screw is screwed into the upper portion of the casing 111 and received in the groove 118a in order to prevent the knob 118 from slipping out of the casing 111.

Figure 26:
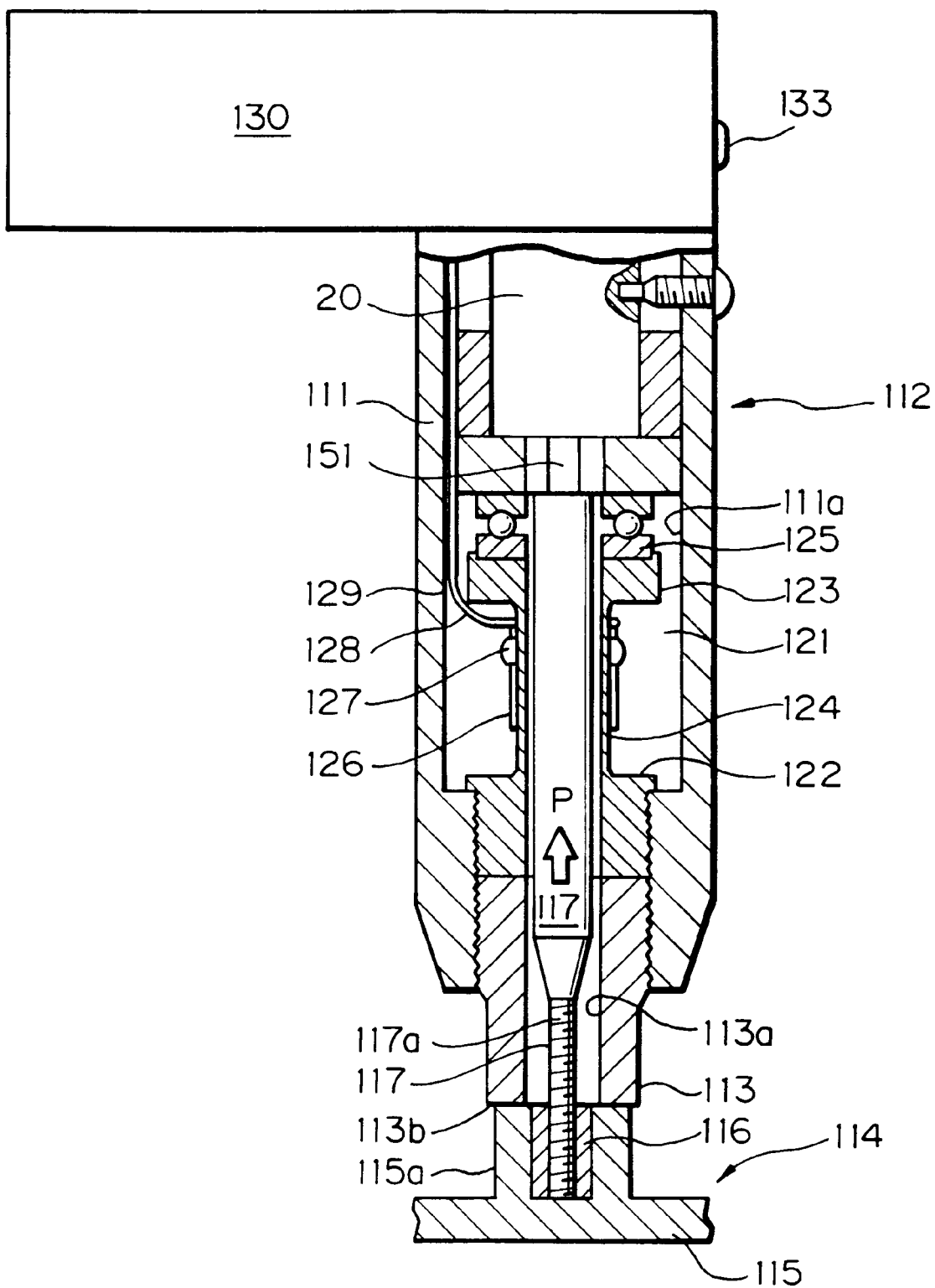
FIG. 26 is a sectional front view showing a modification of the embodiment of FIG. 24.

As shown in FIG. 26, the motor 20 may be directly built in the casing 111 and may have its output shaft 151 directly connected to the pull shaft 117.

As shown in FIGS. 24 and 26, a compression type load transformer 121 is fixed to the bottom of the casing 111 and made up of a first flange 122, a second flange 123, a pressure sensing portion 124 intervening between the two flanges 122 and 123, and strain gauges 126 fitted on the circumference of the pressure sensing portion 124. The first or lower flange 122 is held in threaded engagement with the casing 111. The second or upper flange 123 abuts against the boss 118a via a thrust bearing 125. The flange 123 is mounted on the pull shaft 117 via the thrust bearing 125 and boss 118a so as to receive a counterforce acting against the tensile force P generated in the pull shaft 117 as a compressive force. The pressure sensing portion 124 is thin enough to elastically deform when subjected to the above compressive force. The strain gauges 6c measure the strain of the pressure sensing portion 124 when the compressive force acts on the portion 124. The thin pressure sensing portion 124 intervening between the first and second flanges 122 and 123 constitutes a part of the casing 111.

The strain gauges 126 fitted on the pressure sensing portion 124 measure the tensile force P acting on the pull shaft 117 in terms of a strain (deformation) in the direction of thrust. Specifically, when the pressure sensing portion 124 elastically deforms due to the compressive force, the strain gauges 126 produce an electric signal proportional to the strain rate of the portion 124. The electric signal is input to an electric system 130 (see FIG. 25) via intermediate terminals 127 and wirings 128 and 129 having a shield structure. The electric system 130 includes a controller having a microcomputer, an amplifier and so forth, not shown, in addition to a display 131, switches 132 to be operated by hand, a zero reset switch 133 (see FIGS. 24 and 26), and a battery 134. The electric signal output from the strain gauges 126 is amplified and digitized and has its peak held. As a result, a peak value constantly appears on the digital display 131.

The microcomputer of the electric system 130 stores a reference value representative of a preselected tensile strength and input on the switches 132. When a tensile force appeared on the display 131 is short of the reference value, the controller turns on an "inferior" indication lamp, not shown. The lamp may be replaced with an alert tone, if desired.

Before measurement, the pull shaft 117 whose screw diameter matches with the screw member 116 to be tested is mounted to the tester 112. At the time of measurement, the seat surface 113b of the seat attachment 113 is caused to rest on the boss 115a of the base material 115, and then the knob 118 is turned by hand in order to drive the threaded portion 117a of the pull shaft pull shaft 117 into the screw member 116.

Figure 27:
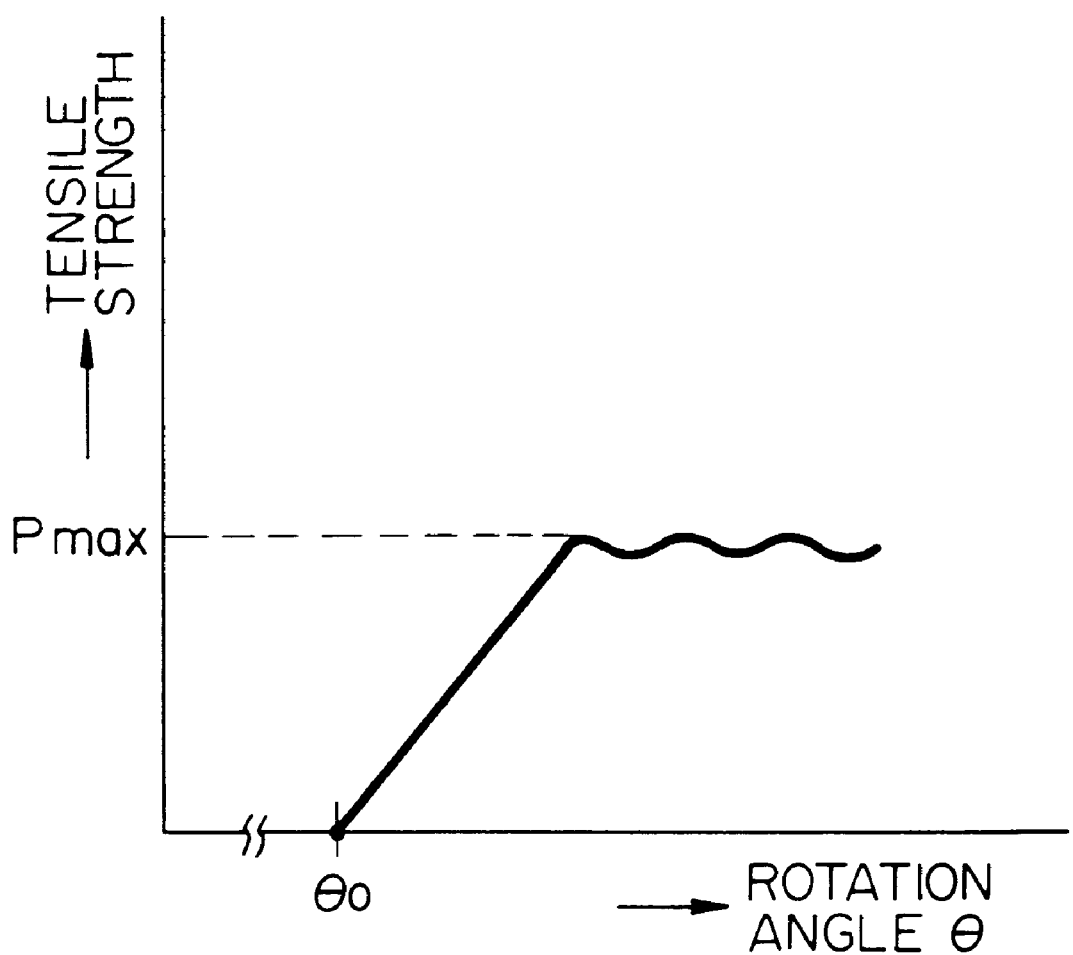
FIG. 27 is a graph showing a relation between a tensile force acting on a screw member and the rotation angle of a knob.

As shown in FIG. 27, as the boss 118a is further rotated, the rotation angle θ of the pull shaft 117 sequentially increases from the rotation angle $θ_0$ at which the seat attachment 113 has abutted against the base material 115. As a result, a force P tending to pull the screw member 116 out of the base material 115 and proportional to the above rotation angle θ acts on the screw member 116 due to the threaded engagement of the threaded portion 117a and screw member 116. Because the seat attachment 113 fixed to the casing 111 has an inside diameter D greater than the maximum diameter d of the screw member 116 and because the pull shaft 117 is coaxial with the attachment 113, the seat surface 113b automatically closely contacts the base material 115 around the screw member 116. The seat surface 113b therefore bears the counterforce of the pull shaft 117 via the end portion 111b of the casing 111, load transformer 121, thrust bearing 125, and knob 118. A counterforce acting against the pulling force generated in the pull shaft 117 is transferred to the second flange 123 of the load transformer in the direction opposite to the above direction. Consequently, a compressive force equal, but opposite in direction, to the force P pulling the screw member 116 acts on the pressure sensing portion 124. At this instant, the thrust bearing 125 serves to reduce the rotation load of the boss 118a.

The tensile force generated in the pull shaft 9 compresses the pressure sensing portion 124 of the load transformer 121 in the axial direction. An electric signal proportional to the tensile force acting on screw member 116 is sent from the strain gauges 126 to the electric system 130 via the intermediate terminals 127 and wirings 128 and 129. The electric signal is amplified by the amplifier and then digitized. The resulting digital value appears on the display 131 and allows the force tending to pull out the screw member 116 to be read. The standard value of the tensile force P may be input on the switches 132 beforehand, in which case a short tensile force will be readily seen by looking at the "inferior" indication lamp.

As the boss 118a is further turned, the force P tending to pull the screw member 116 out of the base material 115 finally overcomes the force binding the screw member 116 and base material 115 to each other and causes the screw member 116 to begin to leave the base material 115. At this instant, the force P reaches its maximum value Pmax shown in FIG. 27 and is read on the display 131. The tester therefore allows the tensile strength of the article to be measured at a work cite immediately. If desired, a lubrication film implemented by oily Teflon or liquid Teflon may be formed between the threaded portion 117a of the pull shaft 117 and the screw member 116 in order to generate a great tensile force P with a small force for turning the knob 118. This will extend the life of the pull shaft 117 to be repeatedly used.

After the above measurement, the operator holding the casing 111 with one hand operates the zero reset switch 133 with, e.g., the thumb of the same hand. This resets the value appearing on the display 131 to zero and prepares the tester for the next measurement. Alternatively, the operator may press an ON/OFF switch 132a included in the switches 132 in order to end measurement.

As stated above, when the tensile strength of the article is short, the illustrative embodiment turns on the "inferior" indication lamp or produces an alert tone. The operator can therefore judge the quality of the article immediately. The tester 112 can adapt itself to various kinds of screw members 116 only if the seat attachment 113 and pull shaft 117 are replaced, i.e., without resorting to the replacement of the knob 118. The tester 112 is therefore small size and easy to convey. This, coupled with the fact that the screw member portion does not have to be cut out from the base material 115, allows the article 114 to be easily tested at a work cite. The testing time available with the illustrative embodiment is only 1/10 to 1/50 of the testing time particular to conventional testers.

The pressure sensing portion 124 is implemented as a thin elastically deformable portion. This, coupled with the strain gauges 126 responsive to the deformation of the portion 124, simplifies the construction and reduces the size of the tester 112. Moreover, because the wirings 128 and 129 connecting the load transformer 121 to the electric system is provided with a shield structure and arranged within the casing 111, the tester 112 is highly resistive to noise and prevents the wirings from being cut off during measurement. Consequently, not only reliable measurement but also easy operation are promoted.

Figure 28:
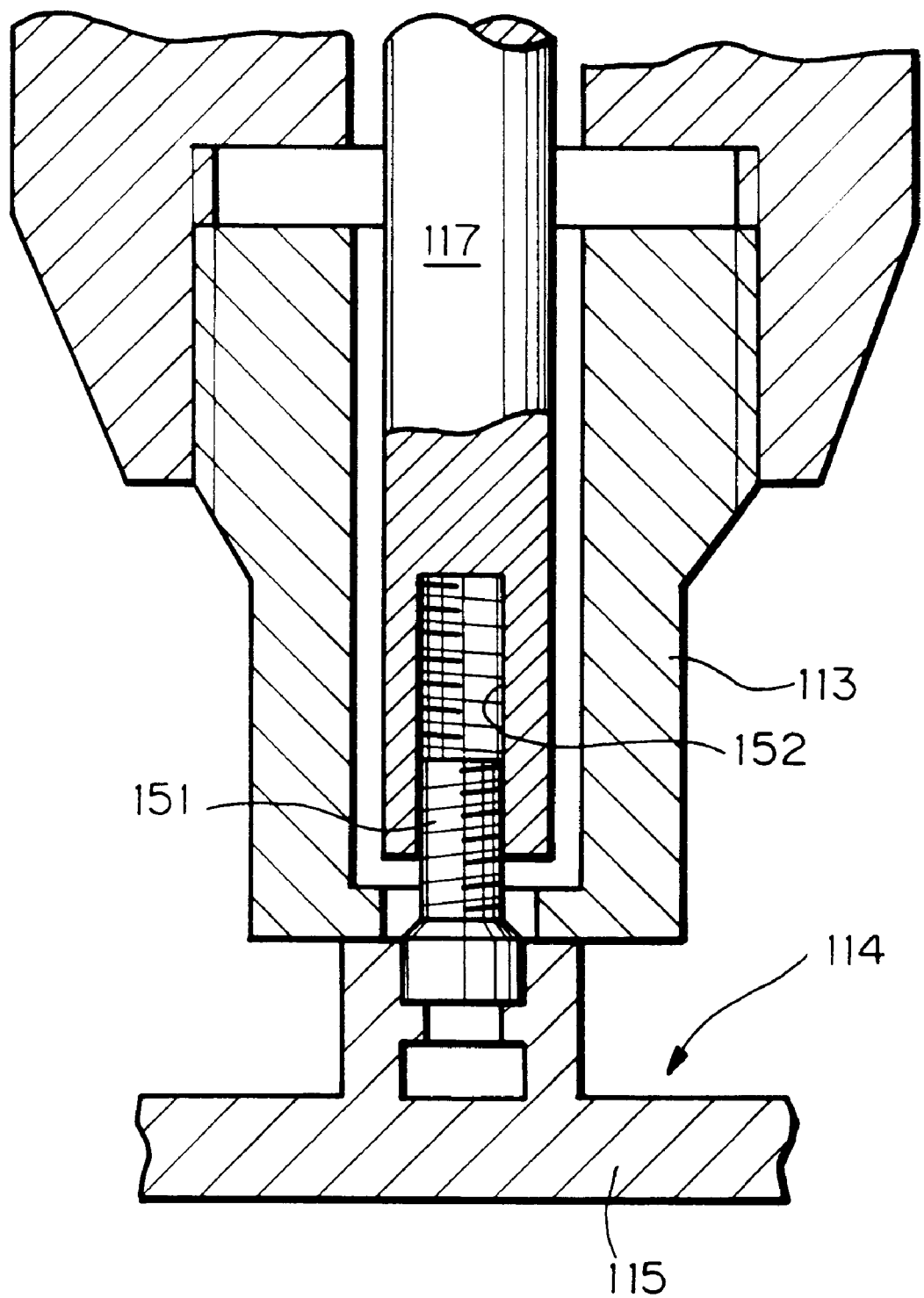
FIG. 28 is a section showing another article to be measured and a modified form of a pull shaft included in each of the embodiments shown in FIGS. 15 and 24.

In the first and second embodiments, the screw member 116 is assumed to be a buried nut formed with a female screw. As shown in FIG. 28, the above embodiments are practicable even with a male screw member 151 formed in the article 114 by insertion molding, in which case the pull shaft 117 will be formed with a female screw 152 complementary to the male screw member 151. Of course, the thrust bearing 125 or 147 for transferring the reaction from the screw member 116 to the load transformer 121 or 141, respectively, may be replaced with any other type of bearing capable of bearing a thrust load.

In the tensile strength tester using the motor drive scheme, the pull shaft 9 is rotated at a lower speed than during measurement for a preselected period of time since the start of rotation of the motor 20, so that the shaft 9 and screw member 17 can easily mate with each other. After the shaft 9 and screw member 17 have mated with each other, the pull shaft 9 is rotated at the speed assigned to measurement. Therefore, sure and stable mating is achievable despite the use of the motor or similar drive means 20, and the measurement is sped up.

Further, the rotation of the sleeve 3 can be transferred to the pull shaft 9 with a counterforce being absorbed at the portion where the sleeve 3 and shaft 9 are connected to each other. This prevents such a connecting portion from being loosened.

With the storing means 26a, comparing means 26b and control signal generating means 26e, it is possible to measure a tensile strength on the basis of a reference value guaranteeing safety. The tester can therefore adapt itself to an article which should be estimated with respect to a certain set value. Because the article does not have to be broken, the screw member 17 is prevented from biting into the pull shaft 9.

When the peak/breakage value of the tensile strength is before the reference value stored in the storing means 26a is reached, the motor 20 is deenergized. This prevents the motor 20 from being wastefully driven when breakage occurs earlier than expected due to, e.g., short strength. Further, the motor 20 can be deenergized on the basis of the output of the comparing means 26b.

Because the peak/breakage value appears on the display 25c, the tester can be brought to, e.g., a molding cite for measurement.

The tensile strength of an article can be determined only if a peak value is known. With the storing means 26a capable of storing the reference value and measured value, comparing means 26b for comparing them, and control signal generating means 26e capable of updating the measured value stored in the storing means 26a, it is possible to determine a peak value if the measured value is smaller than the stored value and use the stored value as a peak value.

After the peak value has appeared, the motor 20 is driven in the reverse direction and then deenergized. This facilitates the removal of the screw member 17 from the pull shaft 9. The easy removal of the screw member 17 is further promoted by the counting means 26c and reverse rotation time determining means 26d. After the appearance of the set/peak value, the motor 20 is rotated in the reverse direction on the basis of a period of time determined by the reverse rotation determining means 26d.

The second embodiment, like the first embodiment shown in FIGS. 15 and 16, may accommodate the motor 20, drive shaft 14, worm 14a, worm gear 3b and electric system 25 in the grip 130 and use the control arrangement shown in FIGS. 19–21. If desired, the motor torque may be sensed in order to output a measurement command when the motor torque is stabilized. Alternatively, as shown in FIGS. 20 and 21, a period of time necessary for a constant speed to be reached may be set beforehand, so that measurement can be started on the basis of the operation of a counter on the elapse of the above period of time. Such alternative schemes each allows a tensile force to be measured after the stabilization of the rotation and thereby promotes accurate estimation of a tensile force.

In FIGS. 20 and 22, the pull shaft 9 is rotated at a constant speed (first speed) which is lower than a constant speed assigned to measurement in order to facilitate the mating of the shaft 9 with the screw member. The pull shaft 9 may be accelerated from the first speed to a preselected constant speed (second speed) little by little.

Three different operation modes are available with the illustrative embodiment, i.e., a set mode (A) using a set value and determines whether or not the screw member (nut, bolt or the like) does not separate from the base material even at the set value, a peak value mode (B) for measuring a peak value, and a breakage value mode (C) for measuring a breakage value.

As shown in FIG. 21, in the set mode (A), the tensile strength stored in the step S9 is compared with the measured tensile strength (step S10). If the reference strength is greater than the measured strength (N, step S10), then the measured value is displayed on the display 25c as a strength value (step S11). The step S11 is followed by a step S18. If the answer of the step S10 is Y, a tensile strength is measured on the basis of an electric signal output from the strain gauges 6c (step S12). The measured strength is written to the storing means 26a (step S13). A tensile strength is again measured (step S14) and compared with the measured strength stored in the storing means 26a (step S15). If the current measured value is greater than the last measured value (Y, step S15), then the measured value stored in the storing means 26a is replaced with the current measured value (step S16), and the program returns to the step S14. If the answer of the step S15 is N, then the stored value is displayed on the display 25c as a peak value (step S17). This is also followed by the step S18. In the step S18, the motor 20 is deenergized for a moment.

By the above control, it is possible to determine whether or not the screw member does not separate from the base material even at the set value.

After the step S18, the counting means 26c is caused to stop operating (step S19). Then, the motor 20 is rotated in the reverse direction for a period of time corresponding to the number of rotations counted by the counting means 26c (step S20). Finally, the motor 20 is deenergized (step S21).

The above reverse rotation of the motor 20 allows the pull shaft 9 to be automatically released from the screw member.

The construction shown in FIG. 15 including the motor 20, storing means 26a, comparing means 26b and control means 26 allows a tensile strength to be measured within the measurable range of the tester; otherwise, the tester would be damaged.

The motor or drive means 20 is caused to rotate in the reverse direction before it is stopped, so that the screw member 17 can be released from the pull shaft 9 with ease.

A procedure to be executed when a breakage value is reached before the set value is as follows. As shown, whether or not the screw member has broken is determined on the basis of whether or not the output signal of the strain gauges 6c has sharply changed (step S6). If the answer of the step S6 is positive Y, then the measured value is displayed on the display 25c as a breakage value (step S7). The step S7 is followed by a step S18. In the step S18, the motor 20 is deenergized for a moment (emergency stop). Then, the counting means 26c started to operate in the step S3 is caused to stop operating (step S19). Subsequently, the motor 20 is rotated in the reverse direction over a period of time corresponding to the number of rotations counted by the counting means 26c (step S20). Thereafter, the motor 20 is deenergized (step S21).

Assume that the tensile strength reaches its peak value or breakage value before reaching the set tensile strength stored in the storing means 26a. Then, the motor 20 is caused to stop rotating. This obviates the wasteful drive of the motor 20 when breakage occurs earlier than expected due to, e.g., short strength. In addition, the peak value or breakage value can be read on the display. The tester can therefore be brought to, e.g., a molding cite for measurement.

Figure 29A:
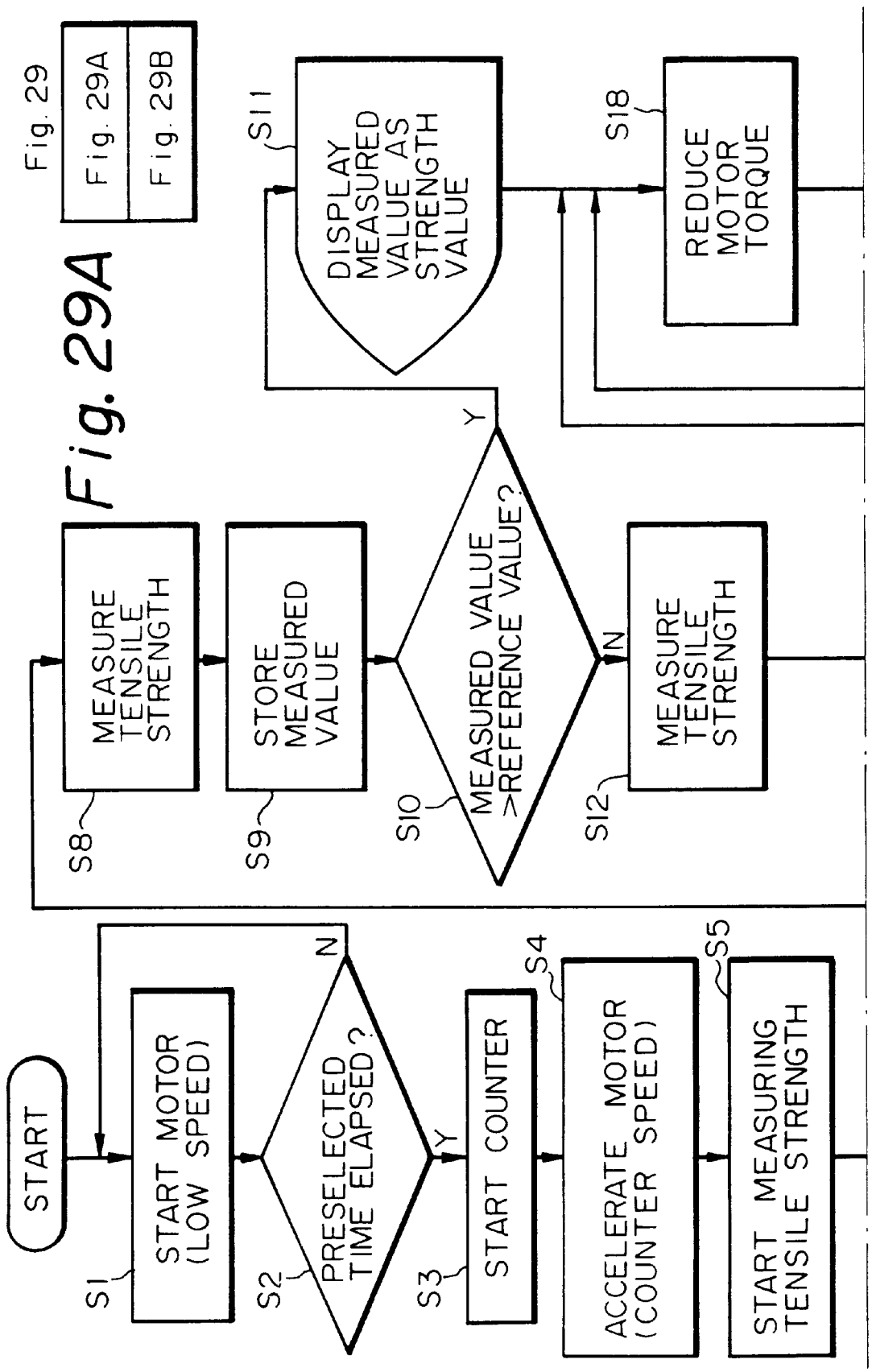
FIG. 29 is a flowchart demonstrating the operation of the embodiment shown in FIG. 24.
Figure 29B:
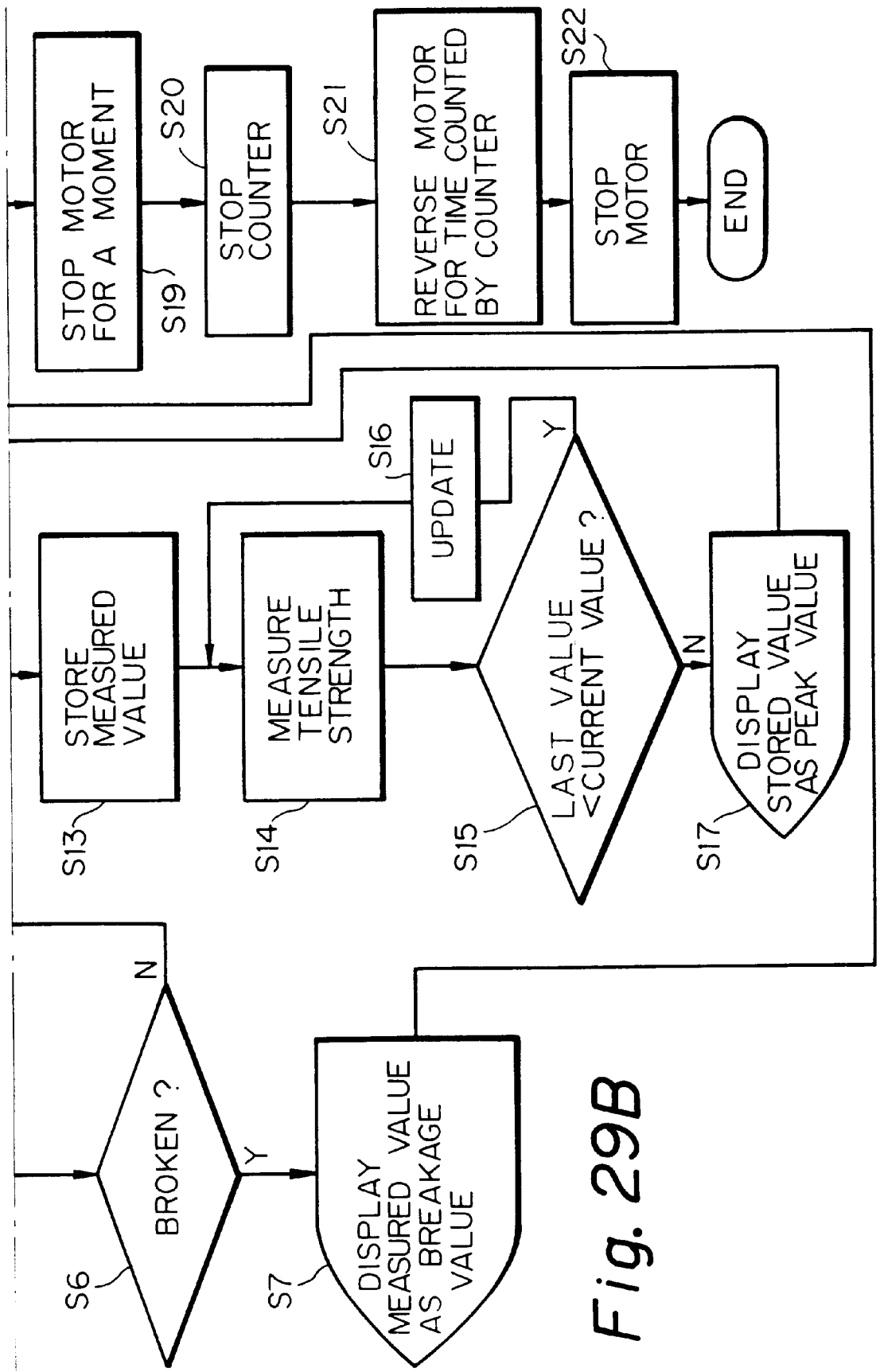

FIG. 29 shows a procedure for decelerating the motor 20 to the low speed (third speed) when a peak value occurs before the reference value. As shown, the motor 20 is energized and rotated at a low speed (step S1) until a preselected period of time expires (Y, step S2). Then, the counting means 26c is caused to start operating (step S3). Subsequently, the motor 20 is accelerated (step S4). In this condition, a tensile force is measured on the basis of an electric signal proportional to the tensile strength and output from the strain gauges 6c (step S5). Whether or not the screw member has broken is determined on the basis of whether or not the output signal of the strain gauges 6c has sharply changed (step S6). If the answer of the step S6 is positive Y, then the measured value is displayed on the display 25c as a breakage value (step S7).

If the answer of the step S6 is N, then a tensile strength is again measured on the basis of the above electric signal (step S8). After the measured value has been written to the storing means (step S9), whether or not the measured value is greater than the reference value is determined (step S10). If the answer of the step S10 is Y, the measured value is displayed on the display 25c (step S11). If the answer of the step S10 is N, a tensile strength is again measured (step S12), and then the value determined in the step S12 is written to the storing means (step S13). Subsequently, a tensile strength is again measured (step S14). The step S14 is followed by a step S15 for determining whether or not the measured value is greater than the stored value (measured value). If the answer of the step S15 is Y, the measured value stored in the storing means in the step S12 is replaced by the measured value of the step S14 (step S16), and the program returns to the step S14.

If the answer of the step S15 is N, the stored value is displayed on the display 25c as a peak value (step S17). Subsequently, the drive torque for the motor 20 is reduced (step S18). This reduces the load to act on the motor 20 when the base material 19 and screw member 17 are abruptly separated from each other.

In a step S19 following the step S18, the motor 20 is deenergized for a moment. Then, the counting means 26c is caused to stop operating (step S20). Subsequently, the motor 20 is rotated in the reverse direction for a period of time corresponding to the number of rotations counted by the counting means 26c (step S21). Finally, the motor 20 is deenergized (step S22).

The tester shown in FIG. 15 allows a digital measured tensile strength, or peak or breakage value, to be directly read on the display 25c. The tester can therefore be easily brought to, e.g., a molding cite for measurement. The mode switching means 26f selects either the set mode in which the motor 20 is energized on the basis of the result of comparison between the reference value and the measured value, or the peak value mode in which the motor 20 is energized on the basis of the result of comparison between the measured values sequentially written to the storing means 26a. The tensile strength of an article can be determined only if a peak value is known. It is therefore possible to determine a peak value if the measured value is smaller than the stored value, and to use the stored value as a peak value.

In the peak value mode, when the measured value is greater than the set value, the measured value is substituted for the set value and written to the storing means 26a as a new set value. Then, a tensile strength is again measured. If the updated set value stored in the storing means 26a is greater than the latest measured value, it is displayed as a peak value.

The peak value mode (B) will be described more specifically with reference to FIG. 20. The tensile strength measured in the step S14 is compared with the measured strength stored in the storing means 26a in the step S13 (step S15). If the current measured value is greater than the last measured value (Y, step S15), then the measured value stored in the storing means 26a is replaced with the current measured value (step S16), and the program returns to the step S14. If the answer of the step S15 is N, then the stored value is displayed on the display 25c as a peak value (step S17). This is also followed by the step S18.

In the step S18, the motor 20 is deenergized for a moment. Then, the counting means 26c started to operate in the step S3 is caused to stop operating (step S19). Subsequently, the motor 20 is rotated in the reverse direction over a period of time corresponding to the number of rotations counted by the counting means 26c (step S20). Thereafter, the motor 20 is deenergized (step S21).

The tensile strength of an article can be determined only if a peak value is known. It is therefore possible with the tester shown in FIGS. 15 and 16 to determine a peak value if the measured value is smaller than the stored value and, to use the stored value as a peak value. Conventional testers are capable of dealing only with a breakage value. The reverse rotation of the motor 20 allows the pull shaft 9 to be automatically released from the screw member. The motor or drive means 20 is caused to rotate in the reverse direction before it is stopped, so that the screw member 17 can be released from the pull shaft 9 with ease.

The drive of the motor 20 is stopped, as follows. As shown in FIG. 20, the counting means 26c is capable of counting the duration of rotation in terms of the number of rotations of the motor 20 occurring during the interval between the turn-on of the switch 21 and the stop of the motor 20. The reverse rotation time determining means 26d is capable of determining, based on the above duration of rotation, a period of time for which the motor 20 should be reversed.

As shown in FIG. 21, the tensile strength measured in the step S14 is compared with the value stored in the step S13 (measured value) (step S15). If the current measured value is greater than the last measured value (Y, step S15), then the measured value stored in the storing means 26a is replaced with the current measured value (step S16), and the program returns to the step S14. If the answer of the step S15 is N, then the stored value is displayed on the display 25c as a peak value (step S17). This is also followed by the step S18.

In the step S18, the motor 20 is deenergized for a moment. Then, the counting means 26c started to operate in the step S3 is caused to stop operating (step S19). Subsequently, the motor 20 is rotated in the reverse direction over a period of time corresponding to the number of rotations counted by the counting means 26c (step S20). Thereafter, the motor 20 is deenergized (step S21).

In the tester shown in FIGS. 15 and 16, the motor 20 is deenergized on the basis of the output of the comparing means 26b. The tester is therefore applicable even to an article which should be estimated with respect to a certain set value. Conventional testers are capable of measuring only a breakage value, relying on manual operation. Assume that the tensile strength reaches its peak value or breakage value before reaching the set tensile strength stored in the storing means 26a. Then, the motor 20 is caused to stop rotating. This obviates the wasteful drive of the motor 20. In addition, the peak value or breakage value can be read on the display. The tester can therefore be brought to, e.g., a molding cite for measurement.

The tensile strength of an article can be determined only if a peak value is known. It is therefore possible to determine a peak value if the measured value is smaller than the stored value, and to use the stored value as a peak value.

In the peak value mode, when the measured value is greater than the set value, the measured value is substituted for the set value and written to the storing means as a new set value. Then, a tensile strength is again measured. If the updated set value stored in the storing means is greater than the latest measured value, it is displayed as a peak value.

The motor or drive means 20 is caused to rotate in the reverse direction before it is stopped, so that the screw member 17 can be released from the pull shaft 9 with ease.

The reverse rotation of the motor 20 is executed, as follows. As shown in FIG. 19, the electric system 25 includes the amplifier 25a, ADC 25b, controller 26, display 20, and switch 21. As shown in FIG. 20, the controller 26 may be implemented as a microcomputer and includes the storing means 26a, comparing means 26b, counting means 26c, reverse rotation time determining means 26d, control signal generating means 26e, and mode switching means 26f. The storing means 26a is capable of storing one or both of a preselected reference tensile force and a measured tensile force. The comparing means 26b compares a tensile force measured by the strain gauges 6c with the reference tensile force stored in the storing means 26a. In addition, the comparing means 26b compares the measured value stored in the storing means 26a with a value measured by the strain gauges later. The counting means 26c counts the duration of rotation of the motor 20 based on the number of rotations. The reverse rotation time determining means 26d determines the duration of reverse rotation of the motor 20 on the basis of the output of the counting means 26c.

As shown in FIG. 21, the motor 20 is rotated in the reverse direction over a period of time corresponding to the number of rotations counted by the counting means 26c (step S20). Thereafter, the motor 20 is deenergized (step S21).

In the construction shown in FIGS. 15 and 16, the motor or drive means 20 is caused to rotate in the reverse direction before it is stopped, so that the screw member 17 can be released from the pull shaft 9 with ease.

The breakage value mode (C) is basically identical with the the operation of any one of the testers shown and described.

Figure 30:
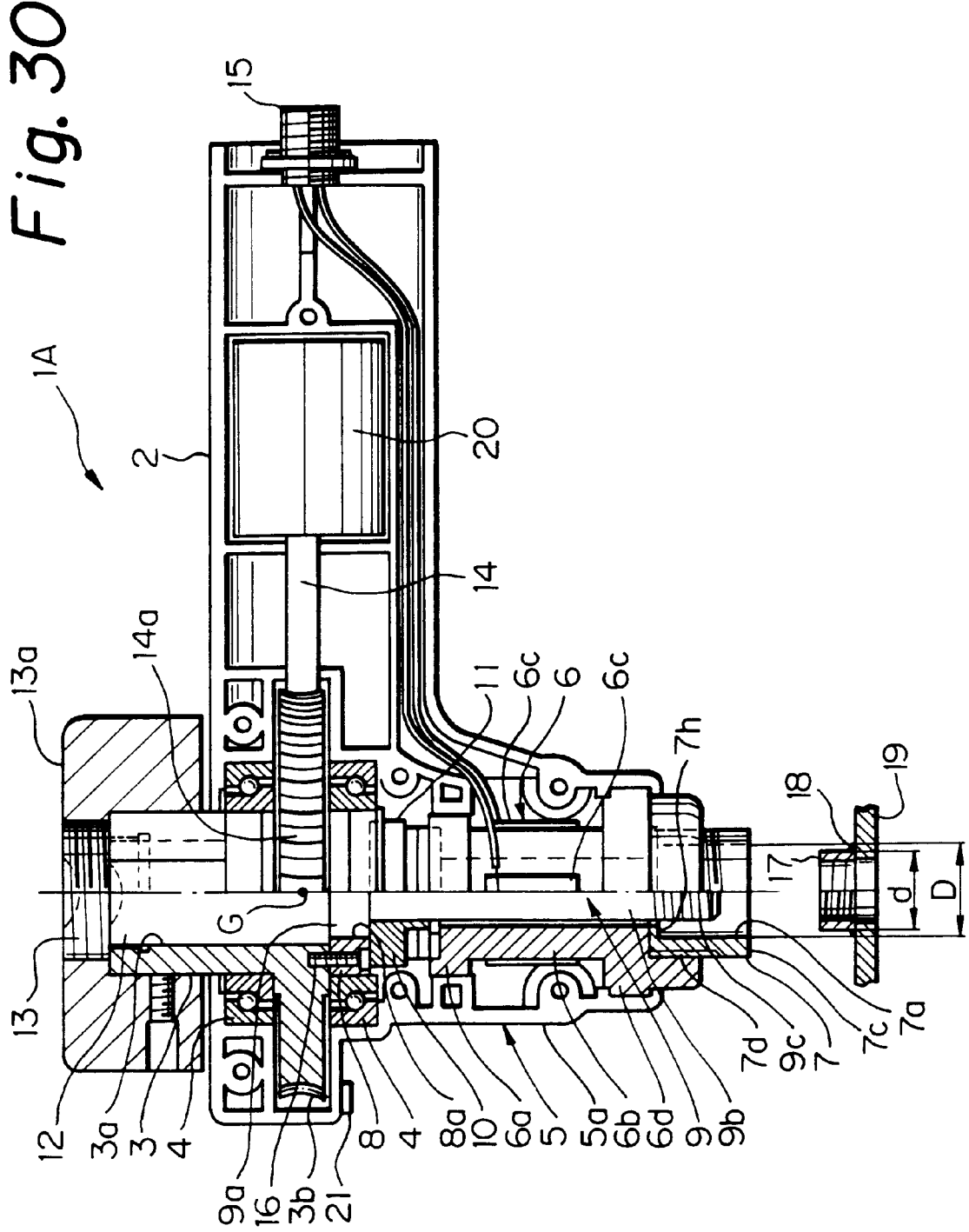
FIG. 30 is a sectional front view showing a third motor drive type embodiment of the tensile strength tester in accordance with the present invention.

Reference will be made to FIG. 30 for describing a third motor drive type embodiment of the present invention. This embodiment is also shown in a side elevation in FIG. 16. As shown, a tensile strength tester, labeled 1A, includes a grip 2 extending out from the body portion 5a of a casing 5 in the radial direction. A motor or drive means 20 is received in the grip 2. A drive shaft 14 protrudes from the motor 20 and has a worm 14a at its free end. A worm gear 3b is mounted on a sleeve or drive shaft 3. The sleeve 3 is rotatably supported by the casing 5 via radial bearings or single row, deep groove ball bearings 4. A compression type load transformer 6 is fixed to the bottom of the body 5a of the casing 5 coaxially with the body 5a. A seat attachment 7 is held in coaxial threaded engagement with the lower portion of the load transformer 6. A drive plate 8 formed with a hexagonal hole 8a is fixed to the bottom of the sleeve 3 by small screws 16. A pull shaft 9 has a hexagonal head 9a mating with the hexagonal hole 8a of the drive plate 8. A thrust bearing or needle-like roller bearing 11 rotatably supports the pull shaft 9 on the load transformer 6 via a base 10. A plug 12 is inserted in the bore 3a of the sleeve 3 and abuts against the head 9a of the pull shaft 9. A cap 13 abuts against the plug 12. A receptacle connector 15 allows power to be fed to the motor 20 therethrough and allows an electric signal output from the load transformer 6 to be sent out therethrough. An electric system 25 (see FIG. 19) is connected to the electrodes of the receptacle connector 15.

In the illustrative embodiment, the seat attachment 7 is held in threaded engagement with the bottom of the load transformer 6. The seat attachment 7 includes a threaded portion 7b threaded in the opposite direction to the threaded portion 9c of the pull shaft 9. The seat attachment 7 additionally includes an irregular portion or abutment 7h against which a broken nut 17 will abut. Further, the lower end portion of the seat attachment including a seat surface 7c is magnetized.

The pull shaft 9 has such a length that its bottom is positioned above the bottom of the seat attachment 7, i.e., the seat surface 7c. At least the bottom portion of the pull shaft 9 is also magnetized.

An ON/OFF switch 21 for selectively turning on or turning off the motor 20 is mounted on the casing 5 in the vicinity of the body 5a. Because a force pressing the switch 21 acts in the vicinity of the center of gravity of the tester 1A, it is prevented from displacing the tester 1A.

The bearings 4 are spaced from each other in the axial direction of the tester 1A. The worm gear or drive transmitting means 3b is interposed between the bearings 4. With this configuration, it is possible to reduce a thrust load. The center of gravity of the tester 1A should preferably be located between the bearings 4.

The tester 1A measures the tensile strength of a desired article 17. In the illustrative embodiment, the article 17 is assumed to be a screw member or nut 17 welded to a steel sheet.

The seat attachment 7 is formed with an axial bore 7a having an inside diameter D, and a hole 7b communicated to the bore 7a. The pull shaft 9 is loosely fitted in the hole 7b. The inside diameter D of the bore 7a is selected to be greater than the maximum outside diameter d of the screw member 17. When the tester 1A measures the tensile strength of the article 17, a seat surface 7c forming the bottom of the seat attachment 7 rests on the steel sheet 19 around the screw member 17. The attachment 7 therefore plays the role of a seat portion for allowing the tester 1A to be seated on the steel sheet 19 and to support the sheet 19. Various kinds of seat attachments 7 each having a particular inside diameter are prepared. This, coupled with the fact that the seat attachment 7 is removably mounted to the load transformer 6, allows the attachment 7 to be easily replaced with another seat attachment matching with the maximum diameter of the screw member 17. Further, because the seat attachment 7 is screwed into the load transformer 6, the former can be protruded from the latter to any desired position.

The pull shaft 9 is passed through the hole 7b of the seat attachment 7 coaxially with the attachment 7 and includes a shank 9b and the previously mentioned hexagonal head 9a greater in diameter than the shank 9b. The shank 9b has a threaded portion 9c at its end. When the threaded portion 9c is driven into the screw member 17, a torque applied to the drive plate 8 is transferred to the pull shaft 9 via the head 9a received in the hexagonal hole 8a of the drive plate 8.

The bore 3a of the sleeve 3 to which the drive plate 8 is fixed has a diameter greater than the maximum outside diameter of the head 9a of the pull shaft 9, so that the shaft 9a can be freely pulled out of the bore 3a.

When the motor 20 is energized, the rotation of the motor 20 is transmitted to the sleeve 3 via the drive shaft 14, worm 14a, and worm gear 3b. The resulting rotation of the sleeve 3 is transferred to the drive plate 8 and therefrom to the pull shaft 9. As a result, the pull shaft 9 exerts a tensile force corresponding to its rotation angle on the nut 17 via the head 9a, base 10, roller bearing 11, load transformer 6, and seat attachment while exerting a counterforce on the steel sheet 19.

The worm 14 and worm gear 3b playing the role of drive transmitting means allows even several tons of load to be applied to the nut 17 and allows the motor 20 to be reduced in size.

Various kinds of pull shafts 9 each having a threaded portion 9c of particular diameter are also prepared. Only if the plug 12 is removed from the knob 2, the pull shaft 9 can be pulled out of the hole 3a of the sleeve 3. Therefore, the pull shaft 9 can be easily replaced with another pull shaft matching with the diameter of the nut 17.

The roller bearing 11 mounted on the top of the load transformer 6 as a thrust bearing is highly durable even when subjected to a heavy load. The roller bearing 11 may be replaced with a ball bearing if the tester 1 is free from heavy loads. Further, use may be made of a tapered roller bearing.

The base 10 intervening between the thrust bearing 11 and the head 9a of the pull shaft 9 has a preselected substantial thickness. When the diameter of the head 9a is smaller than the maximum outside diameter of the thrust bearing 11, i.e., when the contact area between the head 9a and the bearing 11 is relatively small, the base 10 prevents a local load from acting on the bearing 11. Specifically, the thick base 10 implements the propagation of a stress at 45 degrees and thereby causes a load to act evenly on the thrust bearing 11. The base 10 therefore allows the head 9a to be reduced in size, enhancing a small size, light weight configuration.

The load transformer 6 is fixed to the bottom of the casing 5 and made up of a first flange 6d, a second flange 6a, a pressure sensing portion 6b intervening between the two flanges 6d and 6a, and four strain gauges 6c fitted on the circumference of the pressure sensing portion 6b at equally spaced locations. The first or lower flange 6d is fixed to the casing 5. The second or upper flange 6a abuts against the underside of the head 9a of the pull shaft 9 via the thrust bearing 11 and base 10. In this configuration, the load transformer 6 receives, as a compressive force, a counterforce derived from a tensile force generated in the shaft 9. The pressure sensing portion 6b is thin enough to elastically deform when subjected to the above compressive force. The strain gauges 6c measure the strain of the pressure sensing portion 6b when the compressive force acts on the portion 6b. As shown in FIG. 4, the strain gauges 6c are implemented as a bridge circuit and transform the strain to an electric signal for the measurement of the load. The thin configuration of the portion 6b not only enhances sensitivity, but also implements a space for arranging the strain gauges 6c.

The thin pressure sensing portion 6b intervening between the first and second flanges 6d and 6a constitutes a part of the casing 5. The strain gauges 6c fitted on the pressure sensing portion 6b measure a tensile force acting on the pull shaft 9 in terms of a strain (deformation) in the direction of thrust.

As shown in FIG. 19, the electric system 25 of the illustrative embodiment includes an amplifier 25a, an ADC 25b, a controller 26, a display 25c, and a switch 21. As shown in FIG. 20, the controller 26 may be implemented as a microcomputer and includes storing means 26a, comparing means 26b, counting means 26c, reverse rotation time determining means 26d, control signal generating means 26e, and mode switching means 26f. The storing means 26a is capable of storing one or both of a preselected reference tensile force and a measured tensile force. The comparing means 26b compares a tensile force measured by the strain gauges 6c with the reference tensile force stored in the storing means 26a. In addition, the comparing means 26b compares the measured value stored in the storing means 26a with a value measured by the strain gauges later. The counting means 26c counts the duration of rotation of the motor 20 based on the number of rotations. The reverse rotation time determining means 26d determines the duration of reverse rotation of the motor 20 on the basis of the output of the counting means 26c. The control signal generating means 26e sends a measurement start signal to the strain gauges 6c and sends a drive signal to the motor 20. The mode switching means 26f selects one of a breakage value mode, a strength value mode, and a peak value mode at a time. The breakage value mode, strength value mode and peak value mode are respectively represented by steps S5–S7, steps S8–S11, and steps S12–S17 shown in FIG. 29.

As shown in FIG. 29, the motor 20 is caused to start rotating at a low speed (step S1). On the elapse of a preselected period of time (Y, step S2), the counting means 26c is caused start counting (step S3). Subsequently, the motor 20 is caused to rotate at a high speed (step S4). In this condition, a tensile force is measured on the basis of an electric signal output from the strain gauges 6c and proportional to the tensile strength of the screw member (step S5). Then, whether or not the screw member has broken is determined on the basis of whether or not the output signal of the strain gauges 6c has sharply changed (step S6).

If the answer of the step S6 is positive (Y), then the measured value is displayed on the display 25c as a breakage value (step S7). The step S7 is followed by a step S18. If the answer of the step S6 is negative (N), a tensile force is measured on the basis of the electric signal output from the strain gauges 6c and proportional to the tensile strength of the screw member (step S8). The measured tensile strength is written to the storing means 26a (step S9). The measured tensile strength written to the storing means 26a is compared with the reference tensile strength (step S10). If the measured strength is greater than the reference strength (Y, step S10), then the measured value is displayed on the display 25c as a strength value (step S11). The step S11 is followed by a step S18.

If the answer of the step S10 is N, a tensile strength is again measured on the basis of an electric signal output from the strain gauges 6c (step S12). The measured strength is written to the storing means 26a (step S13). A tensile strength is gain measured (step S14) and compared with the measured strength stored in the storing means 26a (step S15). If the current measured value is greater than the last measured value (Y, step S15), then the measured value stored in the storing means 26a is replaced with the current measured value (step S16), and the program returns to the step S14. If the answer of the step S15 is N, then the stored value is displayed on the display 25c as a peak value (step S17). This is also followed by the step S18.

In the step S18, the drive torque for the motor 20 is reduced in order to reduce the load on the motor 20 in case the base material 19 and screw member 17 are abruptly broken up. Then, in a step S19, the motor 20 is deenergized for a moment. Subsequently, the counting means 26c started to operate in the step S3 is caused to stop operating (step 20). Subsequently, the motor 20 is rotated in the reverse direction over a period of time corresponding to the number of rotations counted by the counting means 26c (step S21). Thereafter, the motor 20 is deenergized (step S22).

The operation of the illustrative embodiment will be described hereinafter. Before operation, the pull shaft 9 whose threaded portion 9c corresponds in diameter to the nut 17 is mounted to the tester 1. Specifically, after the cap 13 and plug 12 have been sequentially removed from the knob 2, the pull shaft 9 is inserted into the hole 3a of the sleeve 3. After the head 9a of the pull shaft 9 has been received in the hexagonal hole 8a of the drive plate 8, the plug 12 is driven into the knob 2 until the end of the plug 12 abuts against the head 9a. In this condition, the pull shaft 9 is prevented from moving in the axial direction.

For measurement, the seat surface 7c of the seat attachment 7 is caused to rest on the steel sheet 19. Then, the motor 20 is caused to rotate at the low speed. The rotation of the motor 20 is transferred to the pull shaft 9 via the worm 14a, worm gear 3b, sleeve or drive shaft 3, and drive plate 8. As a result, the threaded portion 9c of the pull shaft 9 is driven into the nut 17. When the motor 20 is caused to rotate at the high speed, the rotation angle of the pull shaft 9 sequentially increases from the rotation angle at which the seat attachment 7 has abutted against the steel sheet 19. As a result, a force tending to pull the nut 17 out of the steel sheet 19 and proportional to the above rotation angle acts on the nut 17 due to the threaded engagement of the threaded portion 9c and nut 17. Because the seat attachment 7 fixed to the load transformer 6 has an inside diameter greater than the maximum diameter of the nut 17 and because the pull shaft 9 is coaxial with the attachment 7, the seat surface 7c automatically closely contacts the steel sheet 9 around the nut 17. The seat surface 7a therefore bears the counterforce of the pull shaft 9 via the load transformer 6, thrust bearing 11, base 10, and head 9a. A counterforce to act against the pulling force generated in the pull shaft 9 is transferred to the second flange 6d of the load transformer in the direction opposite to the above direction. Consequently, a compressive force equal, but opposite in direction, to the force pulling the nut 17 acts on the pressure sensing portion 6b. At this instant, the thrust bearing 11 serves to reduce the rotation load of the motor 20.

The tensile force generated in the pull shaft 9 compresses the pressure sensing portion 6b of the load transformer 6 in the axial direction. As a result an electric signal proportional to the tensile force acting on the nut 17 is sent from the strain gauges 6c to the electric system 25 via the intermediate terminals and wirings. The amplifier 25a amplifies the electric signal while the ADC 25b digitizes the amplified electric signal. The resulting digital value appears on the display 25c and allows the force tending to pull out the nut 17 to be read.

As stated above, in the illustrative embodiment, the electric system 25 measures the maximum tensile force, tensile strength and so forth of the screw member 17.

The tester 1 can adapt itself to the configuration and dimensions of the nut or screw member 17 only if the seat attachment 7 and pull shaft 9 are replaced with adequate ones, i.e., without resorting to the replacement of the knob 2. The tester 1 is therefore miniature and portable and makes it needless to cut out the nut portion from the steel sheet 19. Such a tester 1 can be used to measure a tensile strength to be measured at a work cited.

The pressure sensing portion 6b is implemented as a thin elastically deformable portion. This, coupled with the strain gauges 6c responsive to the deformation of the portion 6b, simplifies the construction and reduces the size of the tester 1. Moreover, because the wirings connecting the load transformer 6 to the electric system 25 is provided with a shield structure and arranged within the casing 5, the tester 1 is highly resistive to noise and prevents the wirings from being cut off during measurement. Consequently, not only reliable measurement but also easy operation are promoted.

The above embodiment prevents the pull shaft 9 from being loosened and allows it to be replaced easily and rapidly when the diameter of the article to be tested is changed or when the shaft 9 wears or is broken or otherwise damaged. In addition, the tester 1 can be positioned vertically by hand while guaranteeing the replaceability of the pull shaft 9. This insures the stable operation of the tester 1 despited that it is automatically driven by the motor 20.

The drive transmitting means is implemented by the worm 14a and worm gear 3b meshing with the worm 14a, so that even a small motor 20 can easily output a great torque. This enhances the free arrangement of the motor 20, i.e., allows it to be received in the grip 2.

As shown in FIG. 22A, the drive shaft 14 of the motor 20 and therefore the grip 2 is offset from the center of rotation of the sleeve 3. It is therefore easy to see the positional relation between the pull shaft 9 and the screw member 17 when the they are seen in the direction parallel to the grip 2.

The motor 20, worm 14a, worm gear 3b and grip 2 are positioned on a horizontal axis extending through the center of gravity G (see FIG. 15) of the tester 1. Therefore, the drive of the motor 20 and the rotation of the pull shaft 9 insure a stable holding ability. In addition, the center of gravity G is stabilized.

A thrust load is reduced because the sleeve 3 is supported by a plurality of bearings 4 axially spaced from each other and because the worm 14a and worm gear 3b are positioned between the bearings 4.

As shown in FIGS. 23A and 23B, the drive transmitting mans may be implemented as bevel gears 34a and 23b. With this arrangement, too, it is possible to locate the grip 2 on the horizontal line extending through the center of gravity in a simple construction.

The ON/OFF switch 21 assigned to the motor 20 is positioned in the vicinity of the body 5a of the grip 2. Therefore, even when the center of gravity G is deviated from the center of rotation due to an offset, a force exerted on the switch 21 for operating it acts at a position close to the center of gravity G. This reduces the influence of the above force on the body of the tester 1.

As shown in FIG. 23C, the drive shaft 14 may be connected to the worm 14a via a universal joint U. This, coupled with the fact that the grip 2 is located on a horizontal line extending though the center of rotation of the sleeve 3, reduces the deviation of the center of gravity G which would cause the body of the tester 1 to move.

As shown in FIG. 22B, a second grip 2B may extend out from the body 5a of the casing 5 at a position different from the grip 2. When the center of gravity G is displaced due to an offset, the second grip 2B reduces the movement of the body of the tester 1 and thereby enhances the holding ability. As shown in FIG. 22A, the switch 21 may be located at the opposite side to the grip 2 with respect to the axis of rotation K. This is also successful to prevent the body of the tester 1 from being displaced by a force exerted on the switch 21.

The second grip 2B is symmetrical in configuration to the grip 2 accommodating the motor 20 therein, so that the center of gravity G can be prevented from being displaced due to an offset.

The drive plate 8 with the hexagonal hole 8a mating with the hexagonal head 9a of the pull shaft 9 is fixed to the end of the sleeve 3 by the screws 16. Alternatively, the sleeve 3 may be provided with a bottom and have a hole (hexagonal hole) formed in the bottom. Of course, the hole may be provided with a configuration other than rectangle so long as it is capable of exerting a rotating force.

In the tensile strength tester shown in FIG. 30, the pull shaft 9 is rotated at a lower speed than during measurement for a preselected period of time since the start of rotation of the motor 20, so that the shaft 9 and screw member 17 can easily mate with each other. After the shaft 9 and screw member 17 have mated with each other, the pull shaft 9 is rotated at the speed assigned to measurement. Therefore, sure and stable mating is achievable despite the use of the motor or similar drive means 20, and the measurement is sped up.

Further, the rotation of the sleeve 3 can be transferred to the pull shaft 9 with a counterforce being absorbed at the portion where the sleeve 3 and shaft 9 are connected to each other. This prevents the connecting portion from being loosened.

With the storing means 26a, comparing means 26b and control signal generating means 26e, it is possible to measure a tensile strength on the basis of a reference value guaranteeing safety. The tester can therefore adapt itself to an article which should be estimated with respect to a certain set value. Because the article does not have to be broken, the screw member 17 is prevented from biting into the pull shaft 9.

Assume that the peak value or breakage value of the tensile strength is measured before the reference value stored in the storing means 26a is reached, the motor 20 is deenergized. This prevents the motor 20 from being wastefully driven when breakage occurs earlier than expected due to a short strength. Further, the motor 20 can be deenergized on the basis of the output of the comparing means 26b.

Because the peak value or breakage value appears on the display 25c, the tester can be brought to, e.g., a molding cite for measurement.

The tensile strength of an article can be determined only if a peak value is known. With the storing means 26a capable of storing the reference value and measured value, comparing means 26b for comparing them, and control signal generating means 26e capable of updating the measured value stored in the storing means 26a, it is possible to determine a peak value if the measured value is smaller than the stored value, and to use the stored value as a peak value.

After the peak value has appeared, the motor 20 is driven in the reverse direction and then deenergized. This facilitates the removal of the screw member 17 from the pull shaft 9. The easy removal of the screw member 17 is further promoted by the counting means 26c and reverse rotation time determining means 26d. After the appearance of the set value or peak value, the motor 20 is rotated in the reverse direction on the basis of a period of time determined by the reverse rotation determining means 26d.

FIG. 31 shows a fourth embodiment also using the motor drive scheme. This embodiment is identical with the fourth embodiment as to the motor drive and control section. As shown, a tensile strength tester, generally 1B includes a seat attachment 47 held in threaded engagement with the bottom of the load transformer 6. The seat attachment 47 includes a threaded portion 47b threaded in the opposite direction to the threaded portion 9c of the pull shaft 9. The seat attachment 47 additionally includes an irregular portion or abutment 7h against which a broken nut 17 will abut. Further, the lower end portion of the seat attachment including a seat surface 47c is magnetized.

The pull shaft 9 has such a length that its bottom is positioned above the bottom of the seat attachment 7, i.e., the seat surface 7c.

A regulating member 41 abuts against the cap 13 at its one end and regulates the position of the pull shaft 9 such that the head 9a of the shaft 9 does not slip out of the hexagonal hole of the drive plate 8. A spring 42 is loaded between the regulating member 41 and the pull shaft 9 so as to constantly bias the shaft 9 downward. The spring 42 may be replaced with any other suitable elastic member, e.g., one formed of rubber.

Figure 32A:
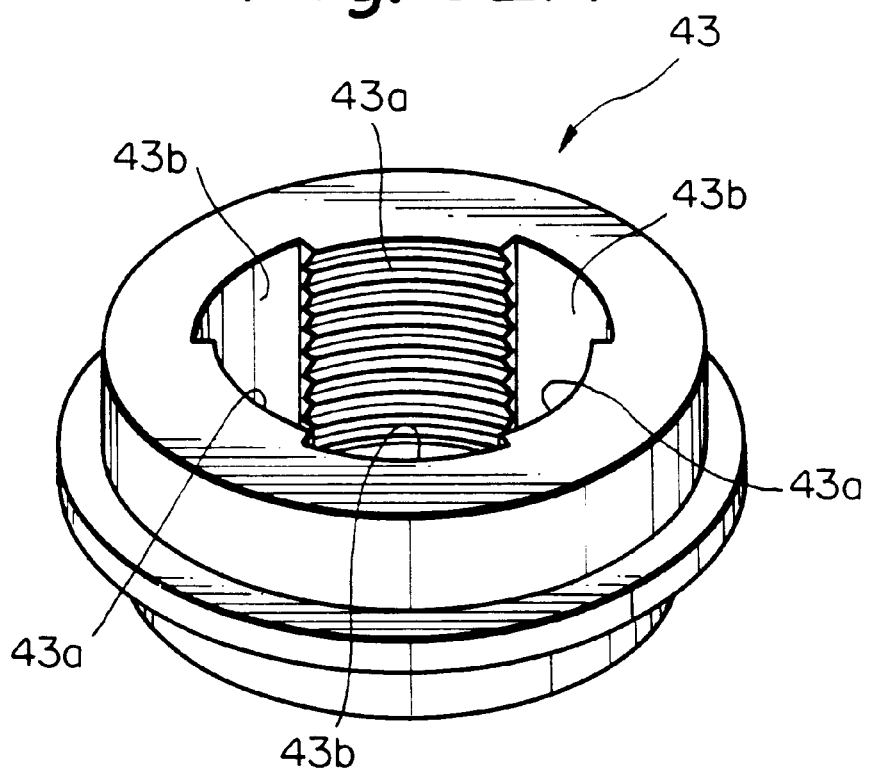
FIG. 32A is a perspective view showing a member with which a seat attachment is capable of mating.
Figure 32B:
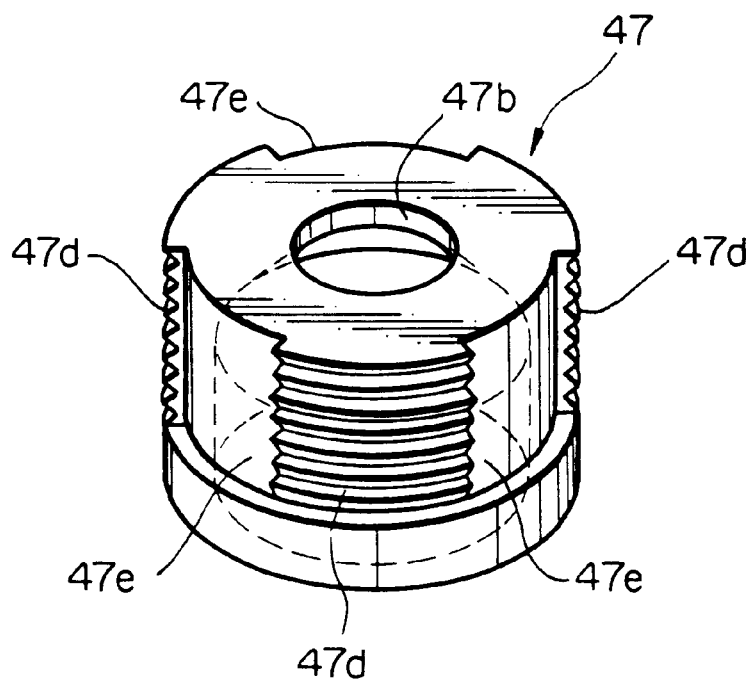
FIG. 32B is a perspective view of the seat attachment.
Figure 32C:
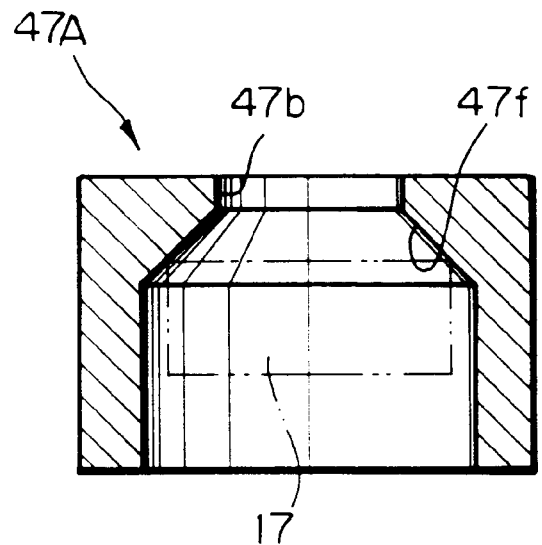
FIGS. 32C and 32D are sections each showing a particular modification of the seat attachment.
Figure 32D:
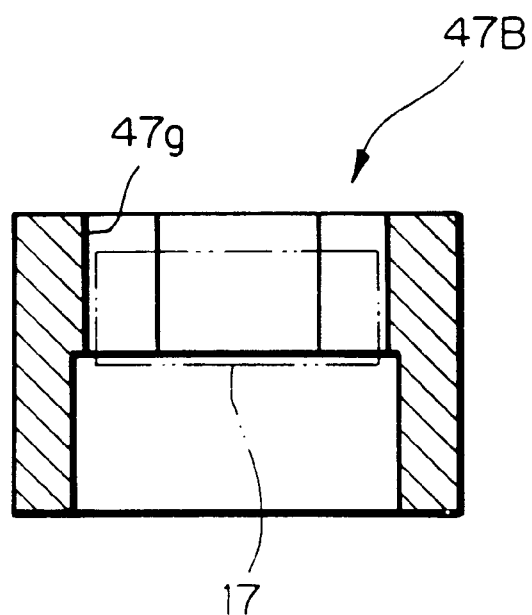

FIG. 32A shows an annular fixing member 43 interposed between the body 5a of the casing 5 and the seat attachment 47 and press fitted in the body 5a. The fixing member 43 has threaded portions 43a at equally spaced locations on its inner circumference. Threaded portions 6e and 47d included in the load transformer 6 and seat attachment 47, respectively, are engaged with the threaded portions 43a. As shown in FIG. 32B, the seat attachment 47 is formed with a hole 47b through which the pull shaft 9 is loosely passed. Threaded portions 47d capable of engaging with the threaded portions 43a are formed at equally spaced located on the outer circumference of the seat attachment 47. The fixing member 43 and seat attachment 47 are rotatable about their axis to a desired relative position. As shown in FIG. 32C, the seat attachment 47 with the irregular portion 47h may be replaced with a seat attachment 47A including a tapered portion or abutment 47f. Further, as shown in FIG. 32D, use may be made of a seat attachment 47B formed with, e.g., a hexagonal hole 47g.

As stated above, in each of the third and fourth embodiments, a force tending to pull the screw member 17 out of the base material 19 is applied to the pull shaft 9 in order to measure the tensile strength of the screw member 17. Because the seat attachment 7 or 47 abutting against the base material 19 is held in threaded engagement with the casing body 5a and/or the pressure sensing portion 6b, the attachment 7 or 47 can be turned in order to adjust the height. At the time when the pull shaft 9 is brought into contact with and screwed into the screw member 17, the seat attachment 7 or 47 rests on the base material 29. This prevents the tester from shaking and insures stable drive of the pull shaft 9 into the screw member 17. The seat attachment 7 or 47 is easy to replace because it is mounted by the thread scheme.

Because the threaded portions 7d or 47d of the seat attachment 7 or 47, respectively, are opposite in direction to the threaded portion 9c of the pull shaft 9, the threaded portions 7d or 47d and the threaded portion 9c are prevented from being rotated together.

The lower end of the pull shaft 9 is positioned above or inward of the lower end of the seat attachment 7 or 47. Such a position of the pull shaft 9 promotes easy adjustment and reduces the span, i.e., the length for adjustment, so that the pull shaft 9 can be easily set on the base material 19.

The abutment 7h or 47h included in the seat attachment 7 or 47 for stopping the screw member 17 allows the bottom of the attachment 7 or 47 to be magnetically attracted by the base material 19 when and after the attachment 7 or 47 has been brought into contact with the base material 19. This promotes accurate setting of the seat attachment 7 on the base material 19.

Because at least the lower end portion of the seat attachment 7 or 47 is magnetized, the bottom of the attachment 7 or 47 is magnetically attracted by the base material 19 when and after the attachment 7 or 47 has been brought into contact with the base material 19. This promotes accurate setting of the seat attachment 7 on the base material 19.

The inner periphery of the seat attachment 7 or 47 is engageable with the outer periphery of the screw member 17 at least in the direction of rotation. Therefore, by turning the seat attachment 7 or 47, it is possible to remove the screw member 17 from the pull shaft 9.

The threaded portions 7d or 47d of the seat attachment 7 or 47, respectively, are positioned at equally spaced locations along the circumference, and so are done the threaded portions 43a of the fixing member 43 (threaded portions of the load transformer 6). The seat attachment 7 or 47 and the body 5a of the casing 5 are removable from each other in the axial direction in accordance with the angle of rotation. That is, the seat attachment 7 or 47 and the body 5a or load transformer 6 are removable from each other in the axial direction. This allows the seat attachment 4 or 47 to be rapidly moved upward or downward to a desired height.

The elastic member 42 elastically retains the head 9a of the pull shaft 9 via the cap 13. When the screw member 17 abuts against the pull shaft 9, the shaft 9 is allowed to draw back due to the elastic member 42. As a result, a shock ascribable to the abutment is absorbed, so that the pull shaft 9 can surely mate with the screw member 17. The pull shaft 9 draws back by an amount allowing the seat attachment 7 or 47 to contact the base material 19. At the same time, the regulating member 41a regulates the above withdrawal of the pull shaft 9.

When the measured value is greater than the reference value, the former is substituted for the latter and stored as a new reference value. If the stored value is greater than the next measured value, it is displayed as a peak value while the drive torque of the motor 20 is reduced. This allows a peak to be measured and reduces, at the time of an abrupt breakage, the load to act on the motor 20.

Because the motor 20 is rotated in the reverse direction and then deenergized, the screw member 17 is easily removed from the pull shaft 9.

Figure 25:
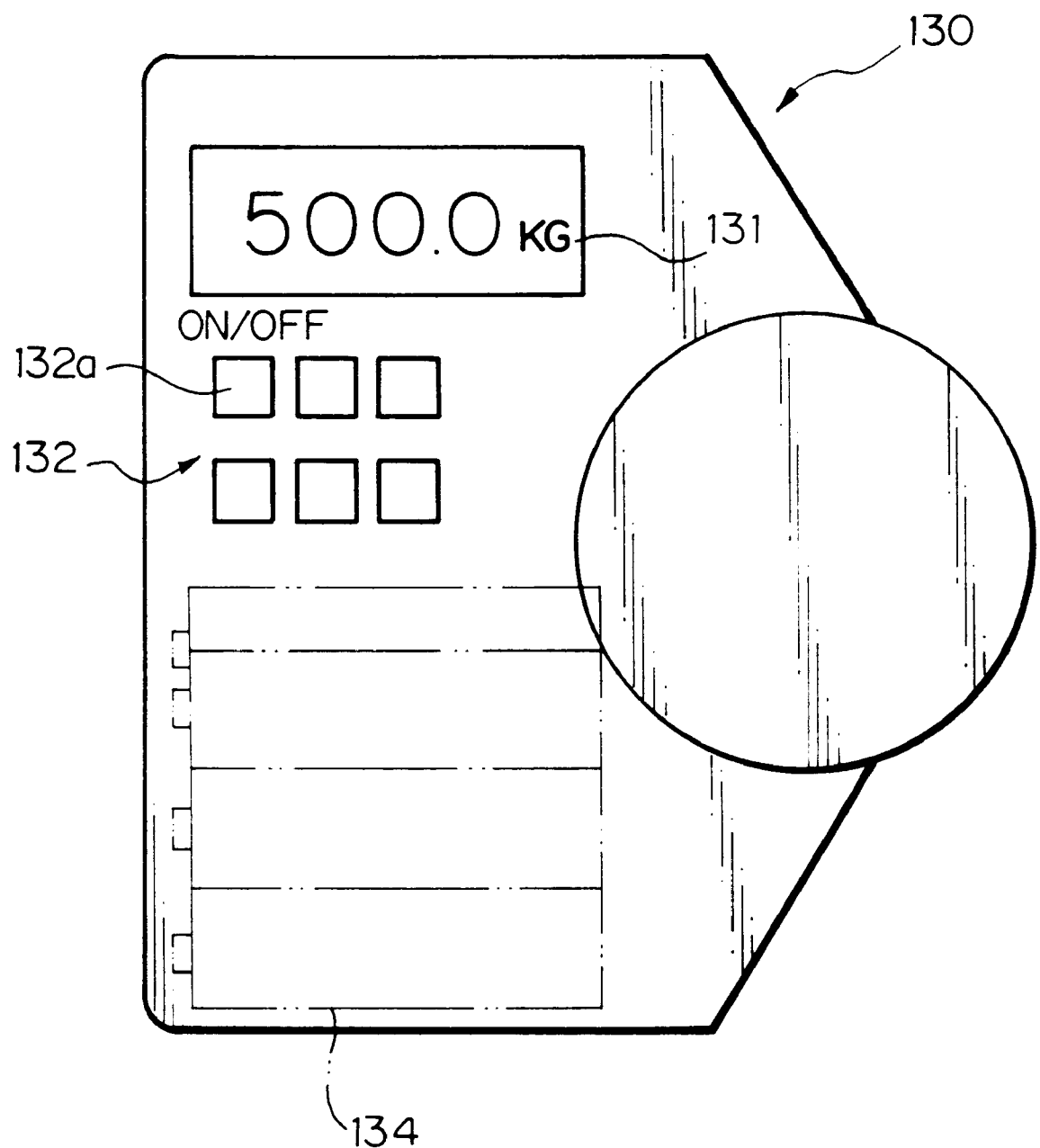
FIG. 25 is a top view of the embodiment shown in FIG. 24.

As shown in FIG. 25, the electric signal output from the strain gauges 26 is amplified and then digitized. As a result, a peak value constantly appears on the display 131. The display 131 includes a mode selection switch for selecting one of the set mode (A), peak value mode (B) and breakage value mode (C) at a time. In the set mode (A), at least a set value and a measured value appear on the display 131. In the peak value mode (B), at least a peak value appears on the display 131. In the breakage value mode (C), at least a breakage value appears on the display 131. Of course, this kind of display is similarly applicable to the embodiments using the manual drive scheme.

As shown in FIG. 30, the seat attachment 7 is held in threaded engagement with the bottom of the load transformer 6. The seat attachment 7 includes the threaded portion 7b threaded in the opposite direction to the threaded portion 9c of the pull shaft 9. The seat attachment 7 additionally includes an irregular portion or abutment 7h against which a broken nut 17 will abut. Further, the lower end portion of the seat attachment including the seat surface 47c is magnetized.

The pull shaft 9 has such a length that its bottom is positioned above the bottom of the seat attachment 7, i.e., the seat surface 7c. At least the bottom portion of the pull shaft 9 is magnetized.

In the tensile strength tester shown in FIG. 30, the pull shaft 9 is rotated at a lower speed than during measurement for a preselected period of time since the start of rotation of the motor 20, so that the shaft 9 and screw member 17 can easily mate with each other. After the shaft 9 and screw member 17 have mated with each other, the pull shaft 9 is rotated at the speed assigned to measurement. Therefore, sure and stable mating is achievable despite the use of the motor or similar drive means 20, and the measurement is sped up.

Further, the rotation of the sleeve 3 can be transferred to the pull shaft 9 with a counterforce being absorbed at the portion where the sleeve 3 and shaft 9 are connected to each other. This prevents such a connecting portion from being loosened.

With the storing means 26a, comparing means 26b and control signal generating means 26e, it is possible to measure a tensile strength on the basis of a reference value guaranteeing safety. The tester can therefore adapt itself to an article which should be estimated with respect to a certain set value. Because the article does not have to be broken, the screw member 17 is prevented from biting into the pull shaft 9.

When the peak value or breakage value of the tensile strength is measured before the reference value stored in the storing means 26a is reached, the motor 20 is deenergized. This prevents the motor 20 from being wastefully driven in the event of the previously stated occurrence. Further, the motor 20 can be deenergized on the basis of the output of the comparing means 26b.

Because the peak value or breakage value appears on the display 25c, the tester can be brought to, e.g., a molding cite for measurement.

The tensile strength of an article can be determined only if a peak value is known. With the storing means 26a capable of storing the reference value and measured value, comparing means 26b for comparing them, and control signal generating means 26e capable of updating the measured value stored in the storing means 26a, it is possible to determine a peak value if the measured value is smaller than the stored value, and to use the stored value as a peak value.

After the peak value has appeared, the motor 20 is driven in the reverse direction and then deenergized. This facilitates the removal of the screw member 17 from the pull shaft 9. The easy removal of the screw member 17 is further promoted by the counting means 26c and reverse rotation time determining means 26d. After the appearance of the set value or peak value, the motor 20 is rotated in the reverse direction on the basis of a period of time determined by the reverse rotation determining means 26d.

Figure 33:
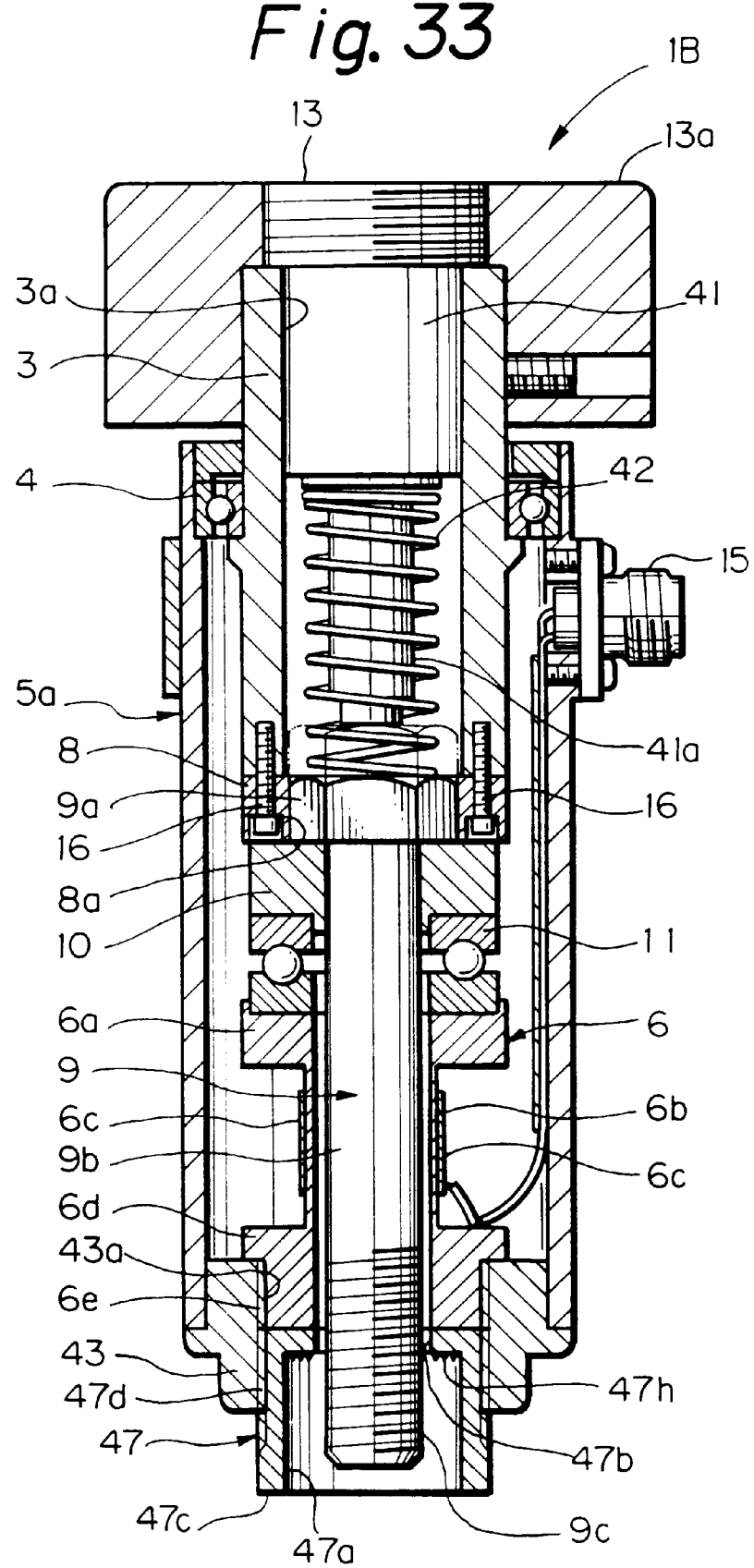
FIG. 33 is a sectional front view showing a fifth motor drive type embodiment of the tensile strength tester in accordance with the present invention.

FIG. 33 shows a fifth embodiment using the motor drive scheme. As shown, a tensile strength tester includes a seat attachment 47 held in threaded engagement with the bottom of the load transformer 6. The seat attachment 47 includes a threaded portion 47b threaded in the opposite direction to the threaded portion 9c of the pull shaft 9. The seat attachment 47 additionally includes an irregular portion or abutment 7h against which a broken nut 17 will abut. Further, the lower end portion of the seat attachment including a seat surface 47c is magnetized.

The pull shaft 9 has such a length that its bottom is positioned above the bottom of the seat attachment 7, i.e., the seat surface 7c.

A regulating member 41 abuts against the cap 13 at its one end and regulates the position of the pull shaft 9 such that the head 9a of the shaft 9 does not slip out of the hexagonal hole of the drive plate 8. A spring 42 is loaded between the regulating member 41 and the pull shaft 9 so as to constantly bias the shaft 9 downward. The spring 42 may be replaced with any other suitable elastic member, e.g., one formed of rubber.

FIG. 32A shows an annular fixing member 43 interposed between the body 5a of the casing 5 and the seat attachment 47 and press fitted in the body 5a. The fixing member 43 has threaded portions 43a at equally spaced locations on its inner circumference. Threaded portions 6e and 47d included in the load transformer 6 and seat attachment 47, respectively, are engaged with the threaded portions 43a. As shown in FIG. 32B, the seat attachment 47 is formed with a hole 47b through which the pull shaft 9 is loosely passed. Threaded portions 47d capable of engaging with the threaded portions 43a are formed at equally spaced located on the outer circumference of the seat attachment 47. The fixing member 43 and seat attachment 47 are rotatable about their axis to a desired relative position. As shown in FIG. 32C, the seat attachment 47 with the irregular portion 47h may be replaced with a seat attachment 47A including a tapered portion or abutment 47f. Further, as shown in FIG. 32D, use may be made of a seat attachment 47B formed with, e.g., a hexagonal hole 47g.

Figure 34:
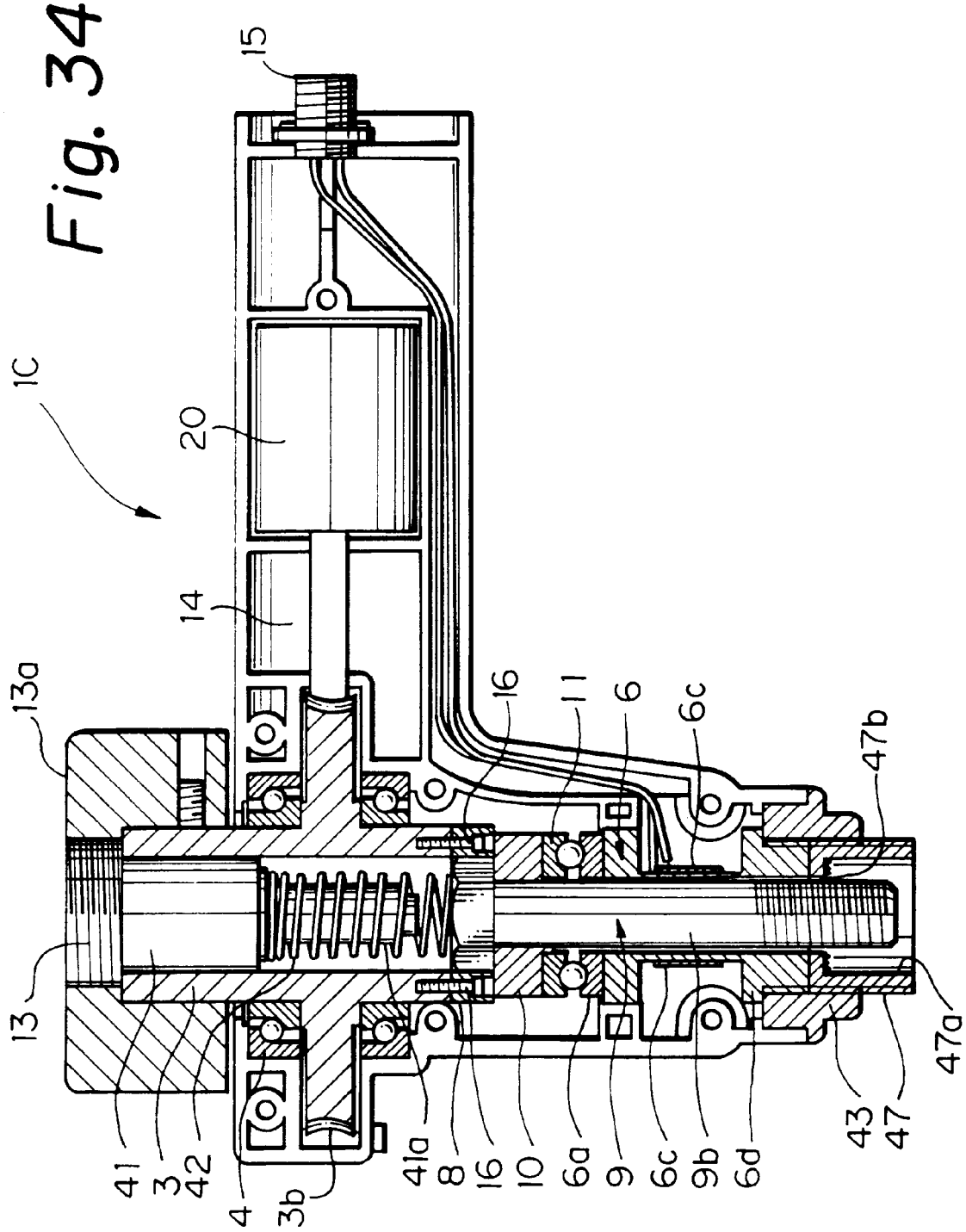
FIG. 34 is a sectional front view showing a sixth motor drive type embodiment of the tensile strength tester in accordance with the present invention.

FIG. 34 shows a sixth embodiment using the motor drive scheme. As shown, a tensile strength tester, generally 1C, is identical with the tester 1B representative of the fourth embodiment except that the motor drive and control section of the tester 1A representative of the third embodiment is applied thereto.

As stated above, in the above tensile strength tester, a force tending to pull the screw member 17 out of the base material 19 is applied to the pull shaft 9 in order to measure the tensile strength of the screw member 17. Because the seat attachment 7 or 47 abutting against the base material 19 is held in threaded engagement with the drum 5a and/or the pressure sensing portion 6b, the attachment 7 or 47 can be turned in order to adjust the height. At the time when the pull shaft 9 is brought into contact with and screwed into the screw member 17, the seat attachment 7 or 47 rests on the base material 29. This prevents the tester from shaking and insures stable drive of the pull shaft 9 into the screw member 17. The seat attachment 7 or 47 is easy to replace because it is mounted by the thread scheme.

Because the threaded portions 7d or 47d of the seat attachment 7 or 47, respectively, are opposite in direction to the threaded portion 9c of the pull shaft 9, the threaded portions 7d or 47d and the threaded portion 9c are prevented from being rotated together.

The lower end of the pull shaft 9 is positioned above or inward of the lower end of the seat attachment 7 or 47. Such a position of the pull shaft 9 promotes easy adjustment and reduces the span, i.e., the length for adjustment, so that the pull shaft 9 can be easily set on the base material 19.

The abutment 7h or 47h included in the seat attachment 7 or 47 for stopping the screw member 17 allows the bottom of the attachment 7 or 47 to be magnetically attracted by the base material 19 when and after the attachment 7 or 47 has been brought into contact with the base material 19. This promotes accurate setting of the seat attachment 7 on the base material 19.

Because at least the lower end portion of the seat attachment 7 or 47 is magnetized, the bottom of the attachment 7 or 47 is magnetically attracted by the base material 19 when and after the attachment 7 or 47 has been brought into contact with the base material 19. This promotes accurate setting of the seat attachment 7 on the base material 19.

The inner periphery of the seat attachment 7 or 47 is engageable with the outer periphery of the screw member 17 at least in the direction of rotation. Therefore, by turning the seat attachment 7 or 47, it is possible to remove the screw member 17 from the pull shaft 9.

The threaded portions 7d or 47d of the seat attachment 7 or 47, respectively, are positioned at equally spaced locations along the circumference, and so are done the threaded portions 43a of the fixing member 43 (threaded portions of the load transformer 6). The seat attachment 7 or 47 and the body 5a of the casing 5 are removable from each other in the axial direction in accordance with the angle of rotation. That is, the seat attachment 7 or 47 and the body 5a or load transformer 6 are removable from each other in the axial direction. This allows the seat attachment 4 or 47 to be rapidly moved upward or downward to a desired height.

The tensile strength tester shown in FIG. 30 is easy to set for the following reasons. A force tending to pull the screw member 17 out of the base material 19 is applied to the pull shaft 9 in order to measure the tensile strength of the screw member 17. Because the seat attachment 7 or 47 abutting against the base material 19 is held in threaded engagement with the drum 5a and/or the pressure sensing portion 6b, the attachment 7 or 47 can be turned in order to adjust the height. At the time when the pull shaft 9 is brought into contact with and threaded into the screw member 17, the seat attachment 7 or 47 rests on the base material 29. This prevents the tester from shaking and insures stable drive of the pull shaft 9 into the screw member 17. The seat attachment 7 or 47 is easy to replace because it is mounted by the thread scheme.

Because the threaded portions 7d or 47d of the seat attachment 7 or 47, respectively, are opposite in direction to the threaded portion 9c of the pull shaft 9, the threaded portions 7d or 47d and the threaded portion 9c are prevented from being rotated together.

The lower end of the pull shaft 9 is positioned above or inward of the lower end of the seat attachment 7 or 47. Such a position of the pull shaft 9 promotes easy adjustment and reduces the span, i.e., the length for adjustment, so that the pull shaft 9 can be easily set on the base material 19.

The abutment 7h or 47h included in the seat attachment 7 or 47 for stopping the screw member 17 allows the bottom of the attachment 7 or 47 to be magnetically attracted by the base material 19 when and after the attachment 7 or 47 has been brought into contact with the base material 19. This promotes accurate setting of the seat attachment 7 on the base material 19.

Because at least the lower end portion of the seat attachment 7 or 47 is magnetized, the bottom of the attachment 7 or 47 is magnetically attracted by the base material 19 when and after the attachment 7 or 47 has been brought into contact with the base material 19. This promotes accurate setting of the seat attachment 7 on the base material 19.

The inner periphery of the seat attachment 7 or 47 is engageable with the outer periphery of the screw member 17 at least in the direction of rotation. Therefore, by turning the seat attachment 7 or 47, it is possible to remove the screw member 17 from the pull shaft 9.

The threaded portions 7d or 47d of the seat attachment 7 or 47, respectively, are positioned at equally spaced locations along the circumference, and so are done the threaded portions 43a of the fixing member 43 (threaded portions of the load transformer 6). The seat attachment 7 or 47 and the body 5a of the casing 5 are removable from each other in the axial direction in accordance with the angle of rotation. That is, the seat attachment 7 or 47 and the body 5a or load transformer 6 are removable from each other in the axial direction. This allows the seat attachment 4 or 47 to be rapidly moved upward or downward to a desired height.

Figure 35:
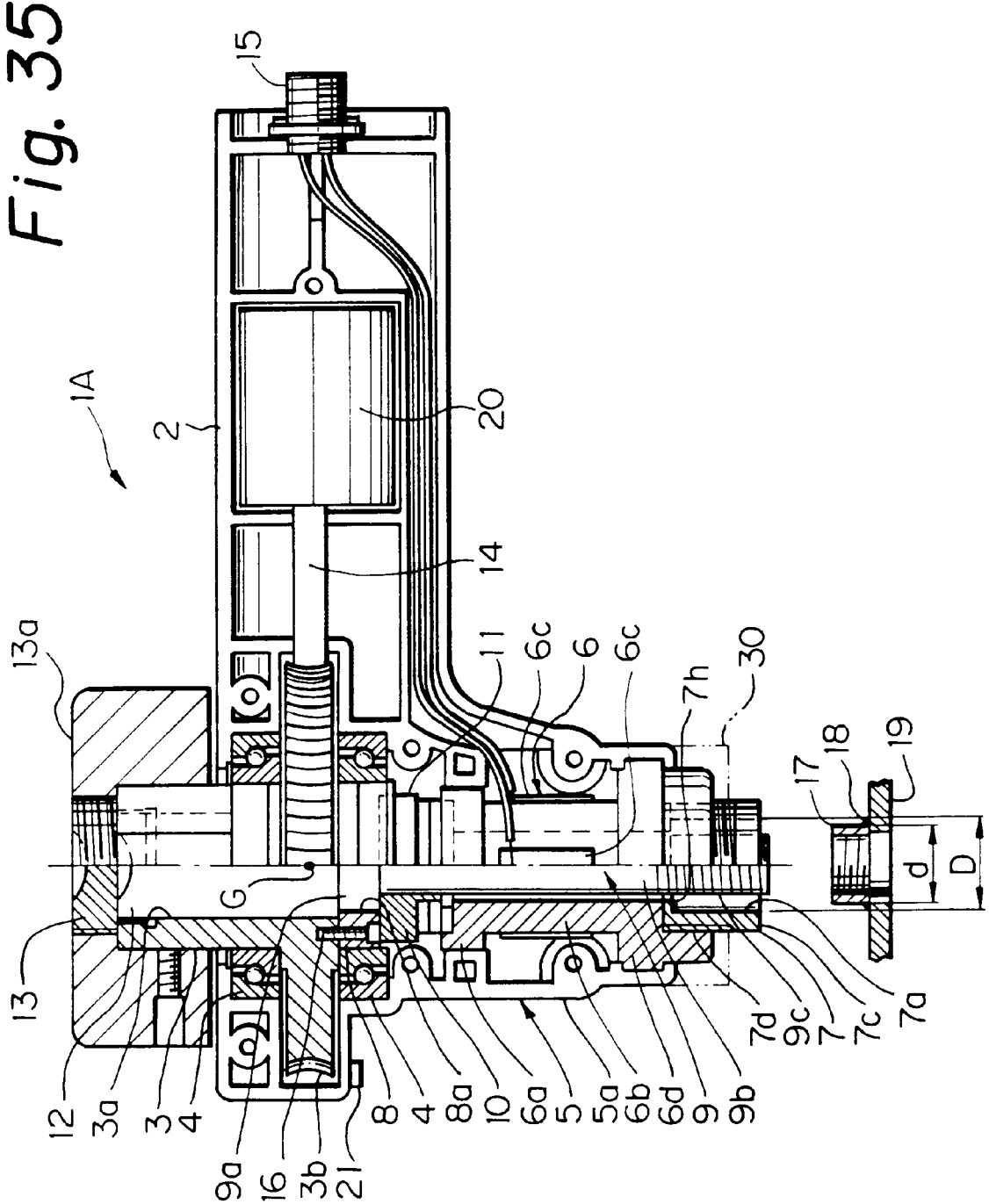
FIG. 35 is a sectional front view showing the embodiment of FIG. 30.

FIG. 35 shows a tensile strength tester constructed to promote easy removal of the screw member or nut 17. As shown, an attachment drive motor 30 is mounted on, e.g., the lower end of the body 5a of the casing 5. The motor 30 drives the seat attachment 7 in the up-and-down direction toward or away from the base material 19.

Figure 36:
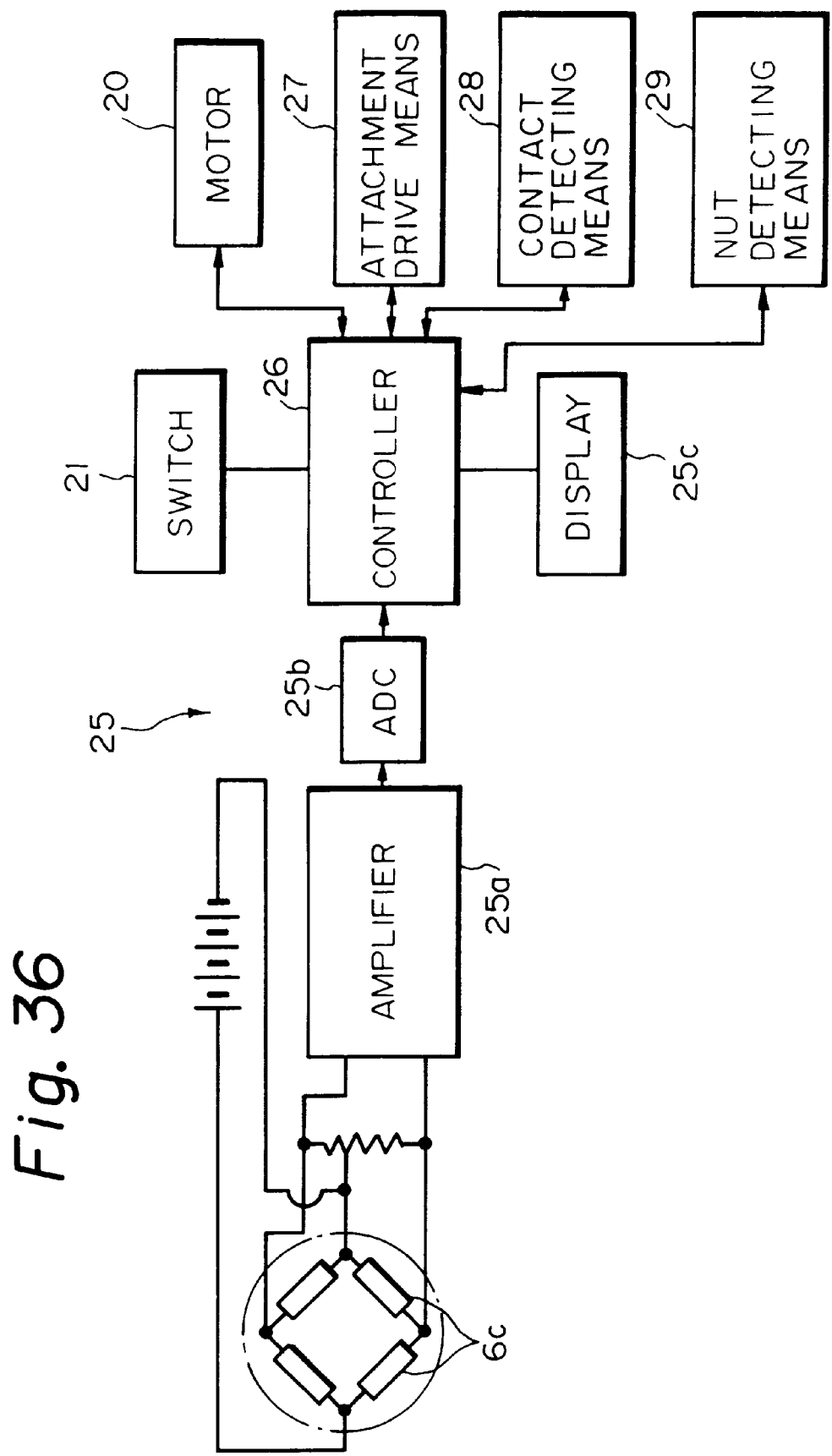
FIG. 36 is a block diagram showing an electric system particular to the embodiment of FIG. 30.

FIG. 36 shows an electric system 25 particular to the tester of FIG. 35. As shown, the electric system 25 includes attachment drive means 27, contact detecting means 28 and nut detecting means 29 as well as an amplifier 25a, an ADC 25b, a controller 26, and a display 25c. The attachment drive means 27 includes the motor 30, FIG. 35, and selectively drives the seat attachment 7 in the forward direction or the reverse direction substantially coaxially with the pull shaft 9. The rotation of the motor 30 may also be transferred to the seat attachment 7 via a worm gear device. The contact detecting means 28 detects the contact of the seat attachment 7 with the base material 19 on the basis of a change in the torque of the motor 30. Alternatively, a voltage may be applied between the seat attachment 27 and the base material 19 in order to cause a small current to flow due to electrical conduction. The nut detecting means 27 determines whether or not the nut 17 has fully entered the gap between the seat attachment 7 and the pull shaft 9.

Figure 37:
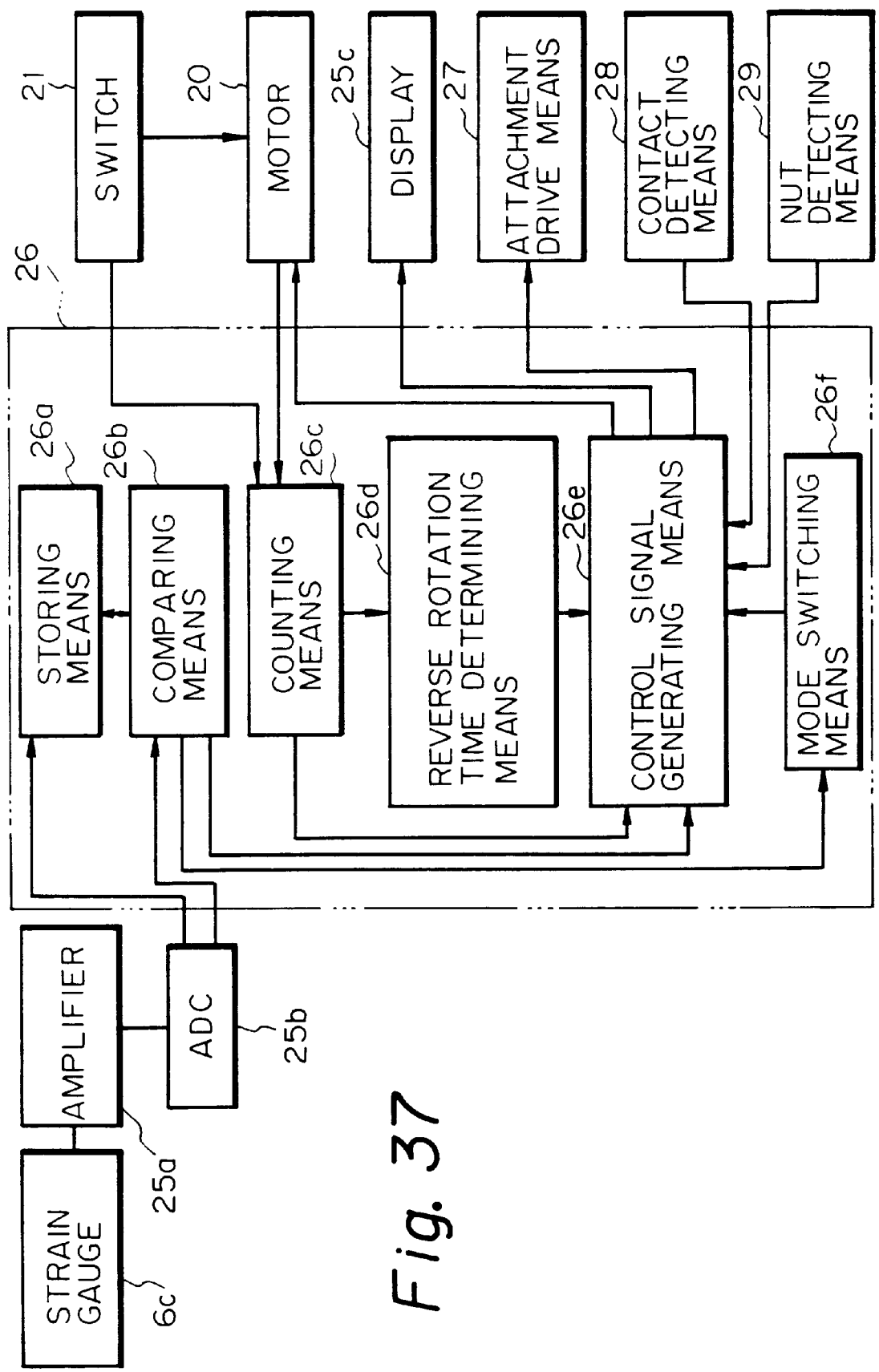
FIG. 37 is a schematic block diagram showing a controller included in the electric system of FIG. 36.

As shown in FIG. 37, the controller 26 may be implemented as a microcomputer and includes storing means 26a, comparing means 26b, counting means 26c, reverse rotation time determining means 26d, control signal generating means 26e, and mode switching means 26f. The storing means 26a is capable of storing one or both of a preselected reference tensile force and a measured tensile force. The comparing means 26b compares a tensile force measured by the strain gauges 6c with the reference tensile force stored in the storing means 26a. In addition, the comparing means 26b compares the measured value stored in the storing means 26a with a value measured by the strain gauges later. The counting means 26c counts the duration of rotation of the motor 20 based on the number of rotations. The reverse rotation time determining means 26d determines the duration of reverse rotation of the motor 20 on the basis of the output of the counting means 26c. The control signal generating means 26e sends a measurement start signal to the strain gauges 6c and sends a drive signal to the motor 20. The mode switching means 26f selects one of a breakage value mode, a strength value mode, and a peak value mode at a time. The breakage value mode, strength value mode and peak value mode are respectively represented by steps S7–S9, steps S12–S15, and steps S16–S21 shown in FIG. 38.

Figure 38B:
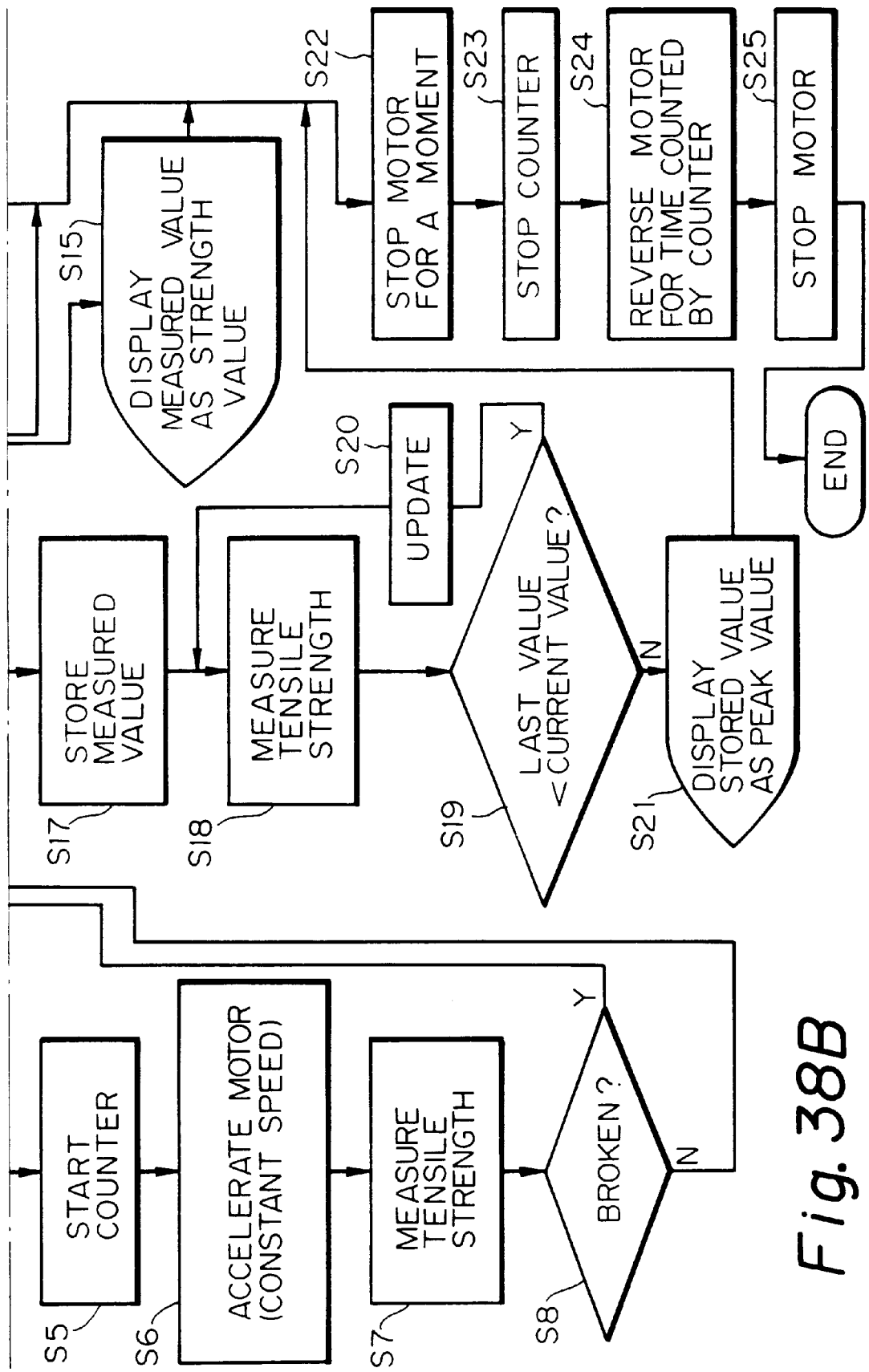
FIG. 38 is a flowchart demonstrating the operation of the embodiment of FIG. 30.
Figure 39A:
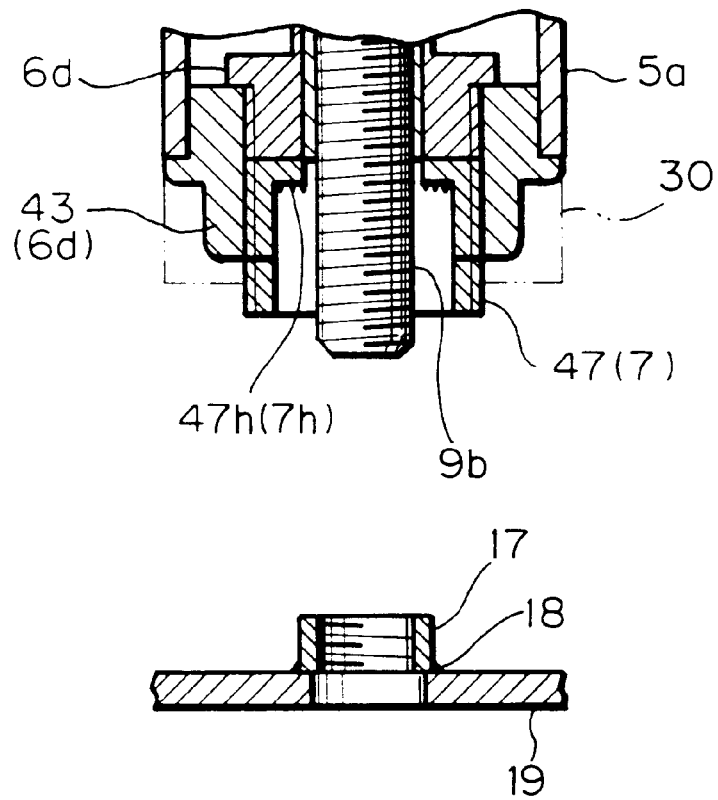
FIGS. 39A–39D are sections showing consecutive conditions occurring in accordance with the operation shown in FIG. 38.
Figure 39B:
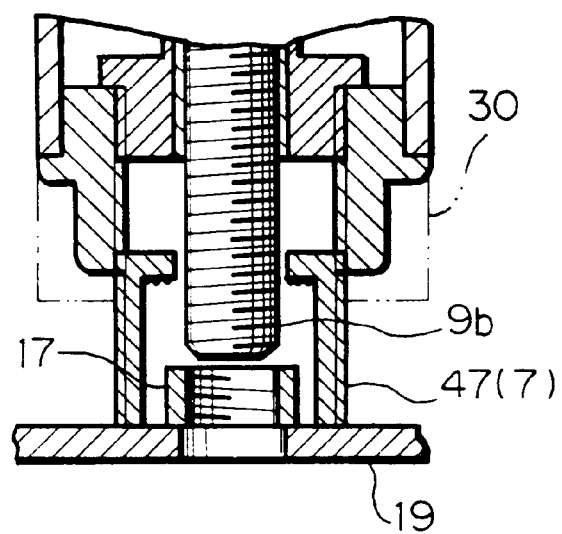
Figure 39C:
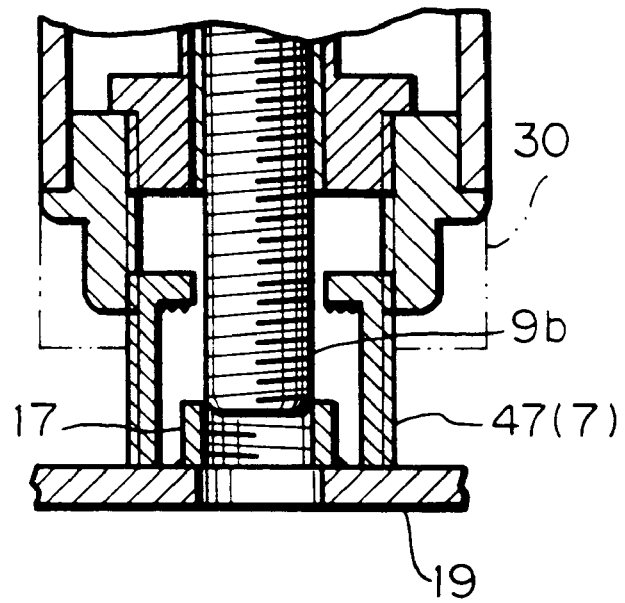
Figure 39D:
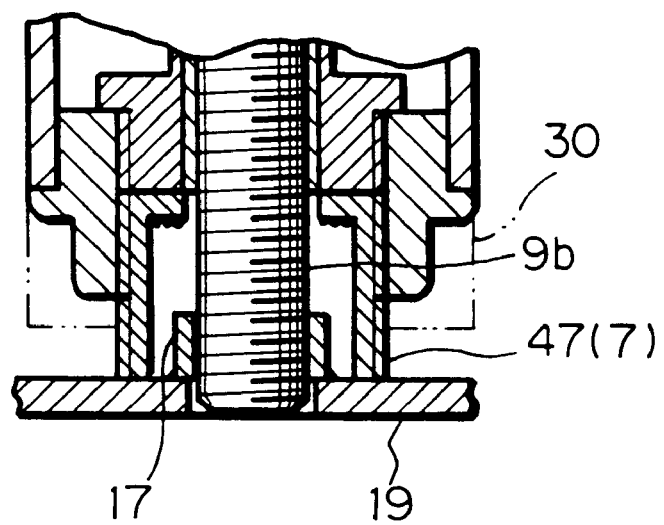

As shown in FIG. 38, the attachment drive motor 30 is energized first (step S1). As a result, the seat attachment 7 is caused to protrude, as shown in FIG. 39A. When the seat attachment 7 is brought into contact with the base material 19, as shown in FIG. 39B, the motor 30 is deenergized (step S2). Then, the motor 20 is energized and caused to rotate at a low speed for a preselected period of time (step S3). When the preselected period of time elapses (Y, step S4), the threaded portion 9b of the pull shaft 9 starts mating with the nut 17, as shown in FIG. 39C. At this time, the counting means 26c is caused to start counting (step S5). Subsequently, the motor 20 is caused to rotate at a high speed (step S6) in the condition shown in FIG. 39D. A tensile force is measured on the basis of the resulting electric signal output from the strain gauges 6c and proportional to the tensile strength of the screw member (step S7). Then, whether or not the screw member has broken is determined on the basis of whether or not the output signal of the strain gauges 6c has sharply changed (step S8).

If the answer of the step S8 is Y, then the measured value is displayed on the display 25c as a breakage value (step S9).

The step S9 is followed by a step S10. In the step S10, whether or not the screw member or nut 17 has been fully received in the gap between the seat attachment 7 and the pull shaft 9 is determined on the basis of the output of the nut detecting means 29. If the answer of the step S10 is Y, then the seat attachment 7 is rotated in the protruding direction while the pull shaft 9 is rotated in the opposite direction to the attachment 7 (step S11). If the answer of the step S10 is N, then a step S22 is executed.

On the other hand, if the answer of the step S8 is N, a tensile force is measured on the basis of the electric signal output from the strain gauges 6c and proportional to the tensile strength of the screw member (step S12). The measured tensile strength is written to the storing means 26a (step S13). The measured tensile strength written to the storing means 26a is compared with the reference tensile strength (step S14). If the measured strength is greater than the reference strength (Y, step S14), then the measured strength is displayed on the display 25c as a strength value (step S15). The step S11 is followed by the step step S22.

If the answer of the step S14 is N, a tensile strength is again measured on the basis of an electric signal output from the strain gauges 6c (step S16). The measured strength is written to the storing means 26a (step S13). A tensile strength is gain measured (step S14) and compared with the measured strength stored in the storing means 26a (step S17). Then, a tensile strength is gain measured (step S18). The measured value is compared with the measured value stored in the storing means 26a in the step S17 (step S19). If the current measured value is greater than the last measured value (Y, step S19), then the measured value stored in the storing means 26a is replaced with the current measured value (step S20), and the program returns to the step S18. If the answer of the step S19 is N, then the stored value is displayed on the display 25c as a peak value (step S21). This is also followed by the step S22.

In the step S22, the motor 20 is deenergized for a moment. Subsequently, the counting means 26c started to operate in the step S5 is caused to stop operating (step 23). Subsequently, the motor 20 is rotated in the reverse direction over a period of time corresponding to the number of rotations counted by the counting means 26c (step S24). Thereafter, the motor 20 is deenergized (step S25).

As stated above, the pull shaft 9 is driven when the contact detecting means 28 detects the contact of the seat attachment 7 or 47 with the base material 19. This allows the pull shaft 9 to mate with the screw member 17 stably. Because the contact detecting means 28 detects the contact on the basis of a change in the torque of the attachment drive motor 30, stable mating is further promoted.

In summary, it will be seen that the present invention provides a tensile strength tester having various unprecedented advantages, as enumerated below.

(1) The tester can be held in its vertical position by hand while allowing a pulling member to be replaced from above the tester. The tester can therefore be automatically and stably driven by a motor.

(2) A great torque is achievable with a small motor. The motor can therefore be arranged at a desired position, e.g., within the tester.

(3) Because a grip included in the tester is offset, the positional relation between the pulling member and an article to be tested can be easily seen, particularly in the direction parallel to the grip.

(4) The tester can be stably held because of the drive of the drive means and the rotation of the pulling member. In addition, the center of gravity of the tester is stabilized.

(5) A minimum of thrust load occurs.

(6) The drive means and grip can be arranged on a horizontal line extending through the center of gravity by a simple configuration.

(7) Even when the center of gravity is deviated from the center of rotation due to an offset, a force pressing a switch acts at a position close to the center of gravity because the switch adjoins the body portion of the grip. The above force therefore has a minimum of influence on the body of the tester.

(8) The grip located at the above position reduces the deviation of the center of gravity and frees the tester from movement ascribable to the deviation. In addition, the tester can be stably held.

(9) The deviation of the center of gravity ascribable to an offset is obviated.

Various modifications will become possible for those skilled in the art after receiving the teachings of the present disclosure without departing from the scope thereof.

What is claimed is:

1. A tensile strength tester for applying a tensile force tending to pull a screw member fitted in a base material out of said base material to thereby measure a tensile strength in terms of said tensile force, said tensile strength tester comprising:

casing means for seating said tester on the base material;

pulling means for exerting a tensile force on the screw member, said pulling means including a first end having a threaded portion capable of mating with said screw member, and a first connecting portion positioned at a second end opposing said first end in an axial direction; and rotating means for causing said pulling means to rotate relative to said casing means, said rotating means including a second connecting portion configured to operatively connect to said first connecting portion of said pulling means, and a hollow portion extending through said rotating means such that said pulling means is inserted in the axial direction through said hollow portion until said first connecting portion is operatively connected to said second connecting portion.

2. A tester as claimed in claim 1, further comprising measuring means for measuring the tensile force generated by said pulling means.

3. A tester as claimed in claim 1, wherein said first connecting portion of said pulling means has a greater size than at least said end capable of mating with said screw member and has a geometric shape, wherein said second connecting portion of said rotating means has a shape substantially identical with, but slightly greater than, the shape of said first connecting portion, and wherein said first connecting portion and said second connecting portion are connected to each other.

4. A tester as claimed in claim 1, further comprising preventing means for preventing said first connecting portion and said second connecting portion from separating from each other when said pulling means is screwed into the screw member.

5. In a tensile strength tester including a casing, a rotating member and a pull shaft for applying a tensile force tending to pull a screw member fitted in a base material out of said base material to thereby measure a tensile strength in terms of said tensile force, (a) said casing is hollow and capable of being seated on the base material at an end thereof;

(b) said pull shaft includes a threaded end portion capable of mating with the screw member, a projection greater in size than said threaded end portion and located at an opposite side to said threaded end portion in an axial direction, and a shank connecting said threaded end portion and said projection; and (c) said rotating member is rotatably received in said casing, has a connecting portion connected to said projection of said pull shaft and a hollow portion extending through said rotating member such that said pull shaft is inserted through said hollow portion until said projection is connected to said connecting portion to thereby transfer a rotation of said rotating member to said pull shaft.

6. A tester as claimed in claim 5, wherein said connecting portion of said rotating member has a hole substantially identical in shape with, but slightly greater in size than, said projection, and a bottom contacting an underside of said projection positioned at an opposite side to an open end of said hollow portion of said rotating member.

7. A tester as claimed in claim 5, further comprising a measuring member including a first mounting portion mounted on said casing, a second mounting portion mounted on said rotating member, a body portion intervening between said first connecting portion and said second connecting portion, and a sensor mounted on said body portion for measuring a strain of said body portion.

8. A tester as claimed in claim 7, wherein said body portion is cylindrical and surrounds an axis of said pull shaft.

9. A tester as claimed in claim 7, wherein said sensor comprises a strain gauge.

10. A tester as claimed in claim 5, further comprising a preventing member disposed in and supported by said rotating member and contacting a top of said projection positioned at a same side as an open end of said hollow portion of said rotating member to thereby prevent said projection from slipping out of said connecting portion toward said open end.

11. A tester as claimed in claim 5, wherein an area in which said connecting portion and said projection contact each other generates a frictional force in the axial direction which is greater than at least a contact force to initially act between said pull shaft and the screw member.

12. A tester as claimed in claim 5, further comprising a thrust bearing surrounding the axis of said shank and contacting an inner periphery of said casing.

13. A tester as claimed in claim 12, further comprising a base intervening between said thrust bearing and said rotating member.

14. In a tensile strength tester including a casing, a pull shaft, a rotating member and a hollow member for applying a tensile force tending to pull a screw member fitted in a base material out of said base material to thereby measure a tensile strength in terms of said tensile force, (a) said casing is hollow and has a seat portion capable of contacting the base material at an end thereof;

(b) said pull shaft includes a threaded end portion adjoining said seat portion and capable of mating with the screw member, a circular shank connecting said threaded end portion and a connecting portion, and said connecting portion greater in size than said shank and different in shape from said shank;

(c) said rotating member is rotatably received in said casing and includes a hollow cylindrical portion and a second connecting portion having a first hole capable of receiving said shank and a second hole greater in size than said first hole and substantially identical in shape with, but slightly greater in size than said first connecting portion to be thereby connected to said first connecting portion, said second connecting portion being positioned at an end of said hollow cylindrical portion such that said second hole is open to an inside of said hollow cylindrical portion; and (d) said hollow member includes a first mounting portion mounted on an inner periphery of said casing at a side adjoining said seat portion, a second mounting portion contacting said second connecting portion via a bearing surrounding an axis of said shank, and a hollow body portion surrounding an axis of said pull shaft and connecting said first mounting portion and said second mounting portion.

15. A tester as claimed in claim 14, further comprising a displacement sensor mounted on said hollow body portion for measuring a strain of said hollow body portion.

16. A tester as claimed in claim 14, further comprising a stop member contacting said first connecting portion at one end and fixed to said hollow cylindrical portion at an other end portion.

17. A method of measuring, by applying a tensile force tending to pull a screw member fitted in a base material out of said base material, a tensile strength in terms of said tensile force, comprising the steps of:

inserting a pull shaft through a hollow portion extending through a rotating member via an open end of said rotating member;

causing said rotating member to retain said pull shaft;

causing holding means rotatably holding said rotating member to contact the base material; and causing said rotating member to rotate to thereby screw a threaded portion of said pull shaft into the screw member, whereby a tensile force corresponding to a rotation angle of said pull shaft is transferred to said screw member.

18. A method as claimed in claim 17, further comprising measuring a force pulling the screw member away from the base material and generated by a rotation of said pull shaft.

19. A tensile strength tester for applying a tensile force tending to pull a screw member fitted in a base material out of said base material to thereby measure a tensile strength in terms of said tensile force, said tensile strength tester comprising:

casing means for seating said tester on the base material;

pulling means for exerting a tensile force on the screw member, said pulling means including a first end having a threaded portion capable of mating with the screw member, and a first connecting portion positioned at a second end opposing said first end in an axial direction;

rotating means for causing said pulling means to rotate relative to said casing means, said rotating means including a second connecting portion configured to operatively connect to said first connecting portion of said pulling means, and an a hollow portion extending through said rotating means such that said pulling means is inserted in the axial direction through said hollow portion until said first connecting portion is operatively connected to said second connecting portion; and drive means for driving said rotating means in a direction intersecting the axial direction.

20. A tester as claimed in claim 19, further comprising measuring means for measuring a tensile force generated by said pulling means.

21. A tester as claimed in claim 19, wherein a drive axis of said drive means extends through a center of gravity of said tester.

22. In a tensile strength tester including a casing unit, a rotation unit, a pull shaft and a drive unit for applying a tensile force tending to pull a screw member fitted in a base material out of said base material to thereby measure a tensile strength in terms of said tensile force, (a) said casing unit is hollow and capable of contacting the base material at an end thereof;

(b) said pull shaft includes a threaded end portion capable of mating with the screw member, a projection greater in size than said threaded end portion and located at an opposite side to said threaded end portion in an axial direction, and a shank connecting said threaded end portion and said projection;

(c) said rotation unit is rotatably received in said casing, and has thereinside a connecting portion connected to said projection of said pull shaft and a hollow portion extending through said rotating member such that said pull shaft is inserted through said hollow portion to thereby cause said pull shaft inserted in said rotation unit to connect said connecting portion and said projection; and (d) said drive unit extends in a direction intersecting the axial direction and includes a drive transmitting portion for transmitting a driving force to said rotation unit.

23. A tester as claimed in claim 22, wherein said drive transmitting portion comprises at least one of a gear and a bevel gear.

24. A tester as claimed in claim 22, wherein the drive axis of said drive unit is offset from a center of rotation of said rotation unit.

25. A tester as claimed in claim 22, wherein said rotation unit is rotatably supported by said casing unit via at least two bearings spaced from each other in the axis direction, said drive transmitting portion being arranged between said at least two bearings.

26. A tester as claimed in claim 25, further comprising a cover portion covering a motor includes in said drive unit.

27. A tester as claimed in claim 26, further comprising a switch mounted on said cover in the vicinity of said casing unit for selectively turning on or turning off said motor.

28. A tester as claimed in claim 22, wherein an axis extending through a center of rotation of said drive unit extends through a center of gravity of said tester.

29. A tester as claimed in claim 22, further comprising a measuring unit including a first mounting portion mounted on said casing unit, a second mounting portion mounted on said rotation unit, a body portion connecting said first mounting portion and said second mounting portion, and a sensor mounted on said body portion for measuring a strain of said body portion.

30. A tester as claimed in claim 29, wherein said body portion is hollow cylindrical and surrounds said pull shaft.

31. A tester as claimed in claim 29, wherein said sensor comprises a strain gauge.

32. In a tensile strength tester including a casing, a pull shaft, a rotating member, a hollow member and a motor unit for applying a tensile force tending to pull a screw member fitted in a base material out of said base material to thereby measure a tensile strength in terms of said tensile force, (a) said casing is hollow and has a seat portion capable of contacting the base material at an end thereof;

(b) said pull shaft includes a threaded end portion adjoining said seat portion and capable of mating with the screw member, a circular shank connecting said threaded end portion and a connecting portion, and said connecting portion greater in size than said shank and different in shape from said shank;

(c) said rotating member is rotatably received in said casing and includes a hollow cylindrical portion, a second connecting portion having a first hole capable of receiving said shank and a second hole greater in size than said first hole and substantially identical in shape with, but slightly greater in size than, said first connecting portion to be thereby connected to said first connecting portion, said second connecting portion being positioned at an end of said hollow cylindrical portion such that said second hole is open to an inside of said hollow cylindrical portion, and a driven gear mounted on an outer periphery of said hollow cylindrical portion;

(d) said hollow member includes a first mounting portion mounted on an inner periphery of said casing at a side adjoining said seat portion, a second mounting portion contacting said second connecting portion via a bearing surrounding an axis of said shank, and a hollow body portion surrounding an axis of said pull shaft and connecting said first mounting portion and said second mounting portion; and (e) said motor unit includes a motor, a motor drive shaft extending in a direction intersecting the axial direction of said rotation unit, and a drive gear meshing with said driven gear for transferring an output torque of said motor to said driven gear via said drive shaft.

33. A tester as claimed in claim 32, further comprising a displacement sensor mounted on said body portion for sensing a strain of said body portion.

34. A tester as claimed in claim 32, wherein said driven gear and said drive gear each comprises either one of a worm gear and a bevel gear.

35. A tester as claimed in claim 32, wherein said drive shaft is offset from a center of rotation of said rotating member.

36. A tester as claimed in claim 32, wherein said rotating member is rotatably supported by said casing via at least two bearings spaced from each other in the axis direction, said drive gear and said driven gear being arranged between said at least two bearings.

37. A method of measuring, by applying a tensile force tending to pull a screw member fitted in a base material out of said base material, a tensile strength in terms of said tensile force, said method comprising the steps of:

inserting a pull shaft through a hollow portion extending through a rotating member via an open end of said rotating member;

causing said rotating member to retain said pull shaft;

causing holding means rotatably holding said rotating member to contact the base material; and causing a drive member to rotate said rotating member to thereby screw a threaded portion of said pull shaft into the screw member, whereby a tensile force corresponding to a rotation angle of said pull shaft is transferred to said screw member.

38. A method as claimed in claim 37, further comprising measuring a force pulling the screw member away from the base material and generated by a rotation of said pull shaft.

39. A tensile strength tester for applying a tensile force tending to pull a screw member fitted in a base material out of said base material to thereby measure a tensile strength in terms of said tensile force, said tensile strength tester comprising:

casing means to be seated on the base material;

pulling means for exerting a tensile force corresponding to a rotation angle of said pulling means on the screw member, said pulling means including a threaded portion capable of mating with the screw member, and a first connecting portion positioned at an opposite side to an end of said threaded portion capable of mating with said screw member in an axial direction;

rotating means for causing said pulling means to rotate relative to said casing means, said rotating means including a second connecting portion connected to said first connecting portion of said pulling means, and an inserting portion for allowing said threaded portion to be inserted in said rotating means from an opposite side to said second connecting portion in the axial direction; and restraining means for restraining, when said pulling means is brought into contact with the screw member, said pulling means from moving away from said screw member in the axial direction.

40. A tester as claimed in claim 39, further comprising measuring means for measuring a tensile force generated by said pulling means.

41. A tester as claimed in claim 39, wherein said preventing means comprises an elastic member.

42. A tester as claimed in claim 39, further comprising preventing means for preventing, when said pulling means moves in the axial direction, said first connecting portion and said second connecting portion from separating from each other.

43. A tester as claimed in claim 39, wherein and end of said casing means capable of contacting the base material is magnetized or provided with a magnet.

44. In a tensile strength tester including a casing unit, a rotation unit, a pull shaft and an elastic unit for applying a tensile force tending to pull a screw member fitted in a base material out of said base material to thereby measure a tensile strength in terms of said tensile force, (a) said casing unit is hollow and capable of contacting the base material at an end thereof;

(b) said pull shaft includes a threaded end portion capable of mating with the screw member, a first connecting portion including a projection positioned at an opposite side to said threaded end portion in an axial direction and greater in size than said threaded end portion, and a shank connected said threaded end portion and said projection;

(c) said rotation unit has a hollow configuration open at at least one end and rotatably received in said casing unit, and has thereinside a second connecting portion connected to said first connecting portion to thereby cause said pull shaft inserted in said rotation unit via the open end to connect said first connecting portion and said second connecting portion; and (d) said elastic unit includes an abutment portion abutting against said projection and a fixed portion fixed to said rotation unit and elastically restrains, when said pull shaft is brought into contact with the screw member, said pull shaft from moving upward in the axial direction.

45. A tester as claimed in claim 44, further comprising a measuring unit including a first mounting portion mounted on said casing unit, a second mounting portion mounted on said rotation unit, a body portion intervening between said first connecting portion and said second connecting portion, and a sensor mounted on said body portion for measuring a strain of said body portion.

46. A tester as claimed in claim 45, wherein said body portion is cylindrical and surrounds an axis of said pull shaft.

47. A tester as claimed in claim 44, wherein said threaded end portion of said casing unit is magnetized or provided with a magnet.

48. A tester as claimed in claim 44, wherein said threaded end portion of said casing unit is held in threaded engagement with a body portion of said casing unit.

49. A tester as claimed in claim 48, wherein said threaded end portion and said body portion of said casing unit are threaded in an opposite direction to said pull shaft.

50. A tester as claimed in claim 44, further comprising a regulating member including an end portion for regulation spaced in the axial direction from an end of said pull member opposite to said threaded end portion by a distance greater than a length of said first connecting portion and said second connecting portion connected to each other, and a fixed portion fixed to said rotation unit to thereby cause said elastic unit to follow a rotation of said rotation unit.

51. In a tensile strength tester including a casing, a pull shaft, a rotating member, a hollow member and a plug unit for applying a tensile force tending to pull a screw member fitted in a base material out of said base material to thereby measure a tensile strength in terms of said tensile force, (a) said casing is hollow and has a seat portion capable of contacting the base material at an end thereof;

(b) said pull shaft includes a threaded end portion adjoining said seat portion and capable of mating with said screw member, a circular shank connecting said threaded end portion and a connecting portion, and said connecting portion greater in size than said shank and different in shape from said shank;

(c) said rotating member is rotatably received in said casing and includes a hollow cylindrical portion, a second connecting portion having a first hole capable of receiving said shank and a second hole greater in size than said first hole and substantially identical in shape with, but slightly greater in size than, said first connecting portion to be thereby connected to said first connecting portion, said second connecting portion being positioned at an end of said hollow cylindrical portion such that said second hole is open to an inside of said hollow cylindrical portion;

(d) said hollow member includes a first mounting portion mounted on an inner periphery of said casing at a side adjoining said seat portion, a second mounting portion contacting said second connecting portion via a bearing surrounding an axis of said shank, and a hollow body portion surrounding an axis of said pull shaft and connecting said first mounting portion and said second mounting portion; and (e) said plug unit includes a body portion fixed to said hollow cylindrical portion and an elastic portion retained by a fixed portion of said body portion at one end fixed to said rotation unit at the other end and causes said elastic member to follow a rotation of said rotation unit, whereby when said pull shaft is brought into contact with the screw member, said pull shaft is elastically restrained from moving upward in the axial direction by said elastic portion.

52. A tester as claimed in claim 51, further comprising a displacement sensor mounted on said hollow body portion for measuring a strain of said hollow body portion.

53. A tester as claimed in claim 51, wherein said seat portion is screwed into a body portion of said casing in an opposite direction to said pull shaft.

54. A tester as claimed in claim 51, wherein an end of said seat portion to contact the base material is magnetized or provided with a magnet.

55. A tester as claimed in claim 51, wherein said plug unit further includes a lug for regulation connected to said body portion of said plug unit at one end and spaced in the axial direction from said first connecting portion at the other end by a distance greater than a length of said first connecting portion and said second connecting portion connected to each other.

56. A method of measuring, by applying a tensile force tending to pull a screw member fitted in a base material out of said base material, a tensile strength in terms of said tensile force, said method comprising the steps of:

inserting a pull shaft through a hollow portion extending through a rotating member via an open end of said rotating member;

causing said rotating member to retain said pull shaft;

causing said pull shaft to contact the screw member to thereby cause said pull shaft move upward in an axial direction while being biased downward by an elastic member;

causing holding means rotatably holding said rotating member to contact the base material; and causing a drive member to rotate said rotating member such that a threaded portion of said pull shaft is screwed into the screw member, thereby transferring a tensile force corresponding to a rotation angle of said pull shaft to said screw member.

57. A method as claimed in claim 56, further comprising measuring a force pulling the screw member away from the base material and generated by a rotation of said pull shaft.

* * * * *